United States Patent
Raje et al.

(10) Patent No.: US 11,612,740 B2
(45) Date of Patent: Mar. 28, 2023

(54) ELECTRODE ARRAY MANUFACTURE

(71) Applicant: Cochlear Limited, Macquarie University (AU)

(72) Inventors: Milind Chandrakant Raje, Macquarie University (AU); Timothy McInnes, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 55 days.

(21) Appl. No.: 16/765,555

(22) PCT Filed: Nov. 20, 2018

(86) PCT No.: PCT/IB2018/059111
§ 371 (c)(1),
(2) Date: May 20, 2020

(87) PCT Pub. No.: WO2019/097495
PCT Pub. Date: May 23, 2019

(65) Prior Publication Data
US 2020/0306525 A1    Oct. 1, 2020

Related U.S. Application Data

(60) Provisional application No. 62/588,723, filed on Nov. 20, 2017.

(51) Int. Cl.
*A61N 1/05* (2006.01)
*A61N 1/375* (2006.01)

(52) U.S. Cl.
CPC .......... *A61N 1/0541* (2013.01); *A61N 1/375* (2013.01)

(58) Field of Classification Search
CPC .... A61N 1/36038; A61N 1/0541; A61N 1/37; A61N 1/375
See application file for complete search history.

(56) References Cited

U.S. PATENT DOCUMENTS 4,172,451 A    10/1979    Kline
4,484,586 A    11/1984    McMickle et al.
(Continued)

FOREIGN PATENT DOCUMENTS

CN    101708353 A    5/2010
CN    102123760 A    7/2011
(Continued)

OTHER PUBLICATIONS

Office action and Search Report for Chinese Patent Application No. 201880074671.9, dated Jan. 14, 2021.
(Continued)

*Primary Examiner* — Jon Eric C Morales
(74) *Attorney, Agent, or Firm* — Pilloff Passino & Cosenza LLP; Martin J. Cosenza

(57) ABSTRACT

Winding a wire at a first location such that the wire is bunched at the first location, extending the wire from the first location to a second location, winding the wire at the second location such that the wire is bunched at the second location, extending the wire from the second location back towards the first location to a third location proximate the second location, winding the wire at the third location such that the wire is bunched at the third location, extending the wire from the third location back towards the first location to a fourth location at least proximate the first location, winding the wire at the fourth location such that the wire is bunched at the fourth location, severing the wire at one or more locations, and forming an electrode assembly utilizing the windings.

26 Claims, 52 Drawing Sheets

(56) References Cited

U.S. PATENT DOCUMENTS

| | | | |
|---|---|---|---|
| 5,016,646 A | 5/1991 | Gotthardt et al. | |
| 5,466,253 A | 11/1995 | Doan | |
| 5,584,873 A | 12/1996 | Shoberg et al. | |
| 5,649,974 A | 7/1997 | Nelson et al. | |
| 5,713,944 A | 2/1998 | Kroll | |
| 7,212,867 B2 | 5/2007 | Van Venrooij et al. | |
| 7,558,632 B1 | 7/2009 | Salys | |
| 7,899,548 B2 | 3/2011 | Barker | |
| 9,044,589 B2 | 6/2015 | Raje et al. | |
| 2002/0049485 A1 | 4/2002 | Smits | |
| 2002/0111664 A1 | 8/2002 | Bartig et al. | |
| 2003/0236562 A1 | 12/2003 | Kuzma | |
| 2005/0171587 A1 | 8/2005 | Low et al. | |
| 2008/0097566 A1 | 4/2008 | Colliou | |
| 2008/0147158 A1 | 6/2008 | Zweber et al. | |
| 2009/0067649 A1 | 3/2009 | Nikles et al. | |
| 2009/0292237 A1 | 11/2009 | Overstreet et al. | |
| 2010/0274319 A1* | 10/2010 | Meskens ............ A61N 1/36038 607/57 | |
| 2011/0152991 A1 | 6/2011 | Dadd et al. | |
| 2012/0101559 A1 | 4/2012 | Jolly et al. | |
| 2014/0074214 A1 | 3/2014 | Raje et al. | |
| 2014/0121742 A1 | 5/2014 | Boser et al. | |
| 2014/0288618 A1 | 9/2014 | Li et al. | |
| 2015/0335880 A1 | 11/2015 | Zimmerling et al. | |

FOREIGN PATENT DOCUMENTS

| | | |
|---|---|---|
| CN | 104870051 A | 8/2015 |
| EP | 2034770 A2 | 3/2009 |
| WO | 8304182 A1 | 12/1983 |
| WO | 2012003297 A1 | 1/2012 |
| WO | 2016168485 A1 | 10/2016 |

OTHER PUBLICATIONS

International Search Report & Written Opinion for PCT/IB2018/059111, dated Mar. 11, 2019.

* cited by examiner

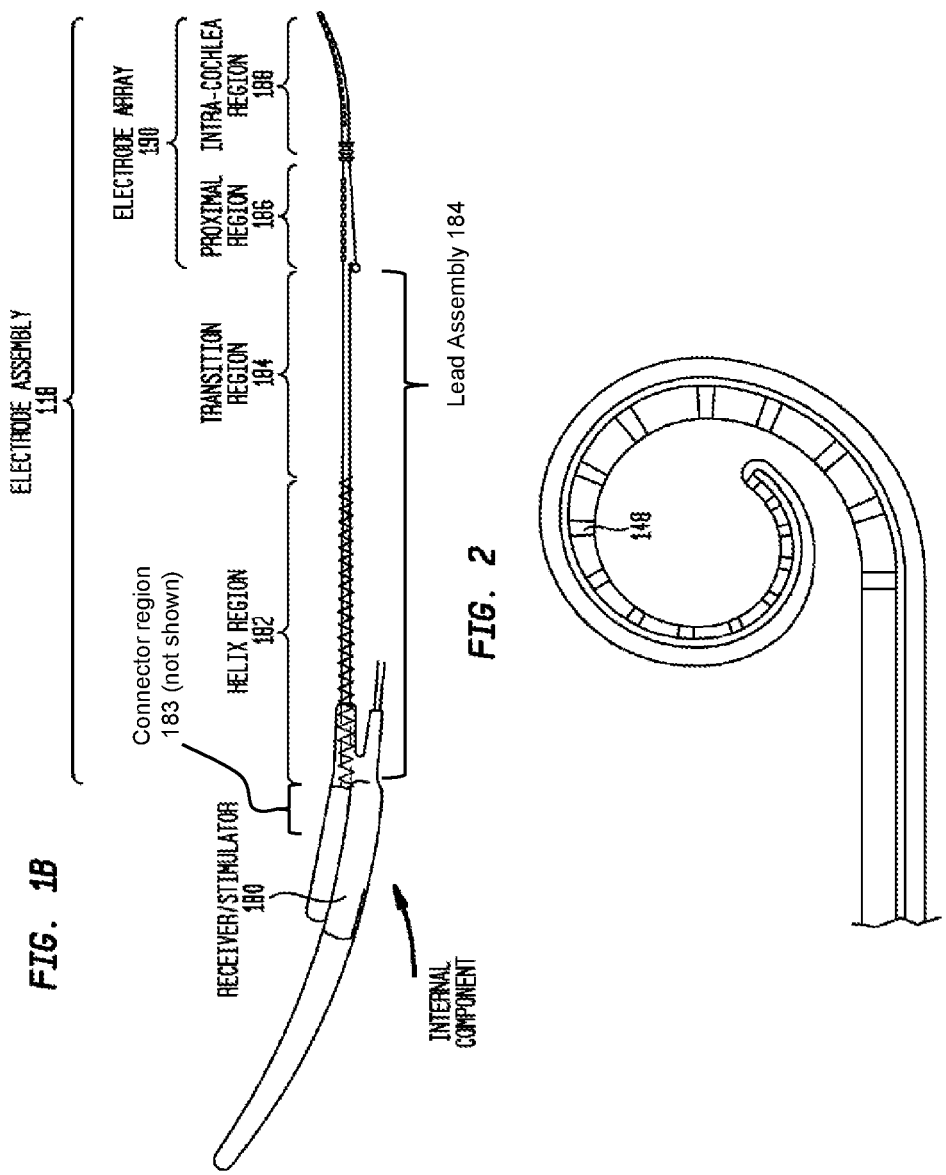

ELECTRODE ARRAY MANUFACTURE

CROSS-REFERENCE TO RELATED APPLICATIONS

This application claims priority to U.S. Provisional Application No. 62/588,723, entitled ELECTRODE ARRAY MANUFACTURE, filed on Nov. 20, 2017, naming Milind Chandrakant RAJE of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In an exemplary embodiment, there is a method comprising winding a wire at a first location such that the wire is bunched at the first location, extending the wire from the first location to a second location, winding the wire at the second location such that the wire is bunched at the second location, extending the wire from the second location back towards the first location to a third location proximate the second location, winding the wire at the third location such that the wire is bunched at the third location, extending the wire from the third location back towards the first location to a fourth location at least proximate the first location, winding the wire at the fourth location such that the wire is bunched at the fourth location, severing the wire at one or more locations, and forming an electrode assembly utilizing the windings.

In another exemplary embodiment, there is a method, comprising, winding a wire at a first location such that the wire is bunched at the first location, extending the wire from the first location to a second location, winding the wire at the second location such that the wire is bunched at the second location, extending the wire from the second location back towards the first location to a location at least proximate the first location, wherein the wire is contiguous from the first location to the location at least proximate the first location, and forming an electrode array utilizing the windings.

In another exemplary embodiment, there is an apparatus, comprising a plurality of first wire windings, a plurality of second wire windings, wherein the apparatus is an implantable electrode assembly, the plurality of first wire windings establish an input end of the implantable electrode assembly, the plurality of second wire windings establish a stimulation end of the implantable electrode assembly, respective windings of the first wire windings are made up of the same respective single wires that make up respective windings of the second wire windings; and at least one of, the plurality of second wire windings and the vicinity thereabout are free of wire ends, or respective two wire paths extend from the respective windings of the first wire windings to the respective windings of the second wire windings.

In an exemplary embodiment, there is an apparatus, comprising at least five first wire windings, at least five second wire windings, wherein the apparatus is an implantable electrode assembly, the five first wire windings establish an input end of the implantable electrode assembly, the five second wire windings establish a stimulation end of the implantable electrode assembly, respective windings of the five first wire windings are made up of the same respective single wires that makes up respective windings of the five second wire windings, an respective sub-portions of respective wires that connect the respective windings all at least one of extend through the windings on insides thereof or do not pass from one side of any winding to another side of any winding.

In another exemplary embodiment, there is a method, comprising making an embryonic electrical assembly of a cochlear electrode assembly from a single wire, the embryonic electrical assembly providing at least five separate channels for the cochlear electrode assembly, and not including the final separation of the embryonic assembly from the wire, separating the single wire of the embryonic electrical assembly at at least four different locations along the wire to electrically isolate the respective different channels of the at least five separate channels.

BRIEF DESCRIPTION OF THE DRAWINGS

Embodiments of the present invention are described below with reference to the attached drawings, in which:

FIG. 1B is a side view of the implantable components of the cochlear implant illustrated in FIG. 1A;

FIG. 2 is a side view of an embodiment of the electrode array illustrated in FIGS. 1A and 1B in a curled orientation;

FIGS. 49-511 present some additional schematics relating to some utilitarian methods of implementing some of the teachings herein.

DETAILED DESCRIPTION

Figure 1A:
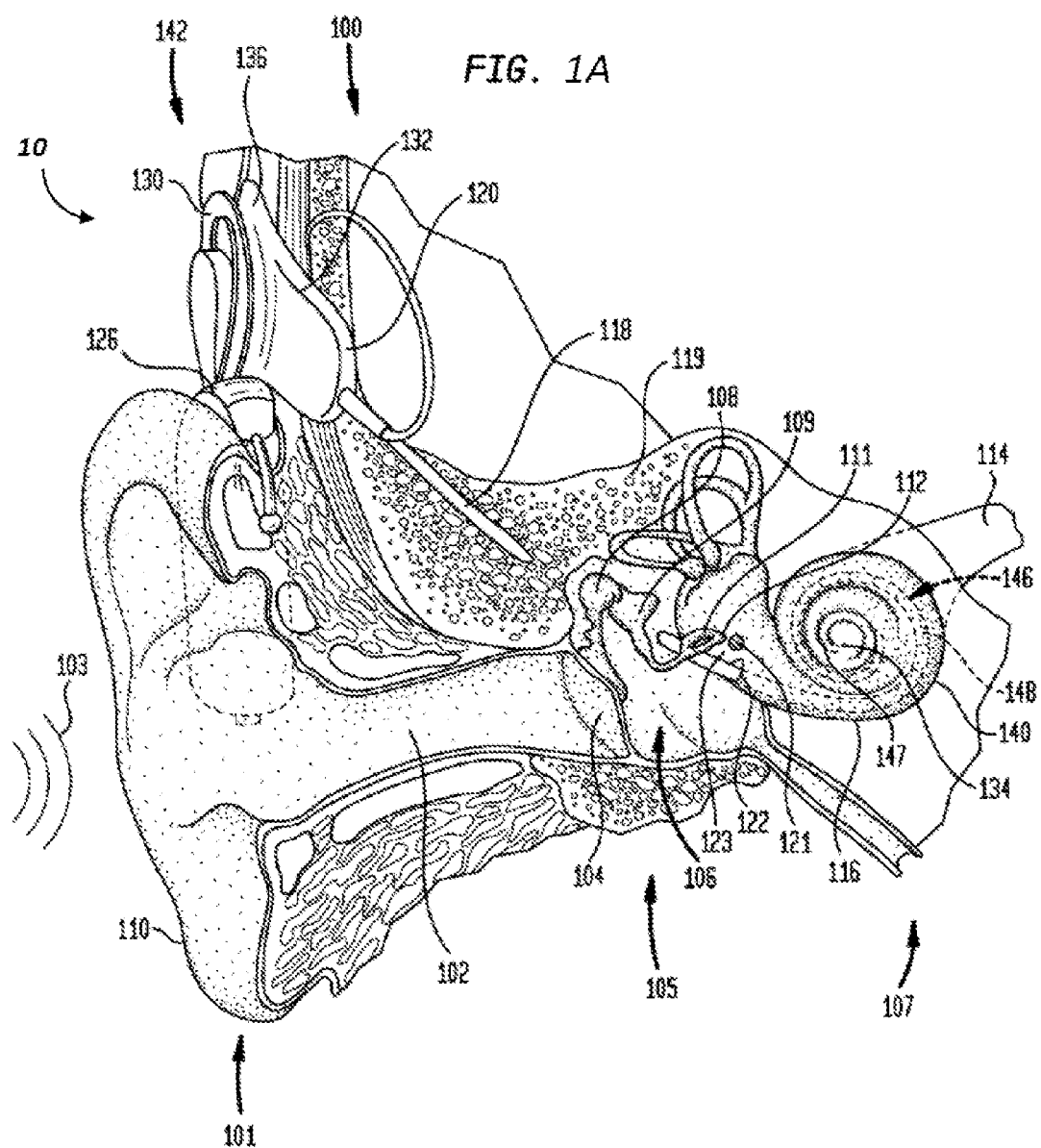
FIG. 1A is a perspective view of an exemplary hearing prosthesis utilized in some exemplary embodiments.

FIG. 1A is a perspective view of a totally implantable cochlear implant according to an exemplary embodiment, referred to as cochlear implant 100, implanted in a recipient. The totally implantable cochlear implant 100 is part of a system 10 that can include external components, as will be detailed below.

In an alternate embodiment, the cochlear implant system is not a totally implantable system. By way of example, the cochlear implant system includes an external component that includes a microphone and a sound processor. The sound processor processes signals from the microphone, and generates a signal that is transmitted transcutaneously to an implantable component which then uses the signal to stimulate tissue and evoke a hearing percept.

It is noted that in some conventional parlances, the entire system 10 is referred to as a cochlear implant, especially in the case of a cochlear implant that is not totally implantable. Herein, the phrase cochlear implant refers to the implantable component, and the phrase cochlear implant system refers to the entire system 10. That is, the phrase cochlear implant corresponds to the implantable component of a non-totally implantable cochlear implant system.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant.

In the illustrative arrangement of FIG. 1A, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand/or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand/or multi-strand platinum or gold wire.

Cochlear implant 100 further comprises a main implantable component 120 and an elongate stimulating assembly 118. In embodiments of the present invention, internal energy transfer assembly 132 and main implantable component 120 are hermetically sealed within a biocompatible housing. In embodiments of the present invention, main implantable component 120 includes a sound processing unit (not shown) to convert the sound signals received by the implantable microphone in internal energy transfer assembly 132 to data signals. Main implantable component 120 further includes a stimulator unit (also not shown) which generates electrical stimulation signals based on the data signals. The electrical stimulation signals are delivered to the recipient via elongate stimulating assembly 118.

Elongate stimulating assembly 118 has a proximal end connected to main implantable component 120, and a distal end implanted in cochlea 140. Stimulating assembly 118 extends from main implantable component 120 to cochlea 140 through mastoid bone 119. In some embodiments stimulating assembly 118 may be implanted at least in basal region 116, and sometimes further. For example, stimulating assembly 118 may extend towards apical end of cochlea 140, referred to as cochlea apex 134. In certain circumstances, stimulating assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating assembly 118 comprises a longitudinally aligned and distally extending array 146 of electrodes 148, disposed along a length thereof. As noted, a stimulator unit generates stimulation signals which are applied by stimulating contacts 148, which, in an exemplary embodiment, are electrodes, to cochlea 140, thereby stimulating auditory nerve 114. In an exemplary embodiment, stimulation contacts can be any type of component that stimulates the cochlea (e.g., mechanical components, such as piezoelectric devices that move or vibrate, thus stimulating the cochlea (e.g., by inducing movement of the fluid in the cochlea), electrodes that apply current to the cochlea, etc.). Embodiments detailed herein will generally be described in terms of an electrode assembly 118 utilizing electrodes as elements 148. It is noted that alternate embodiments can utilize other types of stimulating devices. Any device, system, or method of stimulating the cochlea can be utilized in at least some embodiments.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in main implantable component 120, or disposed in a separate implanted location.

It is noted that the teachings detailed herein and/or variations thereof can be utilized with a non-totally implantable prosthesis. That is, in an alternate embodiment of the cochlear implant 100, the cochlear implant 100 is a traditional hearing prosthesis.

While various aspects of the present invention are described with reference to a cochlear implant (whether it be a device utilizing electrodes or stimulating contacts that impart vibration and/or mechanical fluid movement within the cochlea), it will be understood that various aspects of the embodiments detailed herein are equally applicable to other stimulating medical devices having an array of electrical simulating electrodes such as auditory brain implant (ABI), functional electrical stimulation (FES), spinal cord stimulation (SC S), penetrating ABI electrodes (PABI), and so on. Further, it should be appreciated that the present invention is applicable to stimulating medical devices having electrical stimulating electrodes of all types such as straight electrodes, perimodiolar electrodes and short/basilar electrodes. Also, various aspects of the embodiments detailed herein and/or variations thereof are applicable to devices that are non-stimulating and/or have functionality different from stimulating tissue, such as for, example, any intra-body dynamic phenomenon (e.g., pressure, or other phenomenon consistent with the teachings detailed herein) measurement/sensing, etc., which can include use of these teachings to sense or otherwise detect a phenomenon at a location other than the cochlea (e.g., within a cavity containing the brain, the heart, etc.). Additional embodiments are applicable to bone conduction devices, Direct Acoustic Cochlear Stimulators/Middle Ear Prostheses, and conventional acoustic hearing aids. Any device, system, or method of evoking a hearing percept can be used in conjunction with the teachings detailed herein. The teachings detailed herein can be utilized with other types of stimulating devices, such as retinal implants, spinal implants, heart stimulators, pacemakers, implanted sensor devices, etc. Note also that the teachings detailed herein can be utilized with devices that do not necessarily provide stimulation, but simply require an electrical connection between a lead assembly and an electronics component.

FIG. 1B is a side view of the internal component of cochlear implant 100 without the other components of system 10 (e.g., the external components). Cochlear implant 100 comprises a receiver/stimulator 180 (combination of main implantable component 120 and internal energy transfer assembly 132) and a stimulating assembly or lead 118. Stimulating assembly 118 includes a helix region 182, a transition region 184, a proximal region 186, and an intra-cochlear region 188. There is also a connector region 183, which is located inside and/or proximate the receiver stimulator 180, and is used to electrically connect the electrode assembly to receiver stimulator. Additional details of this will be provided below.

Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

FIG. 2 is a side view of electrode array assembly 190 in a curled orientation, as it would be when inserted in a recipient's cochlea, with electrode contacts 148 located on the inside of the curve. FIG. 2 depicts the electrode array of FIG. 1B in situ in a patient's cochlea 140.

Figure 3:
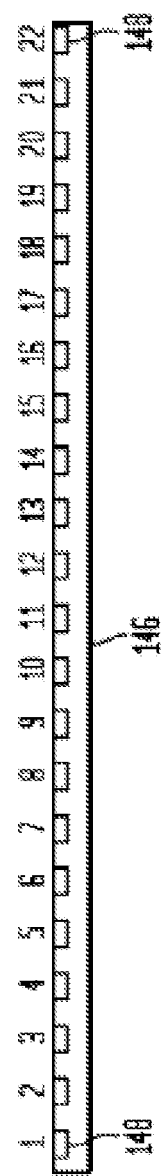
FIG. 3 is a functional schematic of an electrode array including 22 electrodes spaced apart from one another.

FIG. 3 illustrates a more detailed view, albeit functionally, of an exemplary electrode array 146 comprising a plurality of electrodes 148 labeled 1-22, in accordance with an embodiment. In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel) as will be discussed in greater detail below. Briefly, it is noted that during stimulation by the electrodes to evoke a hearing percept, one or more of electrodes 148 is activated at a given electrode stimulation level (e.g., current level).

There is utilitarian value in a structure of a cochlear implant where one or more of the electrodes 148 is electrically isolated from one or more other electrodes 148 (e.g., current does not flow from one electrode to another electrode when the cochlear implant 100, or at least the array 190, is isolated from a conductive media that is not part of the cochlear implant 100, at least not unless the cochlear implant is configured to alternately enable such flow, in which case there is utilitarian value in a structure that can alternately prevent such flow from occurring). Corollary to this is that there is utilitarian value in a structure of a cochlear implant where one or more of the electrodes 148 are in electrical conductivity with the receiver/stimulator 180 (e.g., current flows from the receiver/stimulator 182 one or more of the electrodes 148, which, in an exemplary embodiment, the current flows through the electrode assembly 118 from the receiver/stimulator 180).

In at least some exemplary embodiments, there is utilitarian value in testing for shorts and/or opens with respect to the electrode assembly 118. In at least some exemplary embodiments, a short is detected as a low impedance between two or more electrodes 148. In at least some exemplary embodiments, an open is detected as a high impedance between a given electrode 148 and another electrode (whether the another electrode be on the same electrode array as the given electrode, or on a separate component (e.g., the extra-cochlear electrode on another lead, an electrode on the receiver stimulator, etc.) and/or between a given electrode 148 and the receiver/stimulator 180.

In an exemplary embodiment, a test for an open entails making an electrical connection to the electrode 148 under test. In an exemplary embodiment, a test for a closed entails energizing one electrode 148 and testing for an electrical current at one of the other electrodes 148.

In at least some exemplary embodiments, the cochlear implant 100, or at least the electrode array assembly 190, is shipped in a sterilely sealed sterile package. According to some exemplary embodiments, there is utilitarian value in testing for opens and shorts while the cochlear implant 100 in general, and the electrode array assembly 190, remains sterilely sealed in the sterile package. In at least some exemplary embodiments, this can enable testing for opens and shorts without exposing the cochlear implant 100, or at least the electrode array assembly 190, to a nonsterile environment. In an exemplary embodiment, this can entail detecting for an open and/or a short circuit without opening the package, and enabling the cochlear implant 100 to be returned to the manufacturer in a sterile environment (because the packaging was never opened) upon a determination that there exist an open and/or a short.

Figure 4:
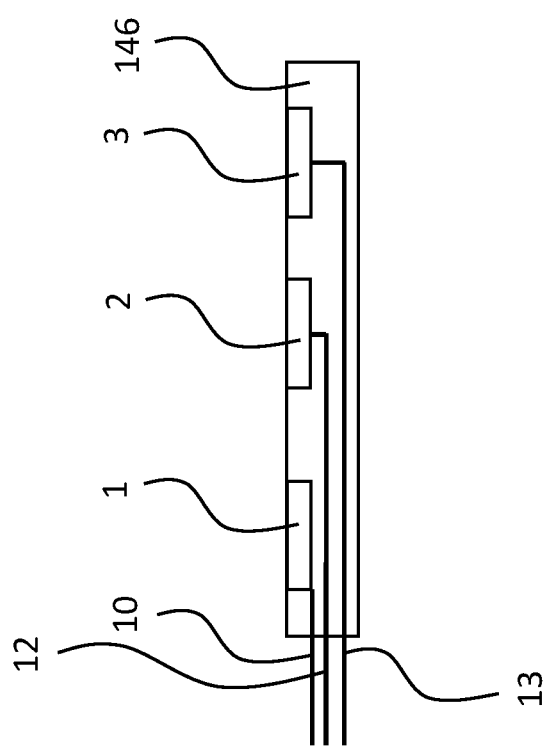
FIGS. 4 and 5 functionally depict channels of an electrode assembly.

In general terms, FIG. 4 depicts a quasi-functional diagram of a portion of electrode array 146, depicting electrodes 1, 2, and 3, which are respectively connected to leads 10, 12, and 13, which leads extend from the respective electrodes to the proximal end of the electrode array assembly 190, and then to receiver/stimulator 180. While only three electrodes and three leads are depicted in FIG. 4 (and FIG. 5), it is to be understood that in at least some embodiments, more electrodes and more leads are present in electrode array 146. Indeed, with respect to FIG. 1B, there are 22 electrodes and 22 leads (although in some embodiments, there are 44 leads—more on this below—other amounts of leads can be present as well vis-à-vis the 22 electrode embodiment). Only three electrodes and only three leads are depicted in FIG. 4 for clarity. To be clear, any number of leads and any number of electrodes can be present in some embodiments.

In an exemplary embodiment, the leads extend from the intracochlear region, through the proximal region and then the transition regions and then the through the helix region to the connector region 183. Briefly, it is noted that while some embodiments include the helix region 182, in some other embodiments, there is no helix region, but instead, the leads extend in a manner that is generally parallel to the body of the lead assembly 187 that extends from the electrode array 190 to the connector region 183.

In general terms, FIG. 4 depicts a quasi-functional diagram of a portion of electrode array 146, depicting electrodes 1, 2, and 3, which are respectively connected to leads 10, 12, and 13, which leads extend from the respective electrodes to the proximal end of the electrode array assembly 190, and then to receiver/stimulator 180. While only three electrodes and three leads are depicted in FIG. 4, it is to be understood that in at least some embodiments, more electrodes and more leads are present in electrode array 146. Indeed, with respect to FIG. 1B, there are 22 electrodes and 22 leads (although in some embodiments, there are 44 leads—more on this below—other amounts of leads can be present as well vis-à-vis the 22 electrode embodiment). Only three electrodes and only three leads are depicted in FIG. 4 for clarity. To be clear, any number of leads and any number of electrodes can be present in some embodiments.

Figure 5:
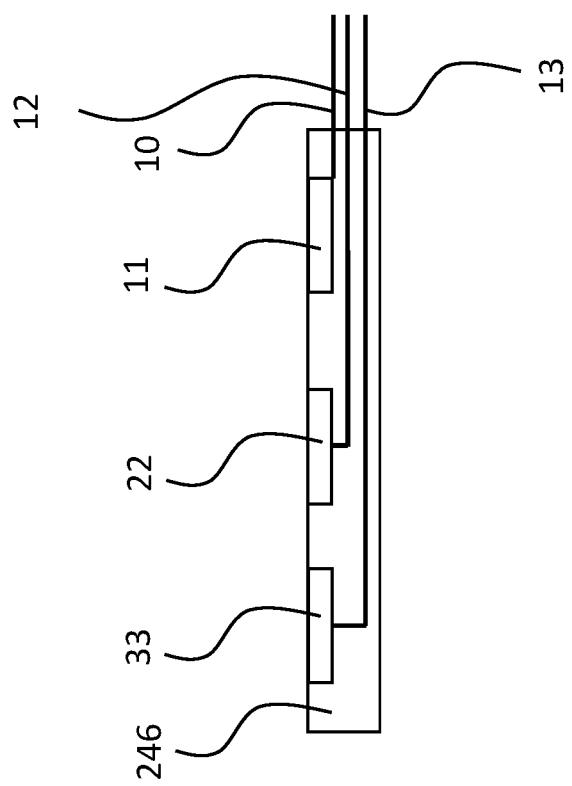

In general terms, FIG. 5 depicts a quasi-functional diagram of a portion of connector 183 (sometimes referred to herein as the stimulator end of the electrode assembly), depicting contacts 11, 22, and 33, which are respectively connected to leads 10, 12, and 13, which leads have extended from the respective electrodes to the proximal end of the electrode array assembly 190, and then to receiver/stimulator 180. These contacts are supported by an elastomer, establishing contact array 246. While only three contacts and three leads are depicted in FIG. 5, it is to be understood that in at least some embodiments, more contacts and more leads are present in electrode array 146. Indeed, with respect to FIG. 1B, there are 22 contacts and 22 leads (although in some embodiments, there are 44 leads—more on this below—other amounts of leads can be present as well vis-à-vis the 22 electrode embodiment). Only three contacts and only three leads are depicted in FIG. 4 for clarity. To be clear, any number of leads and any number of contacts can be present in some embodiments.

The terms electrodes and contacts are used herein. The term electrode is utilized with respect to the parts of the electrode array that results in electrical current flowing to/from tissue/the part of the electrode array that is exposed to body fluids (albeit potentially indirectly, such as in embodiments where there is a protective layer between the electrical conductive material of the electrodes and the body tissue). The term contacts is utilized with respect to parts of the electrode array that enable electrical contact with the circuitry or other components of the receiver stimulator 180. In this regard, contacts "contact" another electrical assembly so as to enable the flow of electricity via a solid path/conductor based path (as opposed to the electrodes that are located in, for example, the cochlea, where those electrodes enable flow of electricity via a fluid path/tissue based path). That said, it is noted that in some teachings in the art, the portions of the electrode array that are located inside the cochlea and otherwise exposed to body fluids are sometimes also referred to as electrical contacts. Thus, the term electrodes can encompass electrical contacts.

In at least some exemplary embodiments, there are corresponding electrical contacts that interface with the contacts seen in FIG. 5, which contacts are located on the receiver stimulator 180. Those contacts are in turn in electrical contact with circuitry of the receiver stimulator which circuitry provides an electrical current to the given contacts so as to ultimately energize certain electrodes of the electrode array to evoke a hearing percept. In some embodiments, the contacts are joined to each other so as to establish a connection (the connection can be established by any joining method or any other method, such as welding (e.g., laser welding), crimping, crimping, etc.). In some other embodiments, the contacts mechanically but removably interface with each other so as to maintain electrical contact during normal operation. It is also noted that in some embodiments, there are no contacts on the electrode array per se, but instead, end(s) of the electrical leads are utilized to connect to corresponding electrical components of the receiver stimulator (e.g., by crimping). Some various ways to establish the electrical connection between the electrode array 190 and the receiver stimulator assembly 180 will be described below. First however, some exemplary embodiments of how to make the electrode array 190 in general, and the electrodes and leads, and, in some embodiments, the contacts, will now be described in particular.

Figure 6:
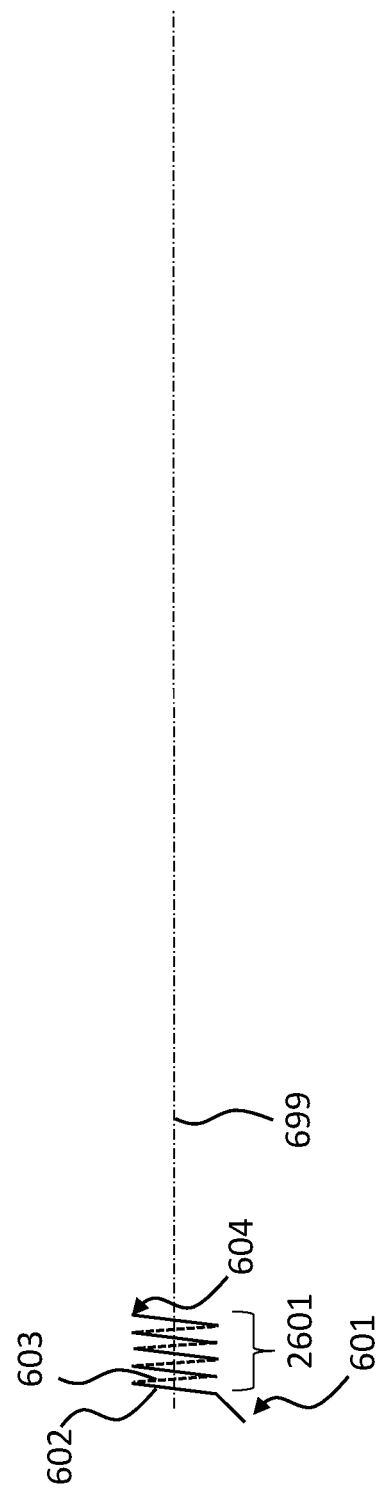
FIGS. 6-17 and 20-25 variously depict embryonic electrical systems of exemplary electrode arrays and otherwise pictorially depict actions/sub actions exemplary methods of making the embryonic electrical systems according to some embodiments.

FIG. 6 depicts an exemplary embodiment of a portion of an embryonic contact array 246. In describing the apparatus, an exemplary method of making the apparatus will also be described. Referring to FIG. 6, there is a beginning of an electrical lead wire 601, which lead wire includes a conductor that is sheathed in an electrical insulation material. The wire extends from the beginning 601 and is wound about a mandrel (an exemplary embodiment of a mandrel is detailed below—the mandrel can be of any sizes or shape that can enable the teachings herein—different cross-section sizes and shapes (rectangular, oval shaped, circle, pentagon, etc.) and varying cross sections (both in size and shape), the mandrel could be coated (e.g., with silicone) or uncoated) at a first location, ultimately to establish at least a portion of a contact (e.g., contact 3 in the embodiment of FIGS. 4-5, contact 22 in an embodiment of a 22 electrode array). In some embodiments, a mandrel is not utilized, but instead, the plasticity of the wire is utilized to maintain the curvature, where, for example, the dispenser of the wire bends the wire so as to plastically deform the wire such that the wire maintains the desired curvature. In any event, FIG. 6 depicts the near portion of a given wind as element 602, and the far portion of a given wind (e.g., the portion that would be eclipsed by the mandrel) as element 603, which is represented in dashed lines. As can be seen, the wire is wound at the first location a number of times, the end of the given winding corresponding to element 604. In this exemplary embodiment, the wire is wound 4½ times, although in some other embodiments, it can be wound more or fewer. In an exemplary embodiment, the number of windings at this first location corresponds to X.Y, where X is any whole number between and inclusive of 1 and 50, and Y is any number that has utilitarian value, such as any number between and inclusive of 0.01 and 0.99 in 0.01 increments (e.g., 0.25, 0.5, 0.75, 0.83). In an exemplary embodiment, the number of windings of the first location corresponds to a range between an inclusive of 1.00 and 50.00 and any value or range of values therebetween in 0.01 increments (e.g., 10.22, 33.33, 20.5 to 44.44, etc.). It is noted that in some embodiments, the number of windings can be greater than those just detailed, while in other embodiments, the number of windings can be fewer. Any number of windings that can enable the teachings detailed herein can be utilized in at least some exemplary embodiments.

Collectively, the windings establish a "bunching." In this regard, it is to be understood that the wire is bunched at the first location depicted in FIG. 6. Some additional features of bunching will be described in greater detail below.

In the exemplary embodiment depicted in FIG. 6, there is spacing depicted between the windings. That is, in the embodiment depicted in FIG. 6, if such were to scale, the sides of the wires would not contact each other. That is, the pitch is relatively high such that, with respect to the diameters of the wires utilized, the wires do not contact each other with respect to the bunching depicted. Conversely, in an alternate embodiment, the winding has a pitch such that the sides of the wires abut one another from one winding to another for a given bunching. That is, in some exemplary embodiments, the pitch to diameter ratio of a plurality of windings is such that the pitch is at a minimum with respect to the wire diameter at the given bunching/winding. Thus, in some exemplary embodiments, the density of wire in a given bunching based on pitch is at a maximum. Any disclosure herein of a large pitch that creates space between the windings also corresponds to a disclosure of a smaller pitch where there is a relatively minimal space between the windings, as well as a disclosure where there is no space between the windings (i.e., the wires touch each other).

Figure 7:
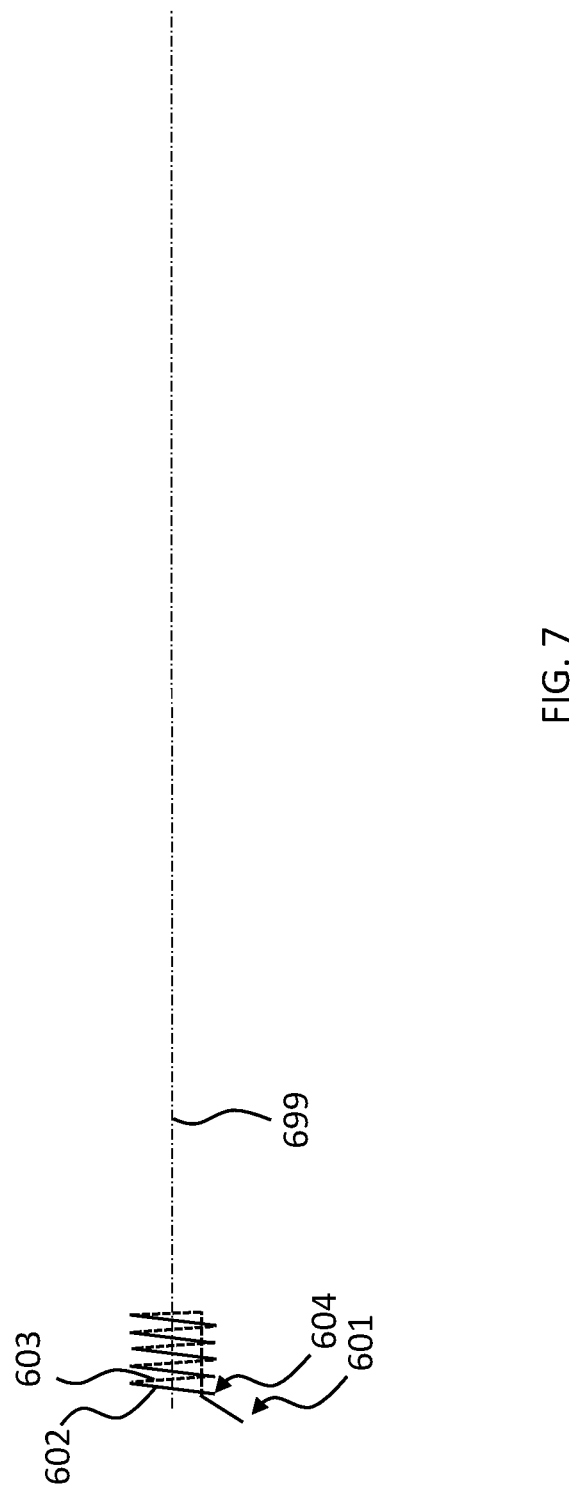

Briefly, FIG. 7 depicts an exemplary embodiment where the beginning of the wire is the same (element 601) but the wire is led forward along the longitudinal axis 699 of the winding, and then the windings begin in a backwards direction, where the windings and at point 604 (or at least the winding in that direction ends at point 604—in an exemplary embodiment, the winding then can be driven forward at that point so as to overlap the wires, in some embodiments, were to place wires in between existing wires if the pitch to diameter ratio of the winding operation in the backward direction permits such). In FIG. 7, the dashed line that is extending in the horizontal direction is dashed so as to represent the fact that the windings overlap that portion. That is, in this embodiment, the dashed line is not representative of eclipsing via the mandrel, but instead the concept that the windings eclipsed at least a portion of the horizontal extension.

Figure 8:
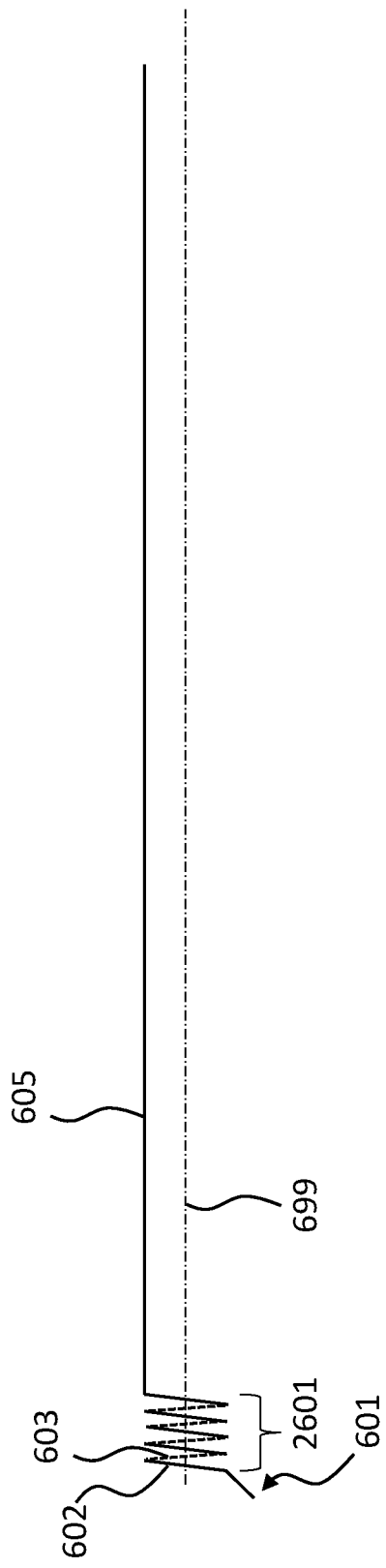
Figure 9:
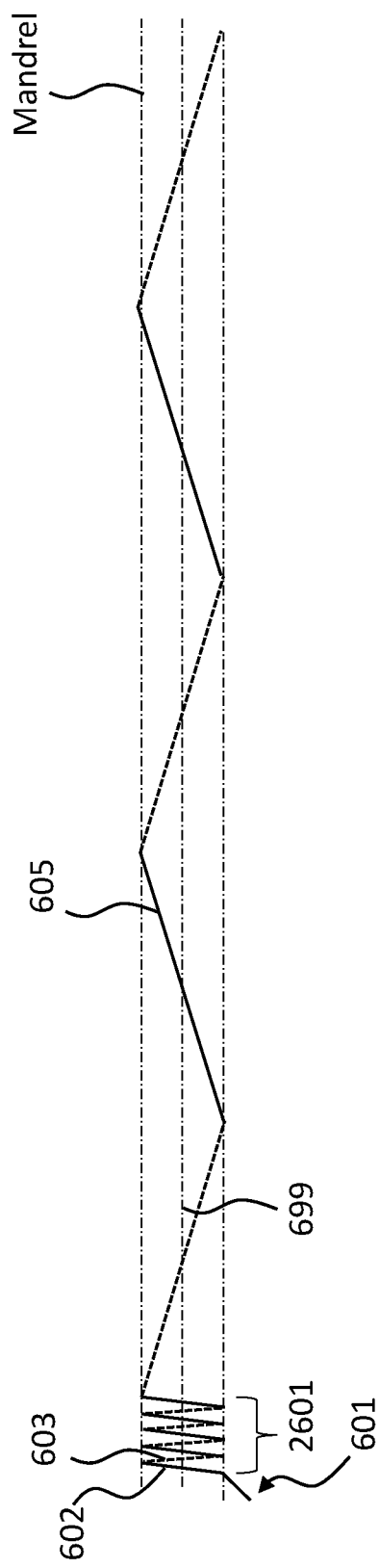

FIG. 8 keys off the embodiment of FIG. 6, where a wire subsection 605 extends in the horizontal direction along the longitudinal axis 699. In this regard, in this exemplary embodiment, there is thus the action of winding the wire at a first location such that the wire is bunched at the first location, and the action of extending the wire from the first location to a second location that is remote from the first location. To be clear, subsection 605 is not bunched. Moreover, in an exemplary embodiment, as can be seen in FIG. 9, subsection 605 can include a winding feature, which can correspond to the helix region 182. However, the pitch is relatively large relative to the pitch of the bunched sections, and thus this section does not include a bunching. It is also noted that in an exemplary embodiment, the density of the windings can be varied to adjust or otherwise achieve a desired stiffness at a local spot on the assembly, or even in a quasi global manner (e.g., such as with respect to the entire intra cochlear section). Indeed, while some embodiments herein are directed to having bunchings only at the electrode/contact locations, in other embodiments, there are bunchings at other locations away from the electrode/contact locations to achieve a stiffer assembly at such locations relative to that which would be the case without the bunchings.

By "remote" it is meant that the locations are remote with respect to the overall final product of the electrode array 190 or at least the embryonic electrode array 190.

Figure 10:
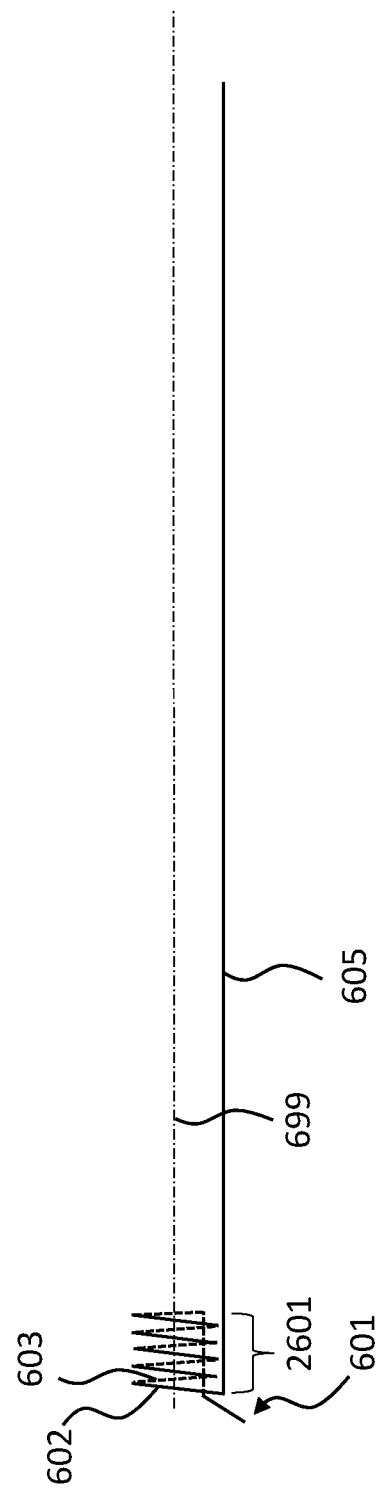

FIG. 10 keys off the embodiment of FIG. 7, where, because the wire was wound in the backwards direction, the subsection 605 that extends from the first location to the second location remote from the first location extends over the windings (i.e., on the outside, as opposed to the windings extending over the subsection 605. It is noted that while the embodiment of FIG. 10 depicts the subsection 605 extending in a straight line, in some embodiments, a high pitch winding can be utilized to reach the second section from the first section. Still further, in an exemplary embodiment, a low pitch winding can be utilized to wind over the first layer of winding so as to establish a two layer winding. Alternatively, in an exemplary embodiment, a winding can be utilized that has a pitch such that the wire falls within the spaces left by the winding of the first layer. In any event, irrespective of how the wire is moved forward (from the left to the right), the subsection 605 extends to the second location.

Figure 11:
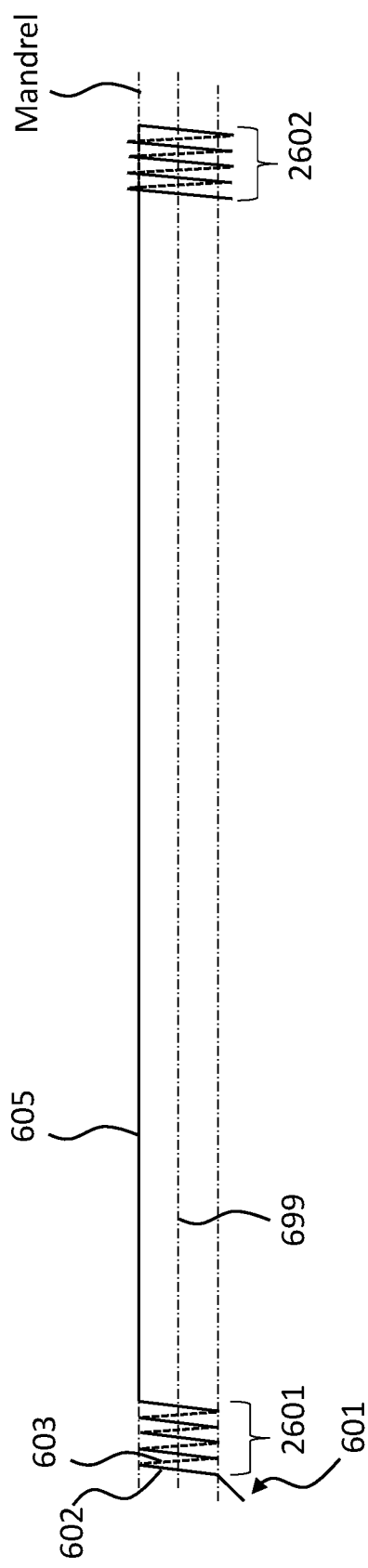
Figure 12:
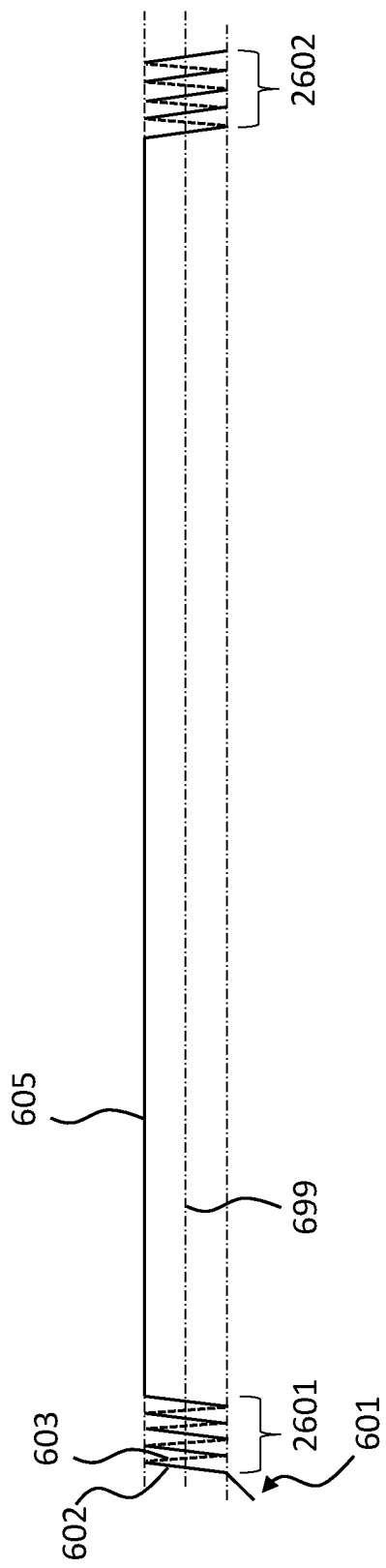

FIG. 11 keys off the embodiment of FIG. 6, where, at the second location, wire is wound such that the wire is bunched at the second location. In this embodiment, the wire is extended to the rightmost portion, and the wire is then wound to the left direction over the portion represented by the dashed line. FIG. 12 also keys off the embodiment of FIG. 6, but, as different from FIG. 11, upon reaching the second location, the winding begins so as to establish a second bunch section that extends from the first subsection 605. In this exemplary embodiment, to bring the wire back towards the right, the wire is then wound over the first wound section at the first location, which, in some embodiments, establishes a multilayer winding, while, in other embodiments, the wire is wound in between the previous windings so that there is only a single layer.

It is briefly noted that in at least some exemplary embodiments, the direction of winding always remains the same (e.g., looking down the longitudinal axis 699 from the right (towards the left), counter clock-wise for both winding actions at a given location (and for the entire device, for that matter)), while in some embodiments, the direction of winding can be different (e.g., again, looking as just detailed, counter clockwise for the first winding action and clockwise for the second (when the wire is laid towards the first section)). Any arrangement of winding that can be utilized to implement the teachings detailed herein can be utilized in some exemplary embodiments (all directions the same, directions on one end of the array the same with the direction different on the other end, etc.).

Figure 13:
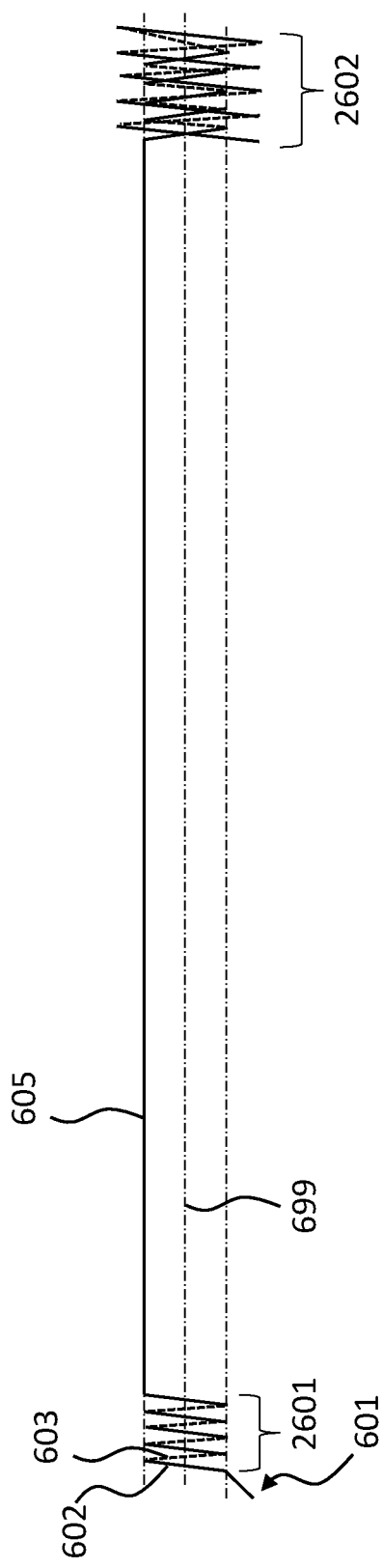

FIG. 13 depicts an exemplary embodiment where the wire is extended back towards the first location by winding over top of the first winding at the second location. It is briefly noted that in the schematic of FIG. 13, as well as the schematics of some of the other figure detailed herein, the windings/wire representations are presented in an exaggerated manner so that the features thereof can be more easily recognized. In this regard, FIG. 13 depicts the winding back to the left as being relatively much larger than the winding below that winding and certainly offsets and above the underlying winding. This is presented only to show that there is a second, higher level of winding here.

Figure 14:
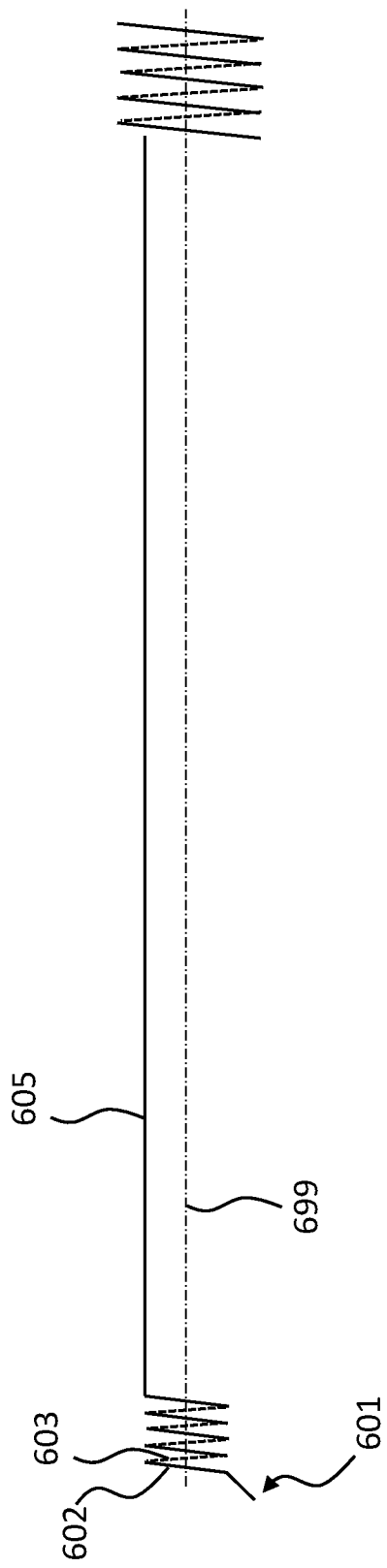
Figure 15:
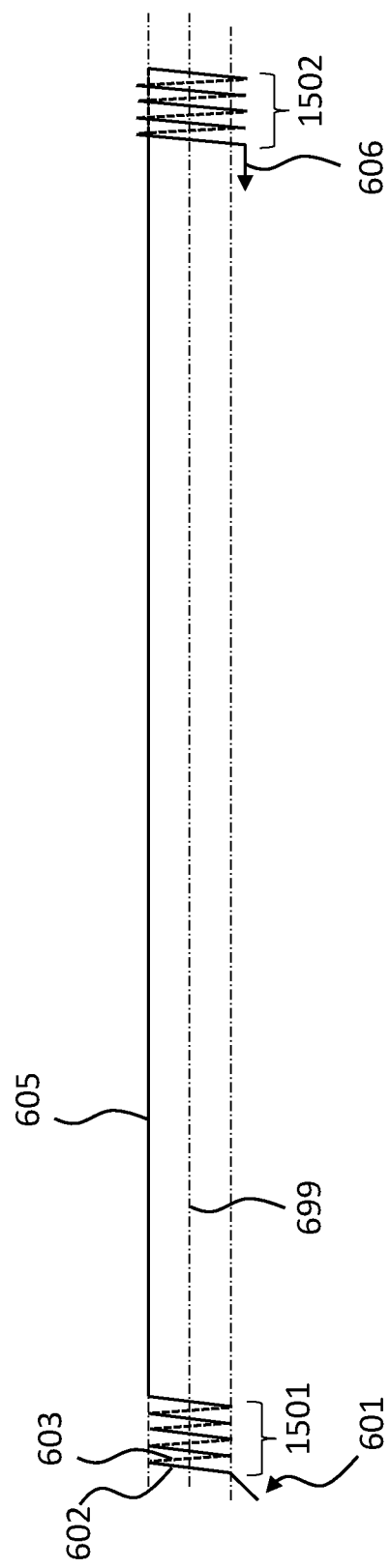

FIG. 14 depicts the embodiment of FIG. 13, except that the first winding at the second location is removed for clarity. The embodiment of FIG. 13 depicts a dense-pack winding on the first layer and the second layer, where the windings establish two separate layers at the second location. That said, in an exemplary embodiment, the windings can be such that there is only one layer as noted above. Irrespective of how the wire is moved from the right to the left, in an exemplary embodiment, the wire is then extended back towards the first location. FIG. 15 keys off the embodiment of FIG. 11, and depicts a wire section 606 extending from the right to the left from the second section towards the first section, whereas FIG. 16 keys off the embodiment of FIG. 13, and also depicts a wire section 606 extending from the right to the left from the second section towards the first section.

Figure 17:
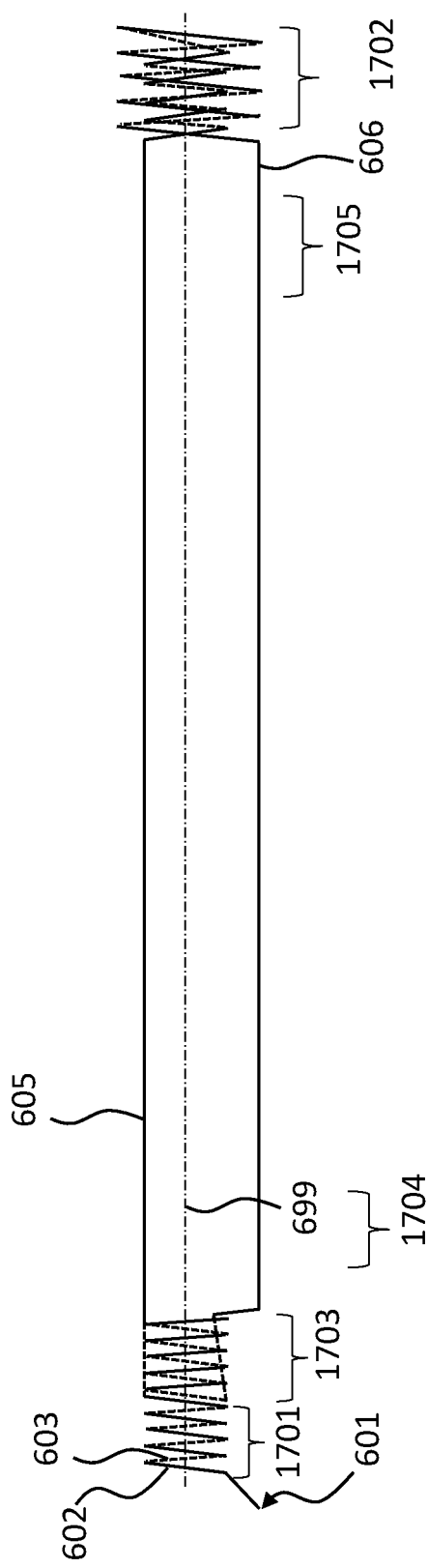

FIG. 17, which keys off FIG. 13, depicts the subsection 606 extending all the way from the second location where the wires are bunched on the right-hand side to a location that is proximate to the first location where the wires are bunched on the left-hand side. In this embodiment, the wires are then wound from left to right as shown in a manner concomitant with the winding at the first location. In this regard, the wire is extended from the second location all the way to the first location, and then the windings at this third location extend about the wire, as represented by the dashed oblique line. Indeed, in this embodiment, this third winding at the third location extends about the wire extensions twice: it extends about the wire that extended from the first location to the second location, and also it extends about the wire that extends from the second location back towards the first location to begin the third location. It is noted that while this embodiment depicts a composite embryonic array vis-à-vis the layered windings, where the winding at the right side is a two layered winding while the winding at the left side is only a single layered winding, in an alternate embodiment, the windings on both sides can be multilayered. By way of example, in an exemplary embodiment, such as where instead of FIG. 17 keying off FIG. 13, FIG. 17 keys off FIG. 10, but FIG. 10 instead includes a two layered winding (not shown in FIG. 10, but can be achieved by winding 605 over top of the initial winding), and in FIG. 17, winding begins at the right side of the third section as opposed to the left side of the third section, and the winding is wound to the right until reaching a location proximate the first location, and then the winding is then wound from the left to the right over top of the winding, so as to achieve a multilayered winding at the first and third locations.

Figure 18:
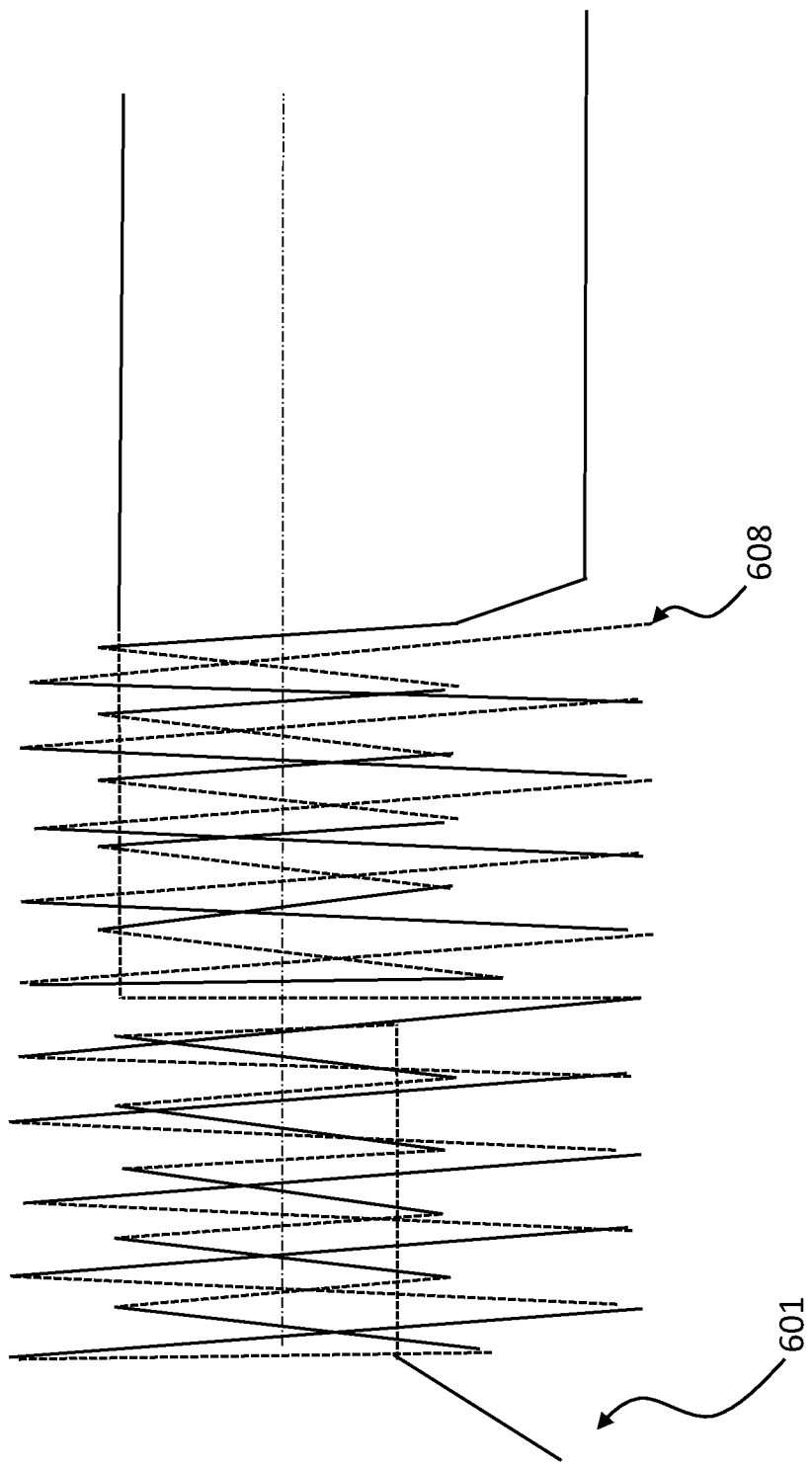
FIGS. 18 and 19 depict close-up views of some exemplary bunchings according to some exemplary embodiments.
Figure 19:
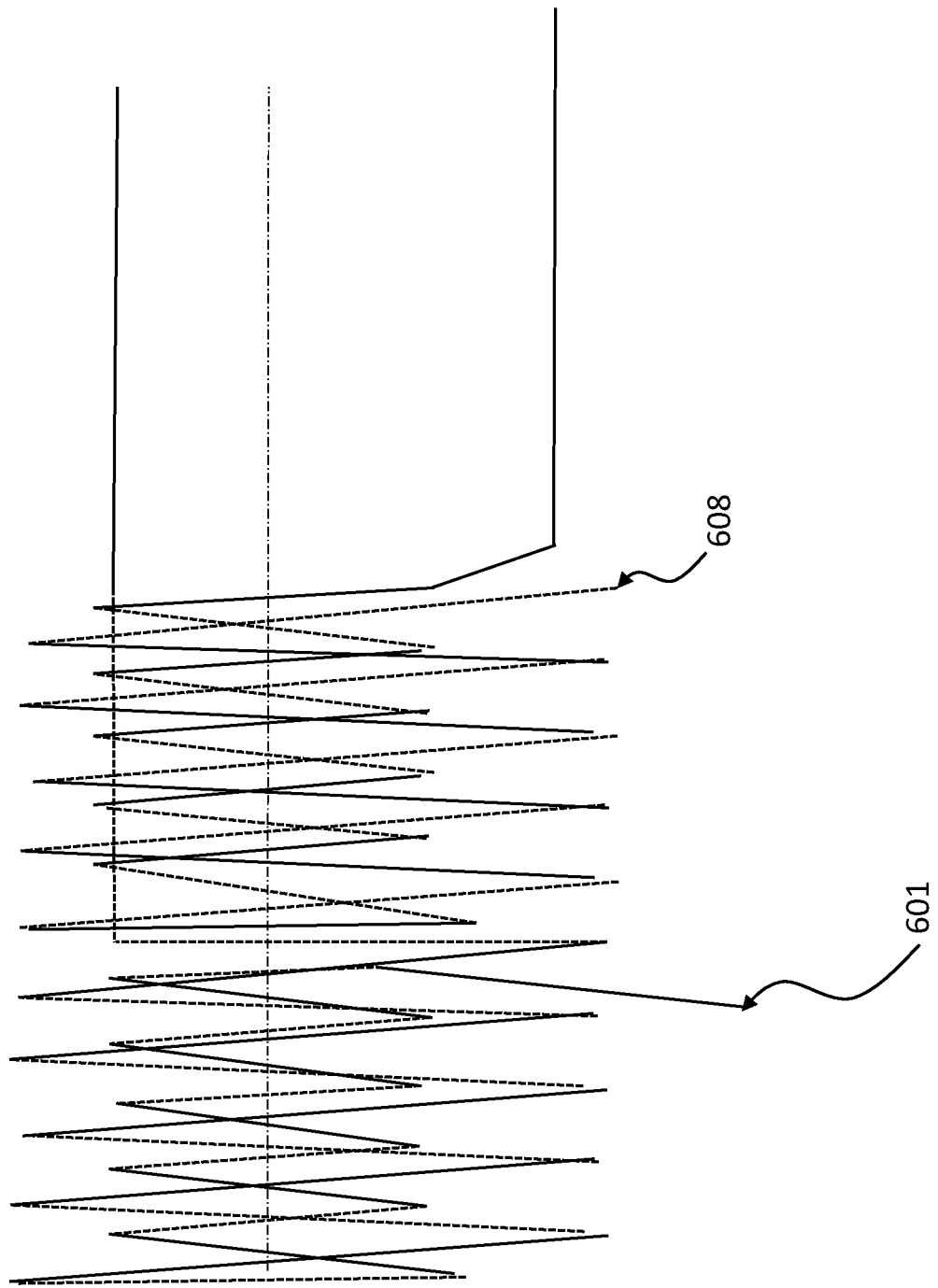

FIG. 18 depicts an exploded view of a combined first and third locations (the first and third locations are contiguous with each other) having the multilayered windings. It is also noted that while the embodiment of FIG. 18 depicts the beginning of the wire at 601, the beginning of the wire can instead begin at the beginning of the very first winding, in some embodiments. That is, in an exemplary embodiment, an embodiment can correspond to FIG. 19. Both FIGS. 18 and 19 depict the end of the wire 608, at least the end of the wire with respect to the end of the windings at the third location. As will be detailed below, in an exemplary embodiment, the wire is then extended to the right again to establish more bunchings.

Figure 20:
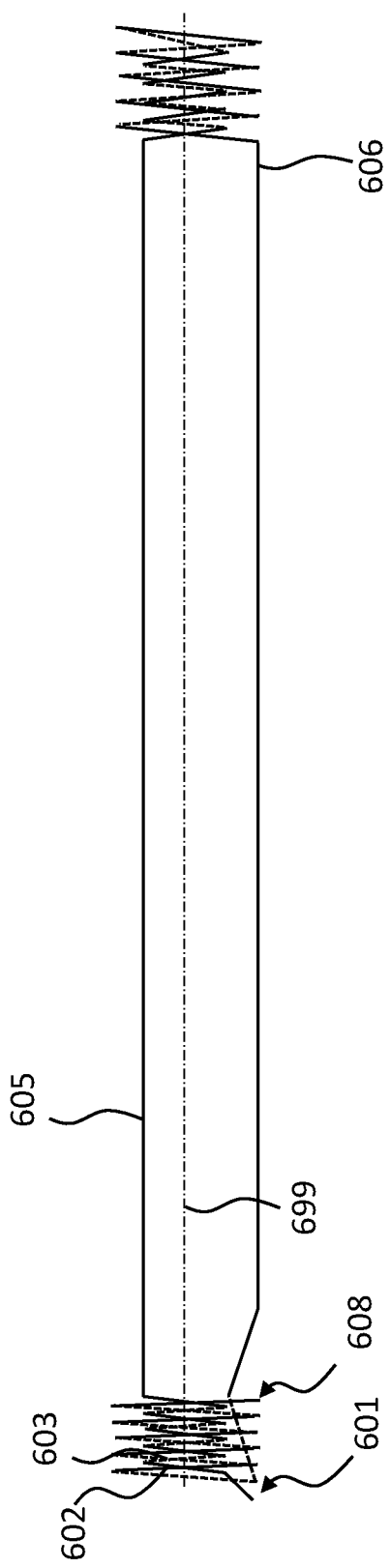

FIG. 20 depicts an alternate exemplary embodiment where section 606 is extended all the way back to the first section and over the first section/over the windings of the first section, and then the wire is wound over the windings of the first section to establish a second layer over the first layer, or, in an exemplary embodiment, to lay the wire in between the windings that were previously laid down. In any event, as can be seen, the results of the actions to establish the arrangement of FIG. 21 results in an end of the wire 608 as seen. Again, it is noted that the depictions are presented in a manner that improves the understanding thereof, as opposed to the scaled representation. Note also that while the upward and downward movements of the wire are depicted, these are presented in an exaggerated manner. Also, it is noted that in some embodiments, there is a degree of bending about the mandrel with respect to the extension of these wires.

Figure 21:
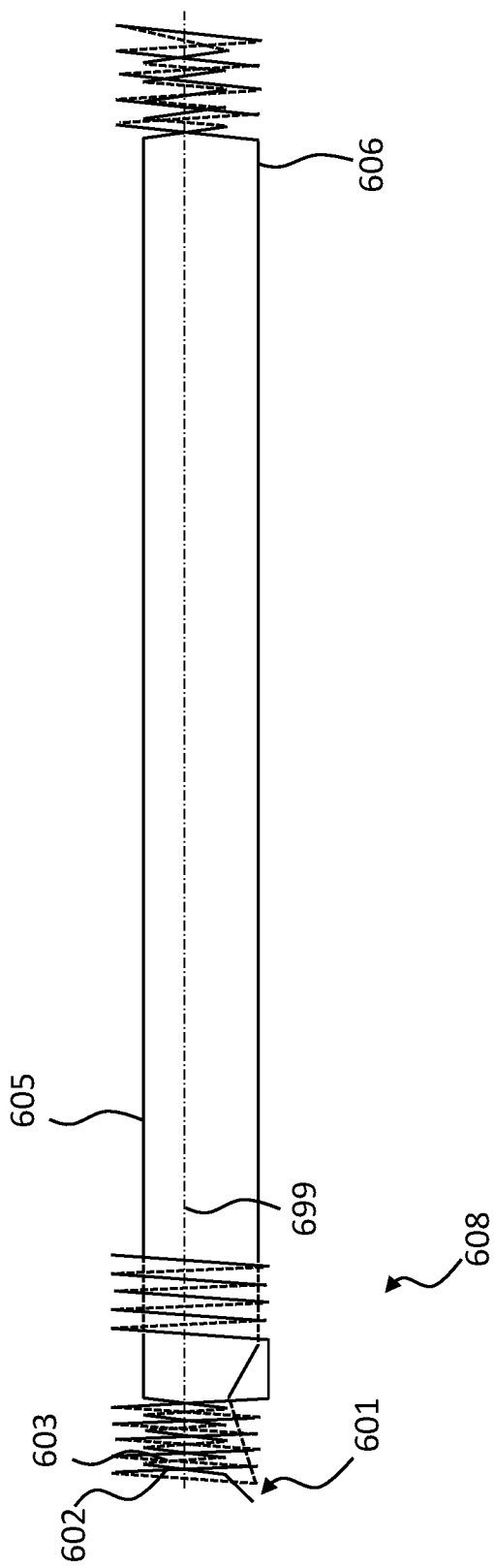
Figure 22:
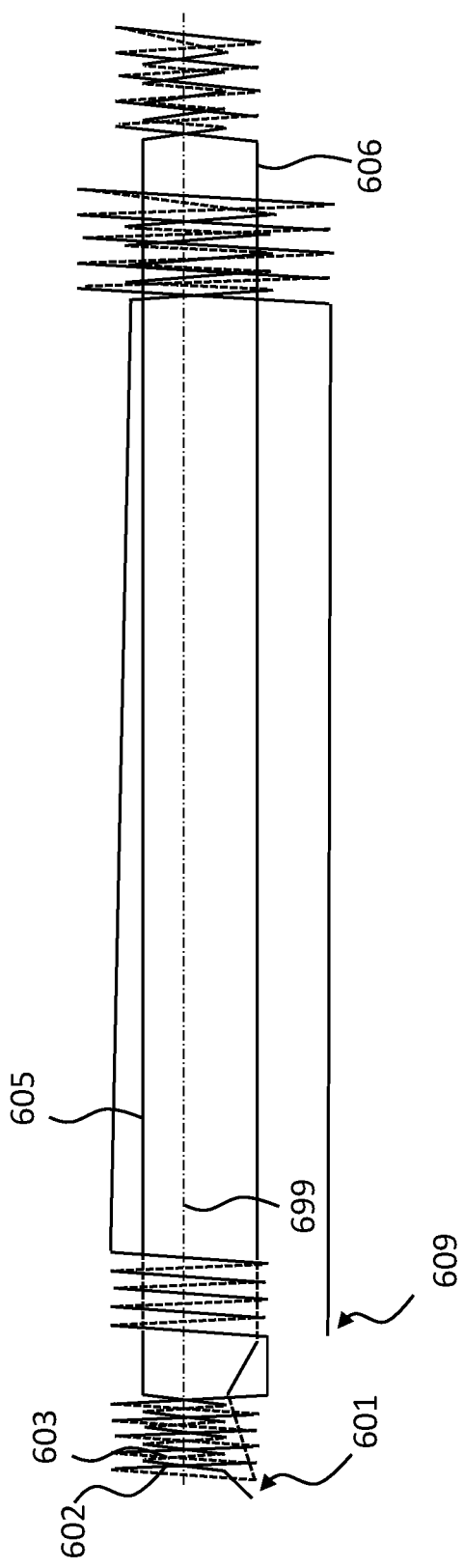

In the embodiment of FIGS. 20 and 17, the wire is now "ready" to be moved to the left to establish an embryonic circuit portion for a second channel. In this regard, FIG. 21 presents the wire being extended from the first location vis-à-vis the embodiment of FIG. 17 where the wire is a double wound wire at the first location owing to the wire being extended from the second location over the windings that were initially layed down at the first location, and then windings being created by winding the wire from the left to the right to establish a second layer in this embodiment, and then moving the wire from those windings towards the left and then winding the wire as shown to establish a new set of windings to establish a bunching at this new location. In an exemplary embodiment, wire is then extended towards the bunching at the right as shown in FIG. 22, and then the wire is wound so as to establish a bunching as shown, which bunching is dual layer consistent with the bunching immediately to the right thereof. FIG. 22 also depicts the wire being extended from the bunching that is second to the right back to the bunching that is second to the left, the wire ending at 609. Again, FIG. 22 depicts exaggerated features of the wire. In real life, the features of the wire will be much less exaggerated, and may not even have the specific features depicted in some drawings.

Figure 23:
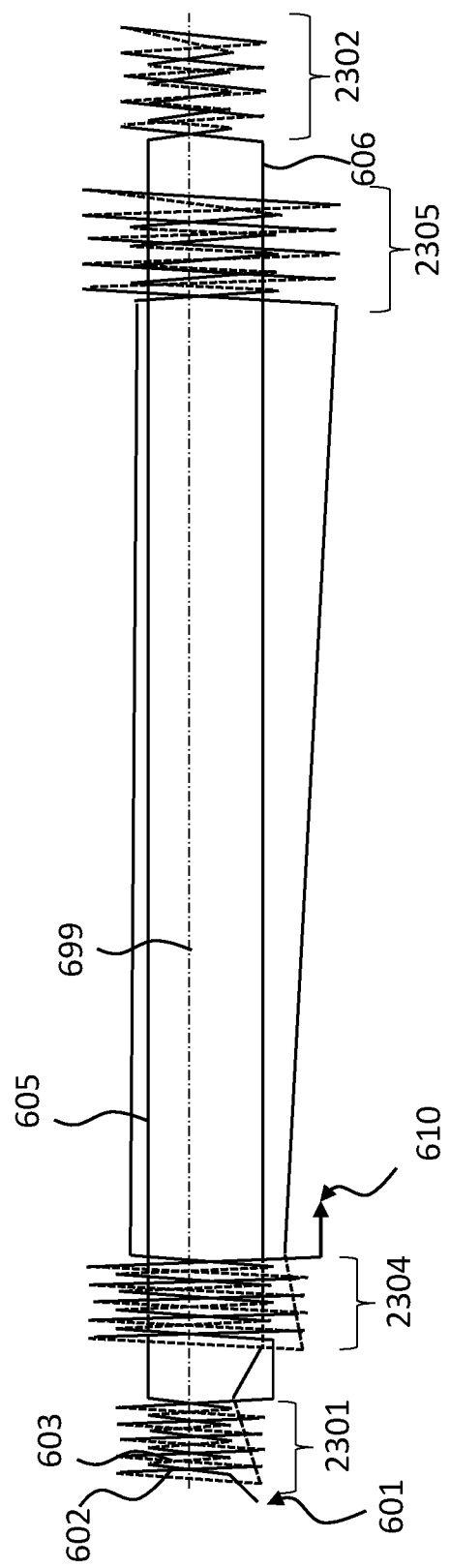

It is to be understood that in an exemplary embodiment, as depicted in FIG. 23, the wire is then wound about the bunching that is second to the left so as to essentially duplicate the bunching that is all the way to the left. Then, if additional channels are desired, the wire is extended to the right to a location proximate the second bunching to the right (e.g., as represented by arrow 610) and then wound in a manner concomitant with the winding proximate thereto to establish a new bunching, and then the wire is brought towards the left and so on.

Figure 24:
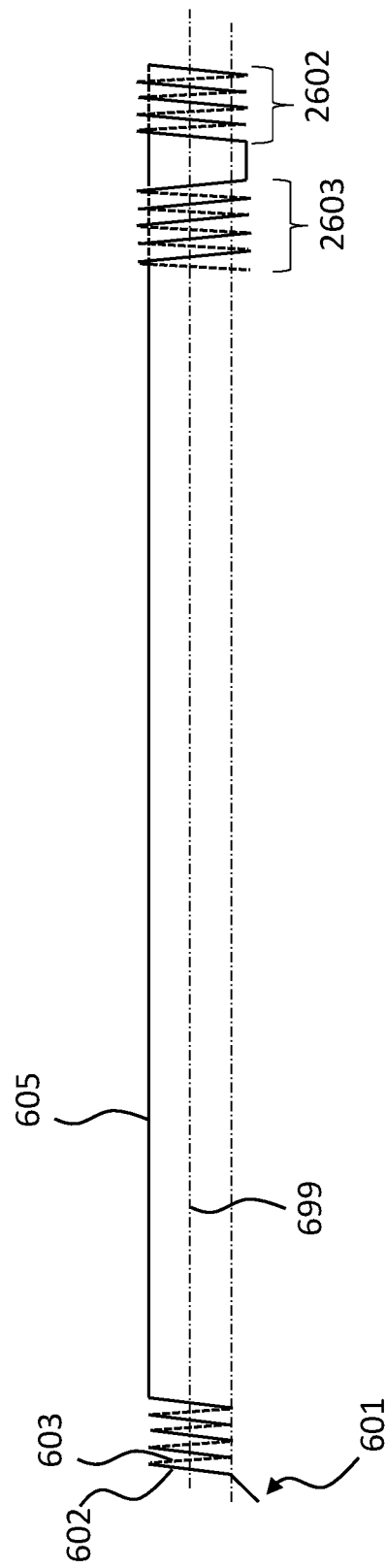
Figure 25:
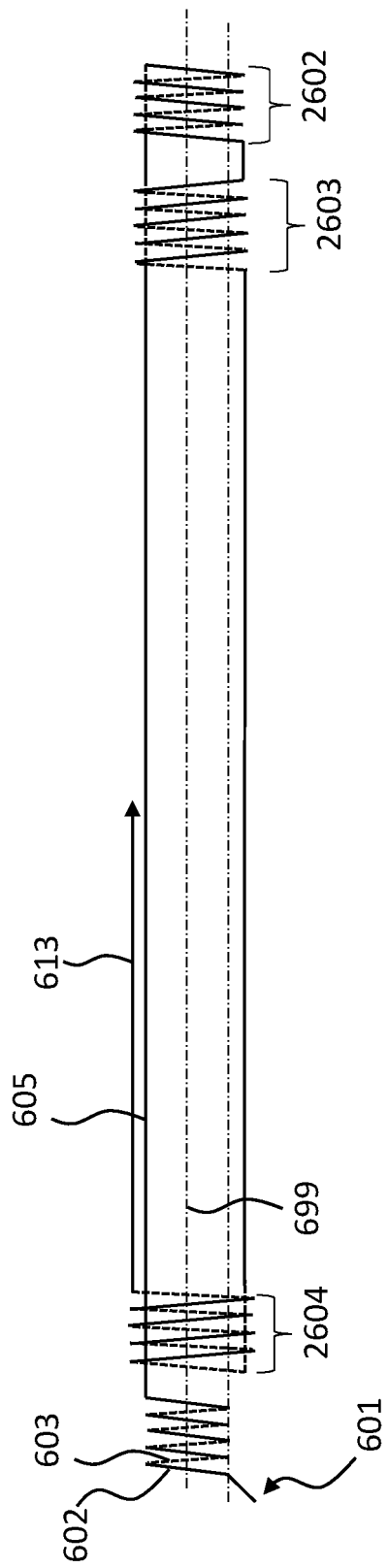

FIG. 24 depicts an exemplary embodiment that keys off the embodiment of FIG. 12, where, after establishing the bunching at the far right, the wire is extended towards the bunching at the far left to a location proximate the bunching at the far right, and then the wire is wound as shown to establish a second bunching at this new location. In an exemplary embodiment, the wire is then extended to the left to a location proximate the bunching at the far left, and the wire is wound to establish a bunching at that location, as seen in FIG. 25. FIG. 25 also shows the wire being extended to the right again, to establish another bunching proximate the second bunching to the right.

Figure 26:
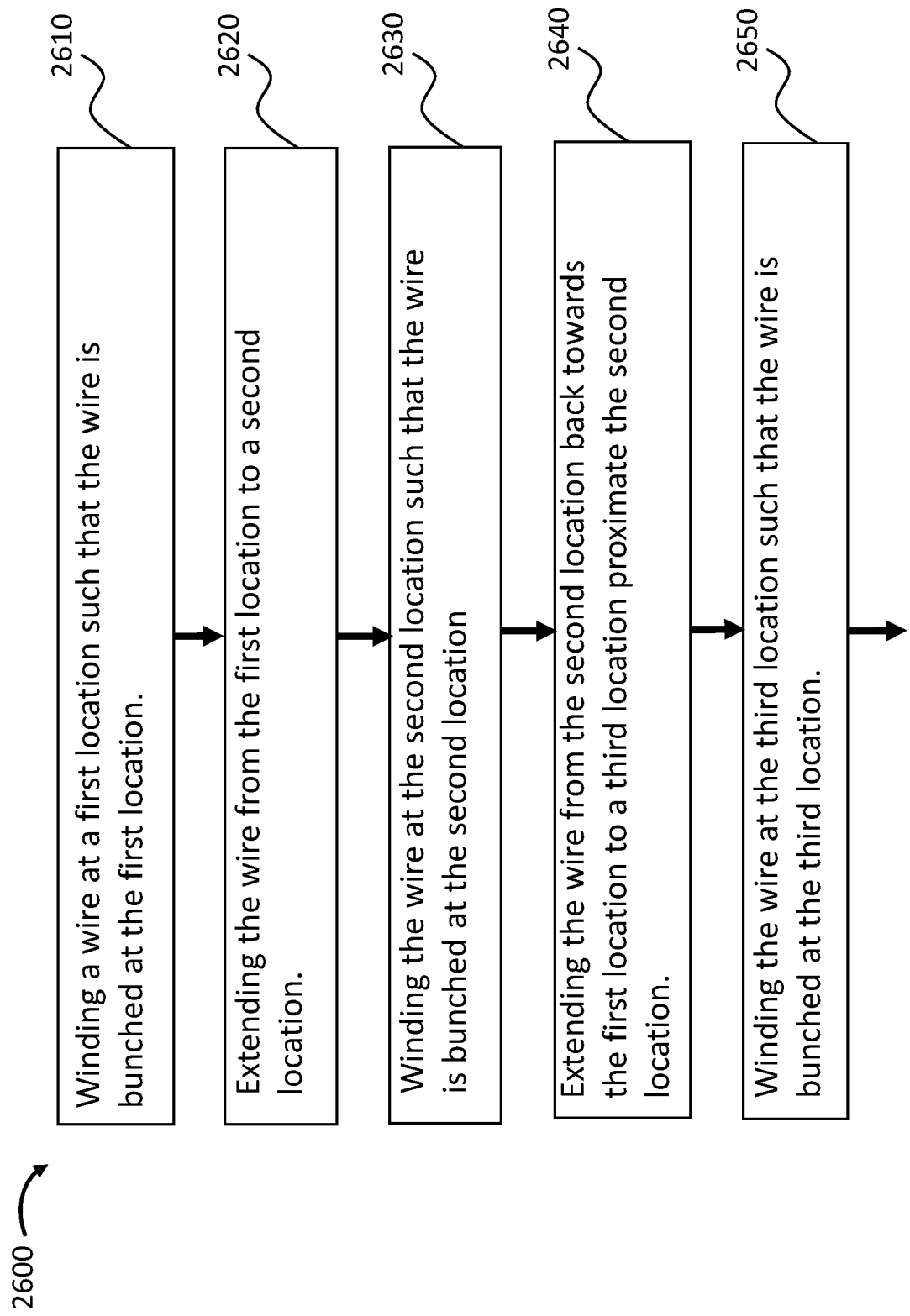
FIGS. 26 and 27 present an exemplary flowchart according to an exemplary method.
Figure 27:
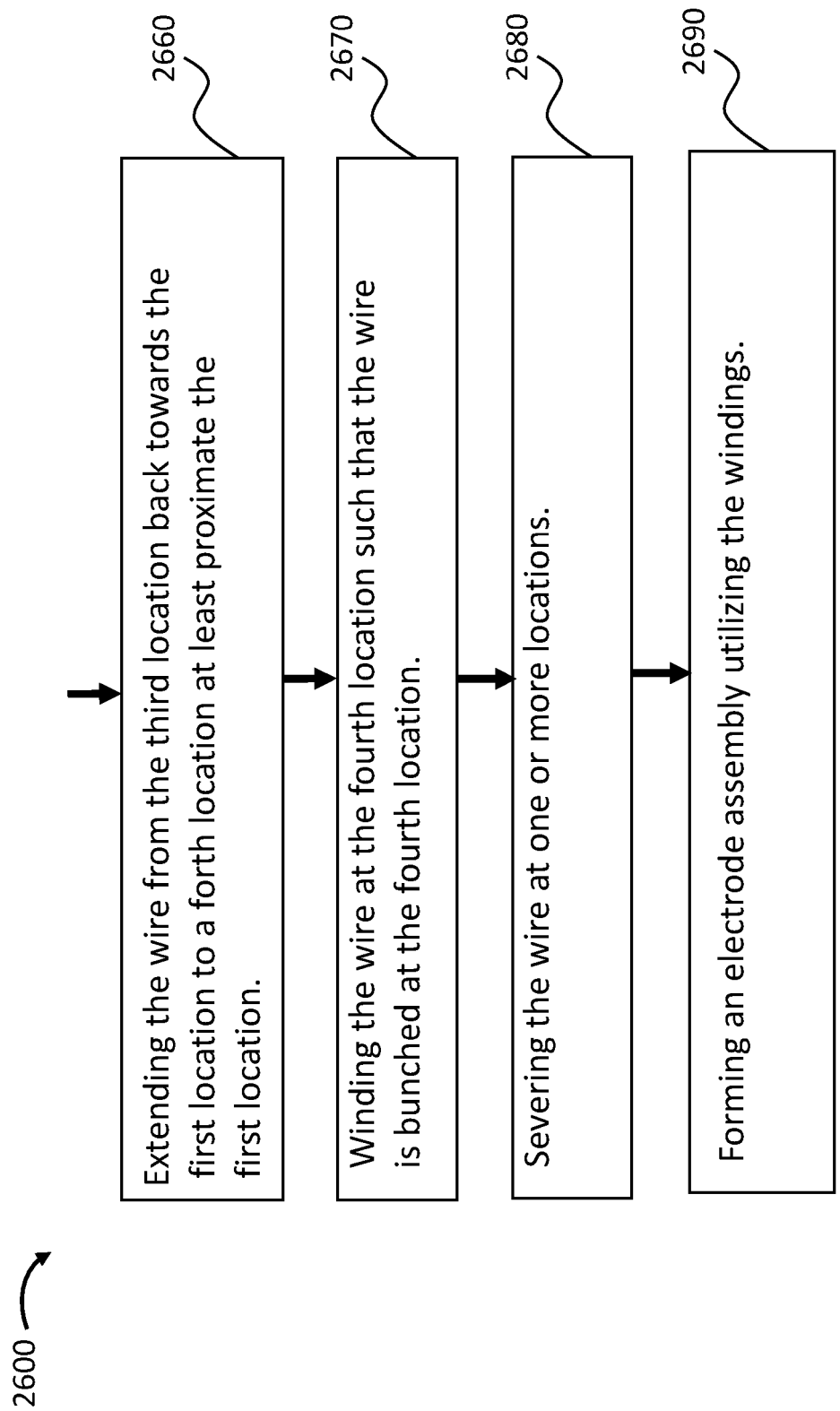

In view of the above, it can be seen that in an exemplary embodiment, there is a method of making an electrode array. In this regard, FIGS. 26 and 27 present an exemplary flowchart for an exemplary method, method 2600. Method 2600 includes method action 2610, which includes winding a wire at a first location such that the wire is bunched at the first location. In the figures above, the first location can correspond to the location 2601. In an exemplary embodiment, method action 2610 is preceded by the action of obtaining a wire and/or establishing a mandrel. In an exemplary embodiment, method 2600 is executed utilizing an automated device that has a wire feeder that feeds the wire about a mandrel as the mandrel spins around in a repeating manner. In an alternative embodiment, the wire is wound about a stationary mandrel (or a moving mandrel) by moving a nozzle out of which the wire is driven. Any device, system, and/or method that can enable the implementations of the methods detailed herein and/or to establish the apparatuses detailed herein can be utilized in at least some exemplary embodiments. In an exemplary embodiment, the wire can be wound by hand.

Method 2600 further includes method action 2620 which includes extending the wire from the first location to a second location. In an exemplary embodiment, this corresponds to extending the wire to have the subsection 605 in FIG. 8 or to have the subsection 605 in FIG. 9. In an exemplary embodiment, this extension can have a sub subsection that is straight as well as a sub subsection that is wound, and maybe another sub subsection that is straight, and maybe another sub subsection that is wound and so on. In any event, FIGS. 11, 12, and 13 depict an exemplary location of the second location 2602. Note that location 2602 extends as indicated from the left side of the indicator all the way to the right side of the indicator. Thus, in the embodiment of FIG. 11, the wire extends in a non-wound manner in the second location. Conversely, in the embodiment of FIG. 12, the wire is always wound in the second location. Note that in some embodiments, a portion of the wire can be wound and a portion of the wire may not be wound in that second location, or a plurality of portions may be wound and/or plurality of portions may not be wound in that second location.

Method 2600 further includes method action 2630, which includes winding the wire at the second location such that the wire is bunched at the second location. Any manner of winding and/or bunching the wire at the second location can be practiced, providing that such enable the teachings detailed herein. This is also the case with respect to the first location, and any other location detailed herein or otherwise that would exist when implementing some of the teachings with respect to an array that has a plurality of channels.

Method 2600 further includes method action 2640, which includes extending the wire from the second location back towards the first location 2601 to a third location proximate the second location. This is represented by FIG. 15 and FIG. 16, and FIG. 24 and FIG. 25, vis-à-vis section 2603. Method 2600 further includes method action 2650, which includes winding the wire at the third location 2603 such that the wire is bunched at the third location. This is seen in FIGS. 24 and 25. As can be seen, the second and third locations are proximate one another. Also, in this embodiment, the second location and the third location are separated by distance from each other. In an alternative embodiment, the locations can be proximate one another and in contact with one another. Still, in this embodiment, the locations are spaced away from one another by a distance, which distance will correspond to or otherwise be associated with a distance that is desired between one stimulating electrode and an adjacent another stimulating electrode of the final electrode array.

Method 2600 further includes method action 2660, which includes extending the wire from the third location back towards the first location to a fourth location 2604 at least proximate the first location 2601. Method 2600 also includes method action 2670, which includes winding the wire at the fourth location such that the wire is bunched at the fourth location. This is seen in FIG. 25.

It is noted that in this exemplary embodiment, the wire is contiguous from the first location to the fourth location. That is, a single wire that is unbroken extends from the first location to the fourth location. Indeed, in this embodiment, a single wire extends from the beginning of the winding that is established at the first location all the way to the end of the winding that is established at the fourth location. Thus, in an exemplary embodiment, there is a plurality of windings and associated electrical connections that are established by a monolithic conductor component (e.g., a platinum base wire) and a monolithic electrical insulator component (e.g., the insulator material cladding the base wire). That said, in an alternate exemplary embodiment of method 2600, the wire does not extend continuously from the first location of the fourth location. In this regard, in an exemplary embodiment, after one or more of the aforementioned winding actions, the wire can be caught, and then the wire can then be extended to the next winding location, where the wire is wound and then the wire is cut, and then extended to the next winding location, and so on. In such an embodiment, after method action 2670, the wire would not be contiguously extending from the first location of the fourth location.

Still, in the embodiment where the wire does so contiguously extend from the first location of the fourth location, in an exemplary method, method 2600 further includes method action 2680, which includes severing the wire at one or more locations. In this embodiment, where the wire contiguously extends from the first to the fourth location, method action 2680 must be executed at least after method action 2660, and, in some embodiments, after method action 2670. This is opposed to the embodiment where the wire does not contiguously extend from the first location to the fourth location, where method action 2680 can be executed prior to method action 2660.

Method 2600 further includes method action 2690, which includes forming an electrode assembly utilizing the windings established in the preceding method actions. In an exemplary embodiment, this includes forming a silicon carrier about the windings. In an exemplary embodiment, the windings are placed into a mold (prior to or after method action 2680) and silicone is molded about the windings (again, prior to or after method action 2680, depending on the embodiment). The silicon establishes a carrier to carry the windings and otherwise maintain the windings at a spatial distance from each other. It is to be understood that in at least some exemplary embodiments, there are additional actions associated with method action 2690, some of which are described below.

Figure 28:
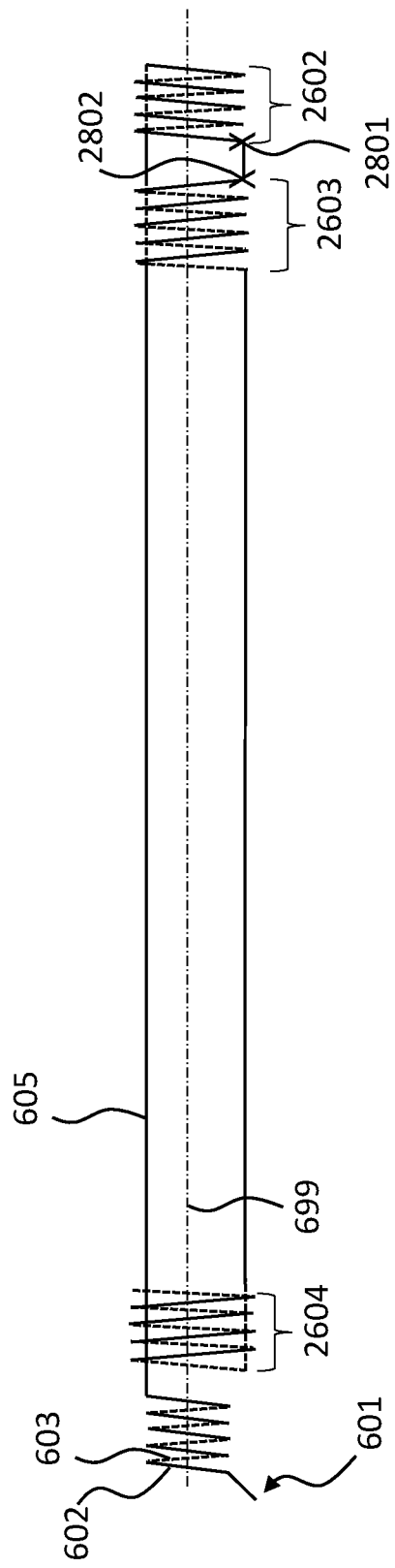
FIGS. 28-32 and 39 variously depict embryonic electrical systems of exemplary electrode arrays and otherwise pictorially depict actions/sub actions exemplary methods of making the embryonic electrical systems according to some embodiments.
Figure 29:
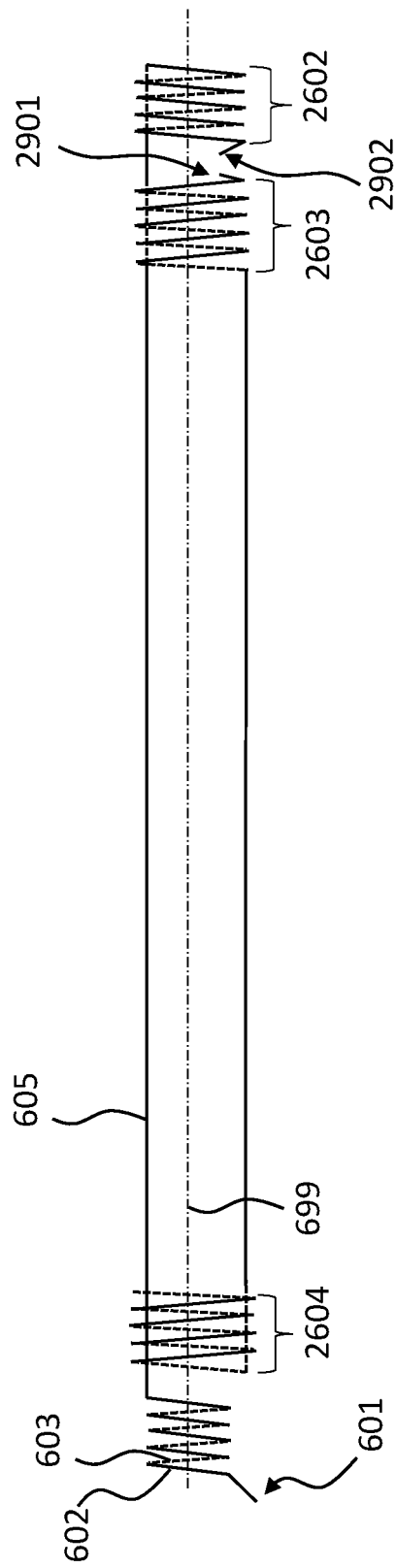

With respect to method action 2680, in an exemplary embodiment, the wire is severed at the locations indicated in FIG. 28 (at the Xs indicated by 2801, 2802). It is noted that instead of two severings between location 2602 and 2603, one severing can be executed. Two severings are indicated so as to eliminate any sections of wire that extend away from the windings. FIG. 29 depicts the results of the severing, where only one severing is executed between location 2602 and 2603, and the wire is pulled inward and/or pushed inward so that the ends do not stick outward. Thus, as can be seen in FIG. 29, there are ends 2901 and 2902 in between the bunchings on the right, which ends are parts of wire subsections that have been pushed inward so as to not contact or otherwise be less likely to contact tissue of the recipient when the ultimate electrode array is implanted in the recipient.

In view of the above, it can be seen that in an exemplary embodiment, the first and fourth locations are proximate one another and the second and third locations are proximate one another and the third and fourth locations are remote from one another, all with respect to the form electrode array. In this regard, it is to be understood that in at least some exemplary embodiments, embodiments utilize a U-shaped mandrel or a J-shaped mandrel or a bent mandrel (e.g., two or more straight sections obliquely angled relative to one another) where the ends of the U or the J are closer to each other than the ends are to the inflection point. (In an exemplary embodiment, the mandrel can be an L shaped or a mandrel that includes straight components bent relative to one another, etc.). Accordingly, with respect to absolute distance, in an exemplary embodiment, the third and fourth locations can be relatively close to each other, but such are remote with respect to the form electrode array. Of course, in an exemplary embodiment that utilizes a mandrel or mandrel that has a curvature of at most 20°, 30°, 40°, 50°, or 60°, the absolute distance between the third and fourth locations will still be such that they are remote from each other in absolute terms during manufacturing as opposed to relative terms associated with the formed electrode array.

In an exemplary embodiment, respective bunchings establish respected embryonic contacts and respective embryonic electrodes of the electrode array. Additional details of the formation thereof will be described below.

In an exemplary embodiment of method 2600, the wire is extended and wound so that there are at least a first group and a second group of five bunched sections each, two bunched sections of the first group corresponding to the bunchings at the first and fourth locations, and two bunched sections of the second group corresponding to the bunchings at the second and third locations. In this exemplary embodiment, the bunchings of the first group and the second group are made up of the same single wire.

Figure 31:
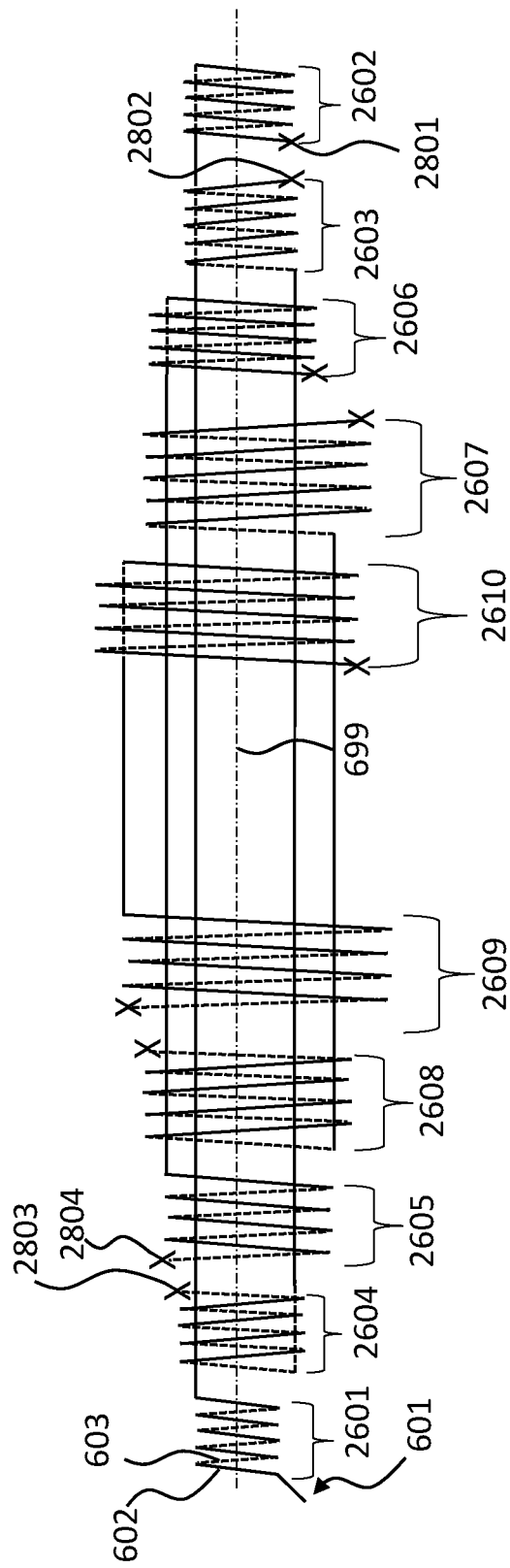

FIG. 31 depicts such an exemplary embodiment of the aforementioned two groups of five bunching's, where locations 2601, 2604, 2605, 2608 and 2609 are the locations of the respective five bunchings of the first group and locations 2602, 2603, 2606, 2607 and 2610 of the locations of the five bunchings of the second group, where the respective locations are in electrical conductivity with each other as can be seen. In the embodiment of FIG. 31, the wire was cut at locations indicated by the "X"s. Locations 2803 and 2804 are enumerated to indicate how, in this embodiment, the wire is severed at the left side of the overall embryonic electrode array between location 2604 and 2605 because in this embodiment, the wire is extended from section 2602 to 2605, and then the bunchings at section 2605 are created, and then the extended from section 2605 to section 2606. Because the bunchings at 2605 are in electrical communication with the bunchings at 2606, but the bunchings that section 2605 are electrically isolated from the bunchings at 2604, the wire is severed in between section 2604 and 2605.

Figure 32:
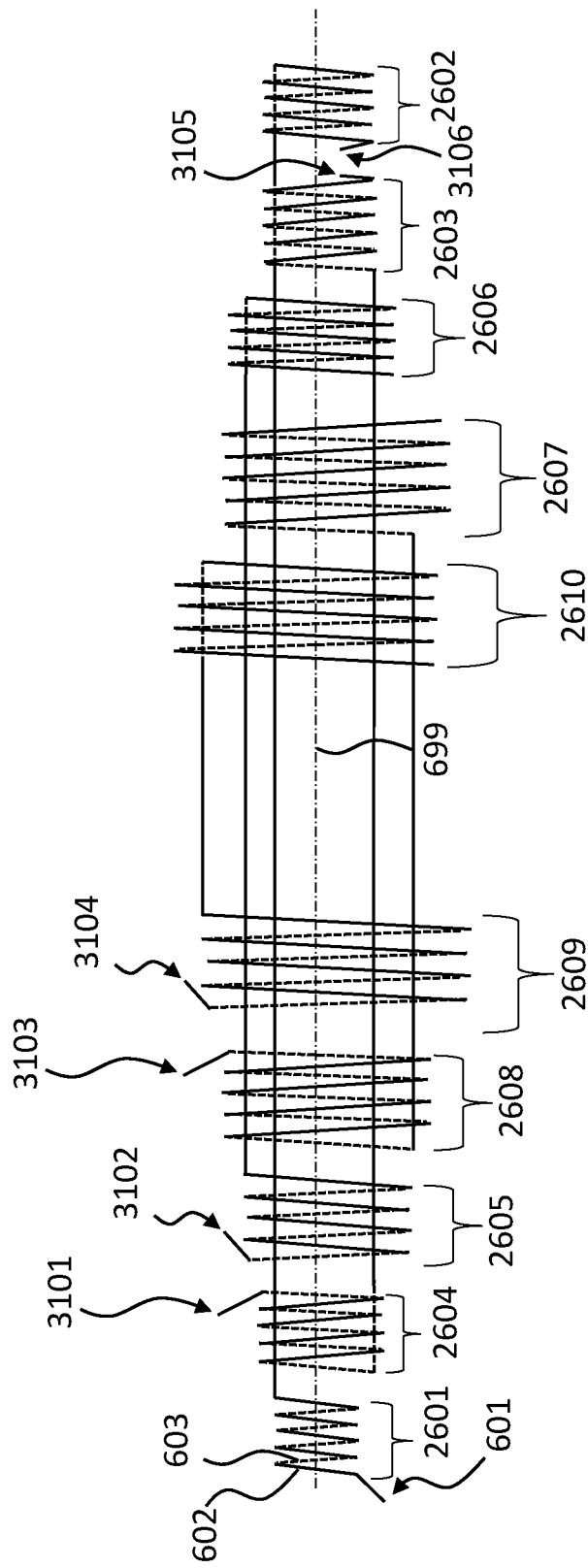

It is noted that in an alternate embodiment, the wire is severed in between location 2604 and 2605 only at one location, and wire subsections extend away, outward, from the bunchings as shown in FIG. 32. In this regard, ends 3101 and 3102 in between the bunchings of sections 2604 and 2605 are shown, where these ends are parts of wire subsections that have been pulled outward, the utility of which will be described in greater detail below. It is noted that in some embodiments, the ends 3101 and 3102 can be pushed inward as well, and in some embodiments, the ends 3105 and 3106 can be pulled inward. In all or in some cases, any of the wires can be severed so that the ends are flush with the windings and/or inboard of the windings (at least the outer diameter thereof) as seen in FIG. 31. FIG. 32 also depicts ends 3103 and 3104. In an exemplary embodiment, ends 601, 3101, 3102, 3103, and 3104 are joined to contact pads. Conversely, in some embodiments, there are no contact pads on the right side of the electrode array, as those are electrodes (hence why, in some embodiments, the wires are cut flush with the windings).

In an exemplary embodiment, the formed electrode assembly is an electrode assembly of a cochlear implant. The extension of the wires between the first group and the second group extend through the portion of the electrode assembly. In an exemplary embodiment, the extensions that extend between the first group and the second group, at least partially, make up the lead assembly 184. In the embodiment of FIG. 31, the resulting lead assembly is a five channel lead assembly of a cochlear implant. It is noted that in an exemplary embodiment, electrode assemblies that have additional channels can be established by following the detailed herein. By way of example only and not by way of limitation, in an exemplary embodiment, the electrode array can be a D channel electrode array, where D is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or more. In an exemplary embodiment, where, with respect to a 22 channel array, and the $22^{nd}$ channel is the most apical, channels 22, 20, 18, 16, 14, 12, 10, 8, 6, 4, and 2 are established by duplicating the windings of location 2601 and 2603 and associated bunchings and extensions therebetween, with ever closer respective bunching locations, and channels 21, 19, 17, 15, 13, 11, 9, 7, 5, 3, and 1 are established by duplicating the windings of locations 2603 and 2604 and the associated bunchings and extensions therebetween with ever closer bunching locations. In accordance with the teachings detailed herein, the channels would be made sequentially starting with channel 22 and working inwards.

It is noted that while the embodiment of FIG. 31 depicts a single layer windings at each of the bunchings locations, in an alternative embodiment, the bunching locations are double layered. Accordingly, in an exemplary embodiment of method 2600, there is the action of winding the wire at the second location such that there are two layers of winding, one over top of the other. It is also noted this can be the case for all or some of the locations of bunching. This can be the case for only the bunchings in the electrode array area, and this can be the case for only some of the bunchings in the electrode array area.

Figure 30:
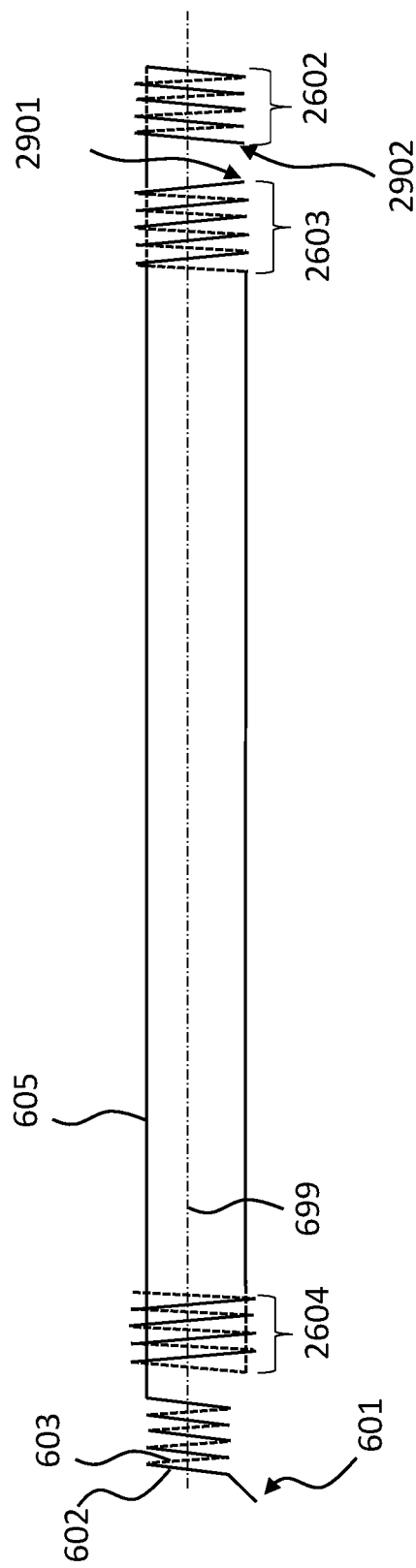
Figure 33:
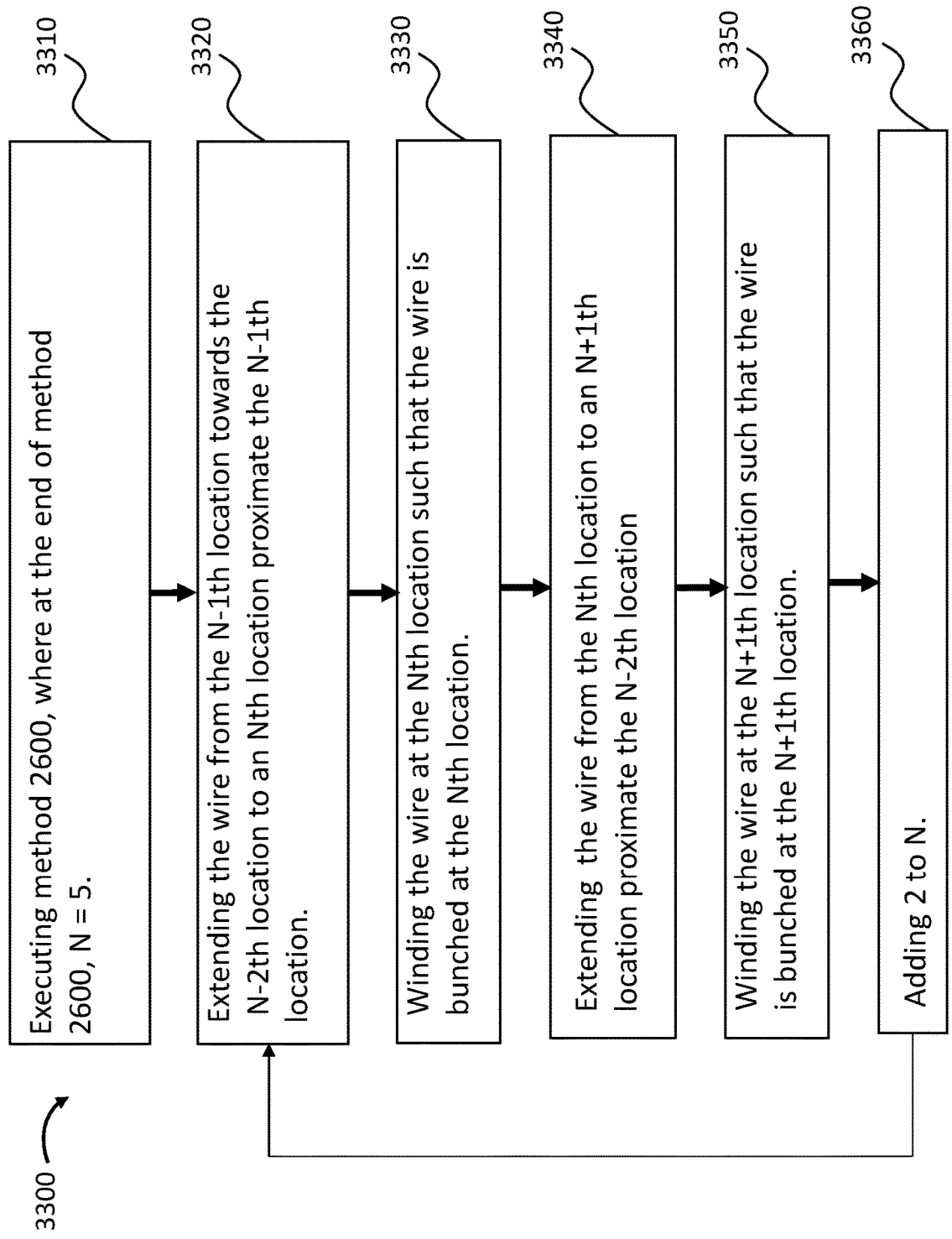
FIGS. 33-36 present an exemplary flowcharts according to some exemplary methods.

In view of the fact that various embodiments are such that varied numbers of channels can be implemented, FIG. 33 provides an exemplary method, method 3300, according to an exemplary embodiment. Method 3300 includes method action 3310, which includes executing method 2600, where at the end of method 2600, a value N is set to five. At the end of method 2600, a two channel embryonic electrode assembly has been established as will be understood. This can correspond to the embodiment of FIG. 30.

Method 3300 further includes method action 3320, which includes extending the wire from the N–1th (i.e., if N=5, $4^{th}$) location towards the N–2th (i.e., if N=5, 3th (or 3rd)) location to an Nth (i.e., if N=5, $5^{th}$) location proximate the N–1th location. In the embodiment of FIG. 31, this corresponds location 2605, where the N–1th location is 2604 and the N–2th location is 2603.

Method 3300 further includes method action 3330, which includes winding the wire at the Nth location such that the wire is bunched at the Nth location. In this regard, still with respect to the embodiment of FIG. 31, this results in the winding at location 2605.

It is briefly noted that while the embodiment of FIG. 31 depicts a space in between location 2604 and 2605, in this embodiment, there need not be a space because method action 3320 only states that the wire is extended from one location to another location. These locations can be located abutting each other. That said, in an exemplary embodiment, method action 3320 is executed such that the wire is extended to create a space between the two locations. This is the embodiment of FIG. 31.

Method 3300 also includes method action 3340, which includes extending the wire from the Nth location to an N+1th (i.e., if N=5, $6^{th}$) location proximate the N–2th location. Method 3300 also includes method action 3350, which includes winding the wire at the N+1th location such that the wire is bunched at the N+1th location. This corresponds to the bunching at location 2606 of FIG. 31. Method 3300 also includes method action 3360, which includes adding 2 to the value of N. at this point, in an exemplary embodiment, if additional channels are desired, the method then returns back to method action 3320, and method action 3320 is executed for now N=7, where previously, N=5. In an exemplary embodiment, where a five channel array is desired, method 3300 is executed until N=11. In an exemplary embodiment, method 3300 is executed for N=5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, or more.

It is to be understood that the various severing implementations detailed herein can be executed in accordance with the various embodiments resulting from the various N values, where one or two or more severings will be located between sections N=$2/3$, $4/5$, $6/7$ $8/9$, $10/11$, $12/13$, $14/15$, $16/17$, $18/19$, $20/21$, $22/23$, $24/25$, $26/27$, $28/29$, $30/31$, $32/33$, $34/35$, $36/37$, and so on.

Figure 34:
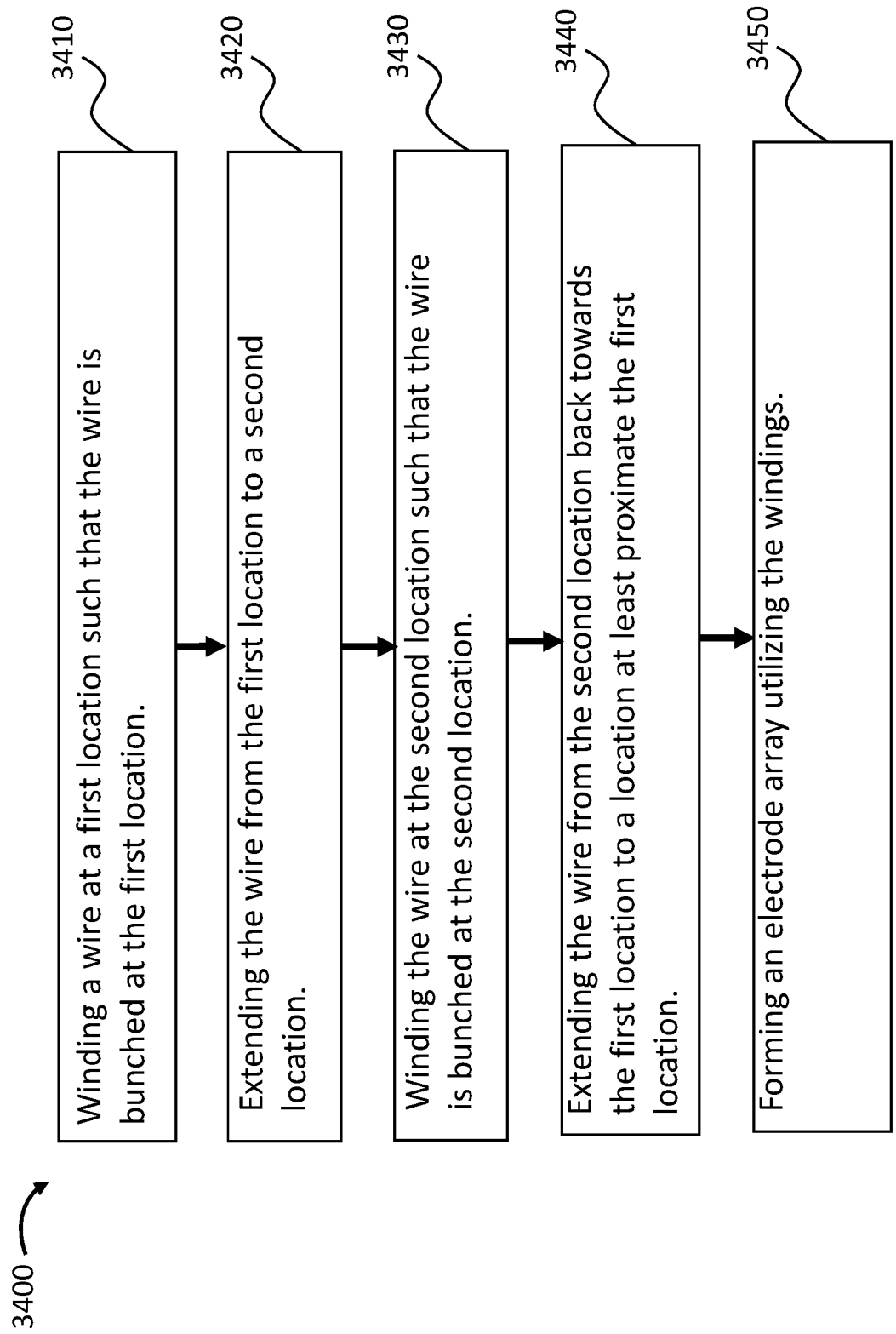

FIG. 34 presents an exemplary algorithm for an exemplary method of making the embodiment of FIGS. 15-23. Method 3400 includes method action 3410, which includes winding a wire at a first location such that the wire is bunched at the first location. In the figures above, the first location can correspond to the location 1501 or 1601 or 2301. In an exemplary embodiment, method action 3410 is preceded by the action of obtaining a wire and/or establishing a mandrel. In an exemplary embodiment, method 3400 is executed utilizing an automated device that has a wire feeder that feeds the wire about a mandrel as the mandrel spins around in a repeating manner. In an alternative embodiment, the wire is wound about a stationary mandrel by moving a nozzle out of which the wire is driven. Any device, system, and/or method that can enable the implementations of the methods detailed herein and/or to establish the apparatuses detailed herein can be utilized in at least some exemplary embodiments. In an exemplary embodiment, the wire can be wound by hand.

Figure 16:
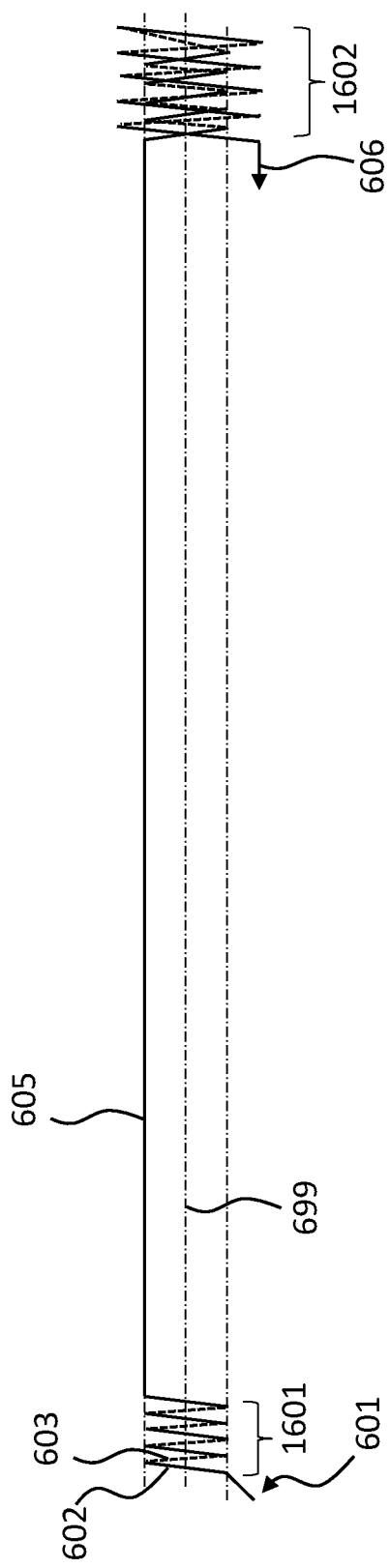

Method 3400 further includes method action 3420 which includes extending the wire from the first location to a second location. In an exemplary embodiment, this corresponds to extending the wire to have the subsection 605 in FIG. 15 or to have the subsection 605 in FIG. 23. In an exemplary embodiment, this extension can have a sub subsection that is straight as well as a sub subsection that is wound, and maybe another sub subsection that is straight, and maybe another sub subsection that is wound and so on. In any event, FIGS. 15, 16, and 23 depict an exemplary location of the second location 1502, 1602, 2302. Note that the second location extends as indicated from the left side of the indicator all the way to the right side of the indicator. Thus, in the embodiment of FIG. 15, a portion of the wire extends in a non-wound manner in the second location, and a portion of the wire extends in a wound manner in the second location. Conversely, in the embodiment of FIG. 16, the wire is always wound in the second location. Note that in some embodiments, a portion of the wire can be wound and a portion of the wire may not be wound in that second location, or a plurality of portions may be wound and/or plurality of portions may not be wound in that second location.

Method 3400 further includes method action 3430, which includes winding the wire at the second location such that the wire is bunched at the second location. Any manner of winding and/or bunching the wire at the second location can be practiced, providing that such enables the teachings detailed herein. This is also the case with respect to the first location, and any other location detailed herein or otherwise that would exist when implementing some of the teachings with respect to an array that has a plurality of channels.

Figure 37:
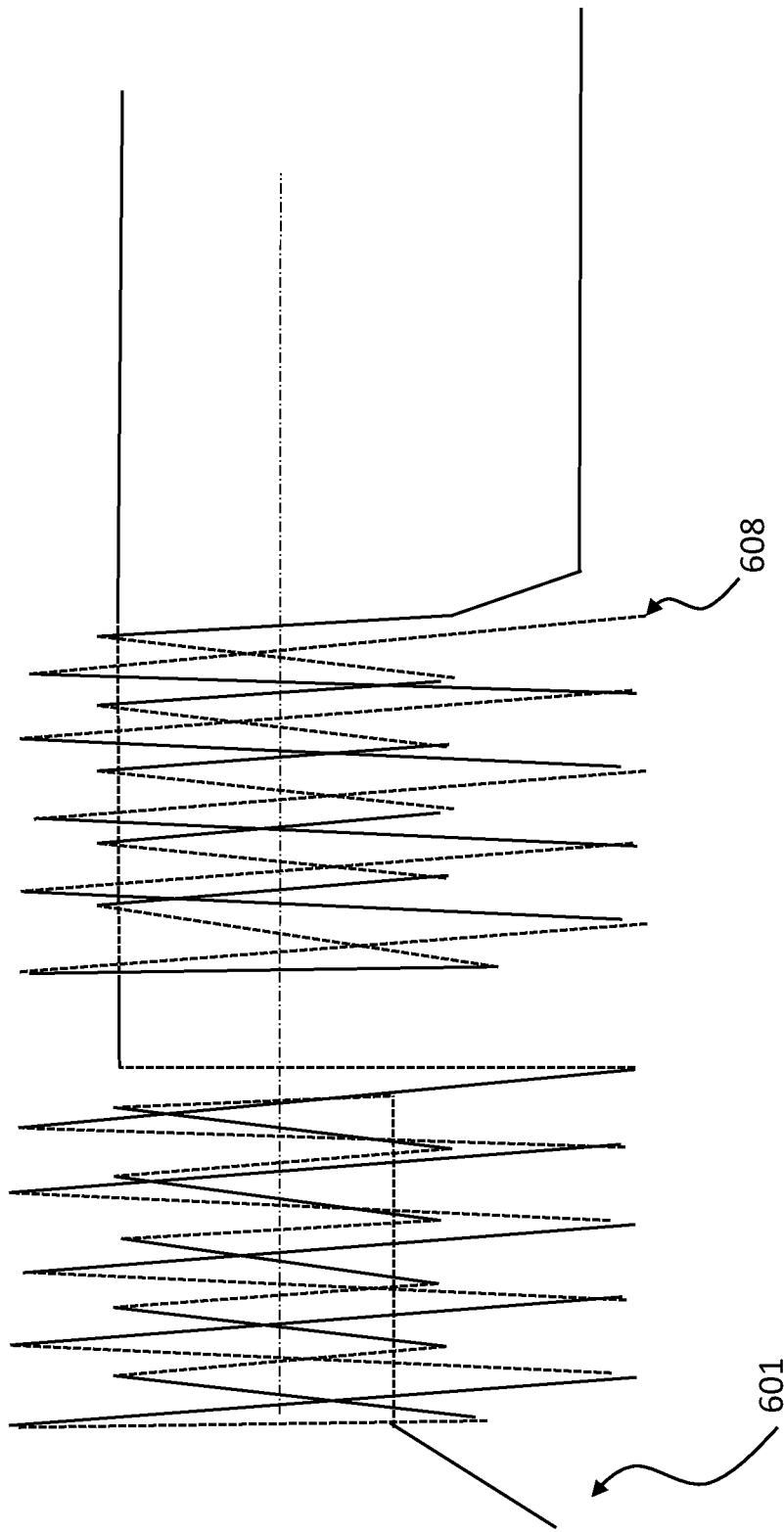
FIGS. 37 add 38 depict close-up views of some exemplary bunchings according to some exemplary embodiments.
Figure 38:
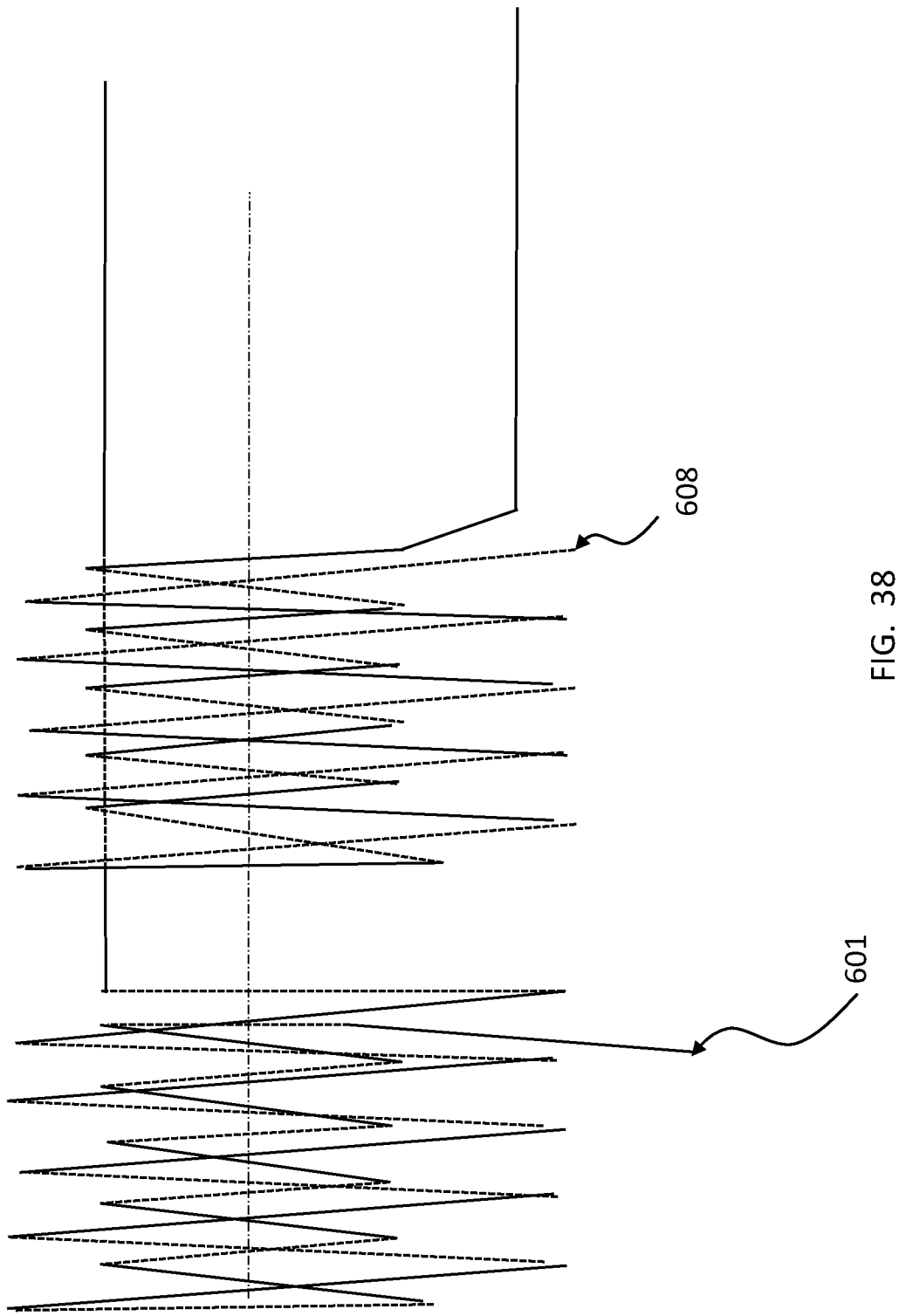

Method 3400 further includes method action 3440, which includes extending the wire from the second location back towards the first location to a location at least proximate the first location. This location can be location 2301, as seen in FIG. 23, where the wire is extended over the winding that was wound in method action 3410 and then wound again thereover. In an alternate embodiment, the at least proximate location can be a third location that abuts the first location, as seen in FIG. 17 (location 1703—which is contiguous with location 1701, which would correspond to the first location of method 3400). Thus, in an exemplary embodiment, method action 3440 can include extending the wire so that the wire overlaps the bunched wire at the first location. Briefly, FIG. 37 is an exploded view of the left side of the embodiment of FIG. 23, and FIG. 38 presents an exemplary embodiment where the winding is started at the right side first, and then wound to the left, and then over the winding again.

It is noted that in this exemplary embodiment, the wire is contiguous from the first location to the location at least proximate the first location. That is, a single wire that is unbroken extends from the first location the at least proximate location. Indeed, in this embodiment, a single wire extends from the beginning of the winding that is established at the first location all the way to the end of the winding that is established at the first location above the first winding. Thus, in an exemplary embodiment, there is a plurality of windings and associated electrical connections that are established by a monolithic conductor component (e.g., a platinum base wire) and a monolithic electrical insulator component (e.g., the insulator material cladding the base wire). That said, in an alternate exemplary embodiment of method 3400, the wire does not extend continuously from the first location of the location at least proximate the first location. In this regard, in an exemplary embodiment, after one or more of the aforementioned winding actions, the wire can be cut, and then the wire can then be extended to the next winding location, where the wire is wound and then the wire is cut, and then extended to the next winding location, and so on. In such an embodiment, the wire would not be contiguously extending from the first location of the fourth location.

Method 3400 further includes method action 3450, which includes forming an electrode assembly utilizing the windings established in the preceding method actions. In an exemplary embodiment, this includes forming a silicon carrier about the windings. In an exemplary embodiment, the windings are placed into a mold (e.g., after method action 3440, and, in some instances, after the wire is severed—more on this below) and silicone is molded about the windings. The silicon establishes a carrier to carry the windings and otherwise maintain the windings at a spatial distance from each other. It is to be understood that in at least some exemplary embodiments, there are additional actions associated with method action 3450, some of which are described below.

Figure 35:
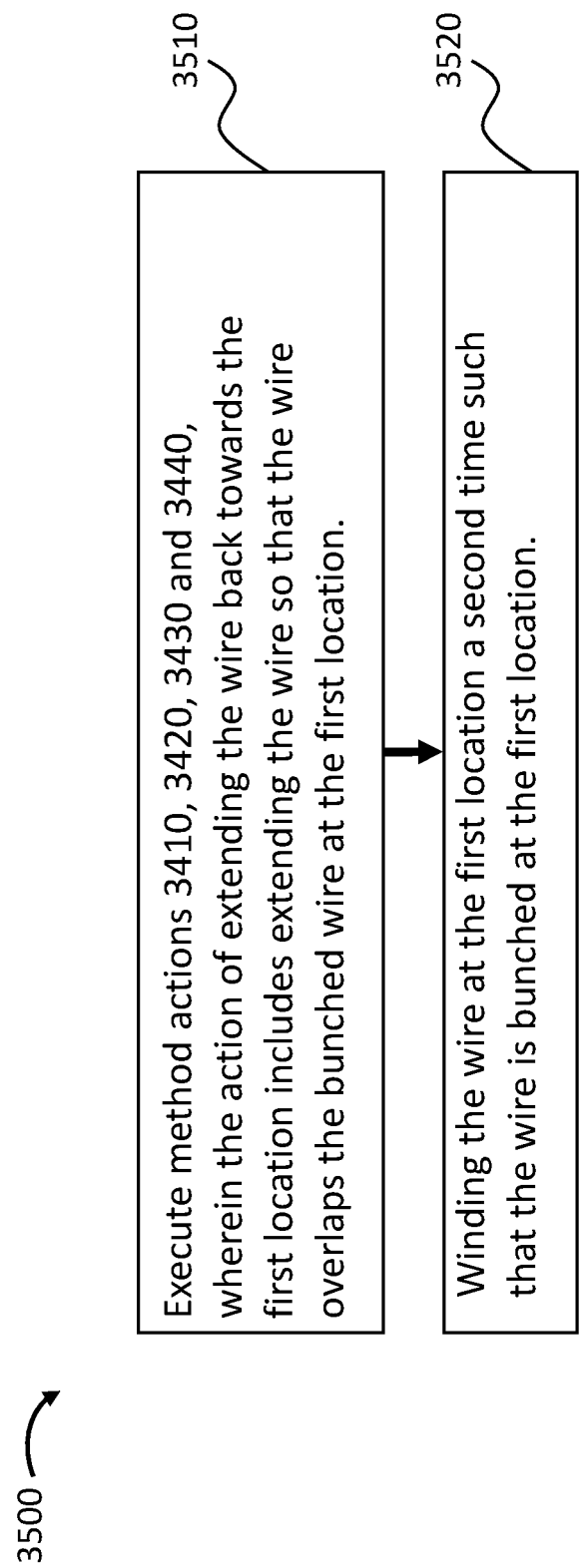

FIG. 35 presents an exemplary flowchart for an exemplary method, method 3500.

Method 3500 includes method action 3510, which includes executing method actions 3410, 3420, 3430, and 3440, wherein the action of extending the wire back towards the first location includes extending the wire so that the wire overlaps the bunched wire at the first location. This can correspond to the embodiment of FIG. 23. Method 3500 further includes method action 3520, which includes winding the wire at the first location a second time such that the wire is bunched at the first location. Again, this can correspond to the embodiment of FIG. 23. Of course, in some embodiments, after method 3520, method 3450 is executed (not shown on flowchart).

Figure 36:
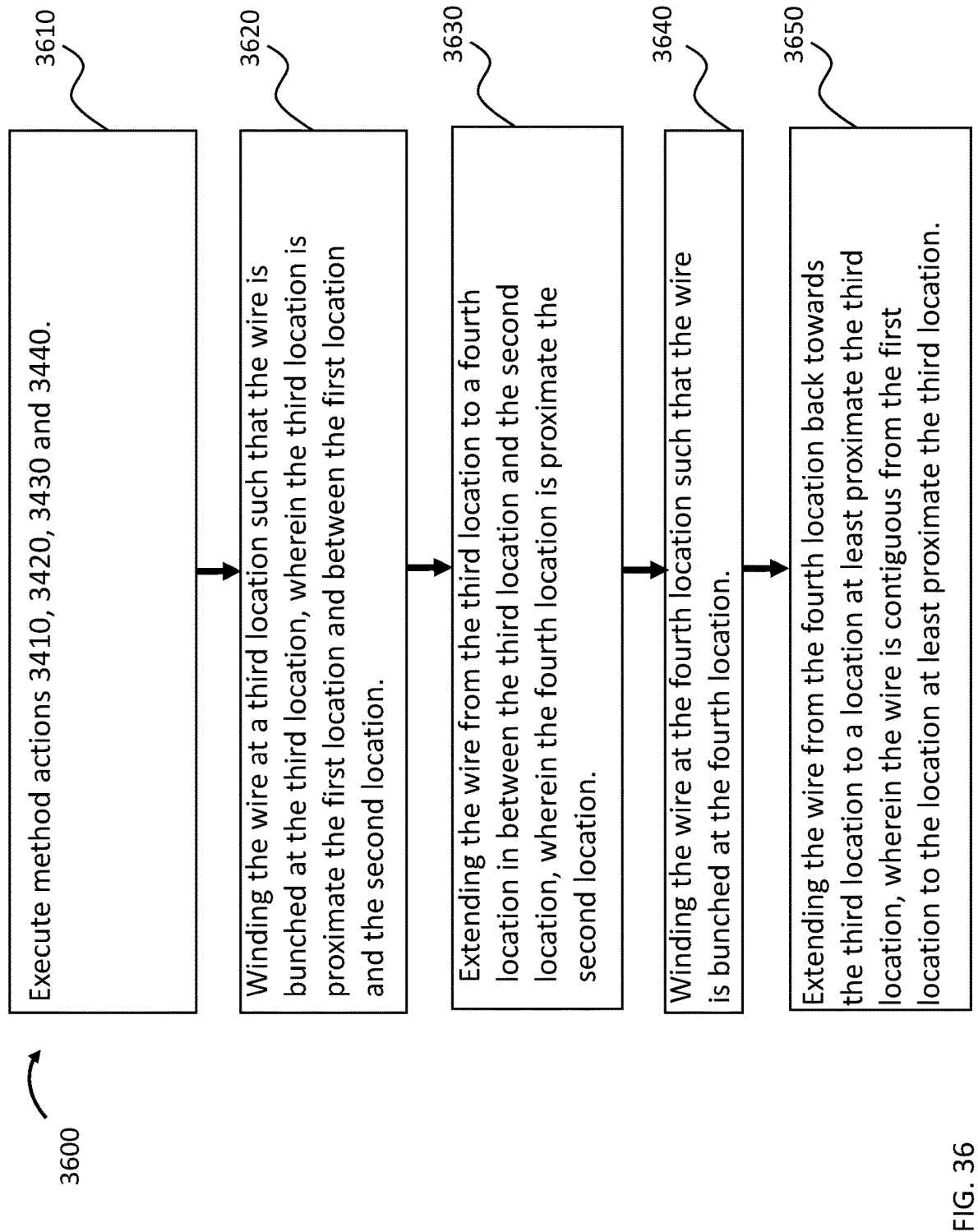

FIG. 36 presents another exemplary flowchart for an exemplary method, method 3600. Method 3600 includes method action 3610, which includes executing method actions 3410, 3420, 3430, and 3440. Method 3600 further includes method action 3620, which includes winding the wire at a third location such that the wire is bunched at the third location, wherein the third location is proximate the first location and between the first location and the second location. This is seen in, for example, in FIG. 17, where location 1703 is contiguous with location 1701, with the second location being the winding all the way over to the right. This is further seen, for example, in FIG. 21, with respect to the bunching that is located between the outermost bunchings depicted therein where after method action 3440, the wire was wound about the first location, and then extended to this third location, which is proximate the first location and between the first location and the second location.

Method 3600 further includes method action 3630, which includes extending the wire from the third location to a fourth location in between the third location and the second location, wherein the fourth location is proximate the second location. This is present in FIG. 22, where the fourth location corresponds to the bunching inboard of the bunching at the outboard right side. This would also be present in the embodiment of FIG. 17 if the wire was extended from location 1703 back towards the windings at the right side.

Method 3600 also includes method action 3640, which includes winding the wire at the fourth location such that the wire is bunched at the fourth location. Method 3600 also includes method action 3650, which includes extending the wire from the fourth location back towards the third location to a location at least proximate the third location, wherein the wire is contiguous from the first location to the location at least proximate the third location. After this action, the wire can be wound over the wire at the third location, if such was distanced from the first location (e.g., with respect to FIG. 21, wound over the windings to the immediate right of the leftmost bunching), or wound anew at a location proximate but distanced from the third location (e.g., such as, with respect to FIG. 17, wound at a location spaced from location 1703 but proximate thereto and to the right thereof).

Consistent with the teachings detailed above with respect to the electrode arrays that include 2, 3, 4, 5, 6, 7, and so on (e.g., 22) channels, in an exemplary embodiment, method 3400 is executed in a manner such that the following method action(s) is executed: winding and extending the wire so that there is a first group of at least five bunched sections that are spatially separate from each other and such that there is a second group of at least five bunched sections that are spatially separate from each other, the first group and the second group being remote from each other with respect to the formed electrode array, wherein the wire is contiguous. This embodiment would result in the electrode array having at least five channels (i.e., further actions could result in at least 22 channels). Still further, also consistent with the teachings detailed above with respect to the electrode arrays that include a plurality of channels, in an exemplary embodiment, method 3400 is executed in a manner such that the following method action is executed: winding and extending the wire so that there is a first group of at least five bunched sections that are spatially separate from each other and such that there is a second group of at least five bunched sections that are spatially separate from each other, the first group and the second group being remote from each other with respect to the formed electrode array, wherein respective bunched sections of the first group are connected via the wire to respective bunched sections of the second group by at least two sub-sections of the wire. FIGS. 17 and 18 depict how two bunched sections are connected via the wire by at least two subsections the wire: subsection 605 and subsection 606. Were this duplicated five times, one would achieve the two groups of five each.

Figure 39:
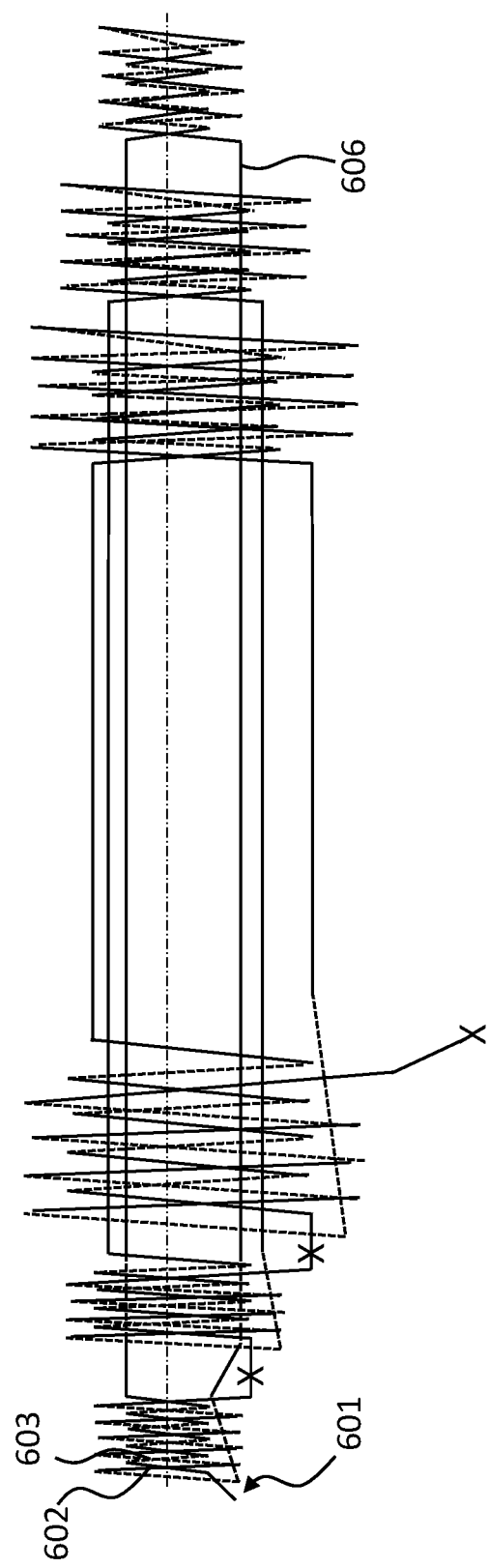

FIG. 39 depicts an exemplary embodiment of the results of executing method 3400 in a manner such that the following method action is executed: winding and extending the wire so that there is a first group of at least R bunched sections that are spatially separate from each other and such that there is a second group of at least R bunched sections that are spatially separate from each other, the first group and the second group being remote from each other with respect to the formed electrode array, wherein respective bunched sections of the first group are connected via the wire to respective bunched sections of the second group by at least two sub-sections of the wire, where R=3. In an exemplary embodiment, R=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or more.

Figure 40:
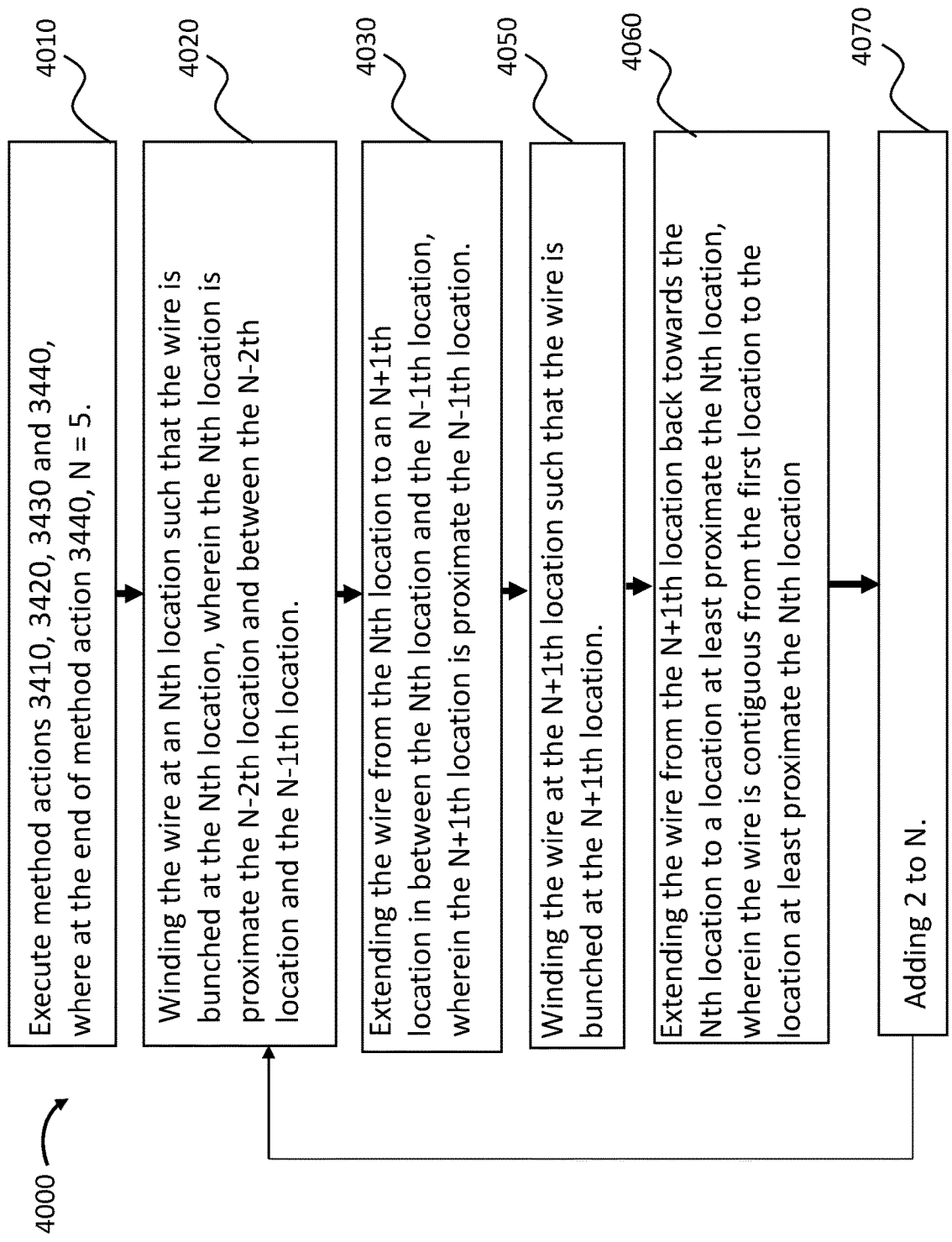
FIGS. 40-42 present an exemplary flowcharts according to some exemplary methods.

FIG. 40 presents an exemplary method, method 4000, according to an exemplary embodiment. Method 4000 includes method 4010, which includes executing method actions 3410, 3420, 3430, and 3440, where at the end of method action 3440, N=3. In this regard, in an exemplary embodiment, at the end of method action 3440, the wire could be located at, for example, with respect to FIG. 17, a location immediately adjacent location 1701 at a right side thereof. This can also correspond to, with respect to FIG. 23, location 2301. Method 4000 further includes method action 4020, which includes winding the wire at an Nth location (N=3 at this point) such that the wire is bunched at the Nth location. In some embodiments, the Nth location is proximate the N−2th location ($1^{th}$ location (which corresponds to 1st)) and between the N−2th location and the N−1th location (the 2th location). In some embodiments, the Nth location is over top/co-located with the N−2th location. In this embodiment, the Nth location could be location 1703 in FIGS. 17 and 2301 in FIG. 23 (which would also be the N−2th location).

Method 4000 further includes method action 4030, which includes extending the wire from the Nth location to an N+1th location ($4^{th}$ location, when N=3; with respect to the embodiment of FIG. 17, location 1704, and with respect to FIG. 23, location 2304) in between the Nth location and the N−1th location, wherein the N+1th location is proximate the Nth location (with respect to the embodiment of FIG. 17, the N+1th location would be 1704, where the Nth location would be 1703; with respect to the embodiment of FIG. 23, the N+1th location would be 2304). Method 4000 also includes method action 4040, which includes winding the wire at the N+1th location such that the wire is bunched at the N+1th location. Method 4000 also includes method action 4050, which includes extending the wire from the N+1th location back towards the N−1th location to a location at least proximate the N−1th location, wherein the wire is contiguous from the first location to the location at least proximate the N−1th location. Here, the with respect to FIG. 17, the location at least proximate the N−1th location would be location 1705, where N=3, and with respect to FIG. 23, location 2305, where N=3.

Method 4000 further includes method action 4070, which includes adding 2 to N. Now, where N started at 3, N is now 5. The method then returns to action 4020, and the method is repeated.

Figure 41:
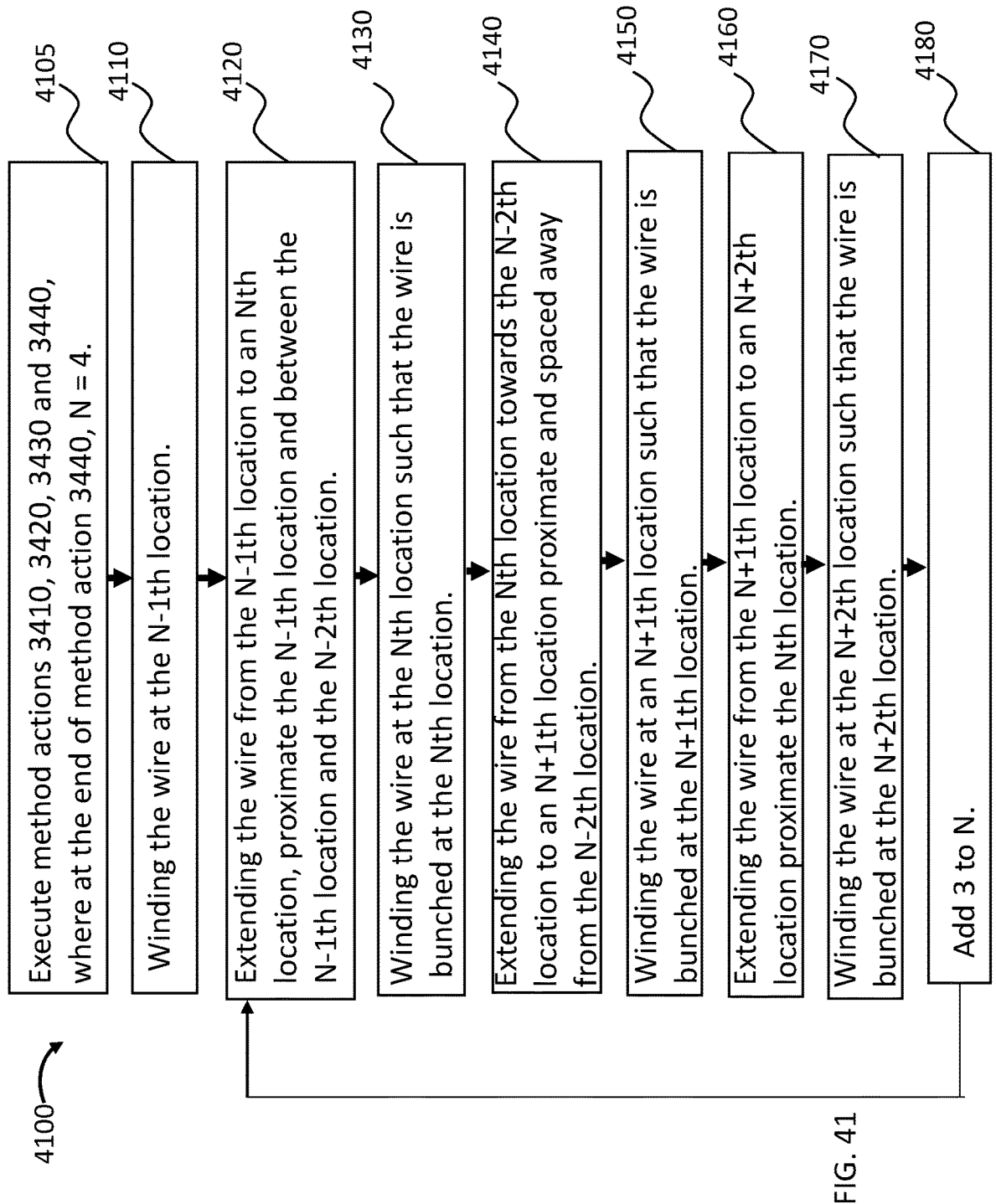

FIG. 41 presents an exemplary method, method 4100, according to an exemplary embodiment. Method 4100 includes, method action 4105, which includes executing method actions 3410, 3420, 3430 and 3440, where at the end of method action 3440, N=4. Method 4100 also includes method action 4110, which includes winding the wire at an N−1th location, the N−1th location corresponding to the location at least proximate the first location of Method action 3440. In some embodiments, the Nth location is proximate the N−3th location ($1^{th}$ location (which corresponds to $1^{st}$)-1703 in FIG. 17, for example) and between the N−3th location (1701) and the N−2th location (the $2^{nd}$ location-location 1702). In some embodiments, the Nth location is over top/co-located with the N−2th location. In this regard, this can correspond to the 2301 location in FIG. 23. In an exemplary embodiment, the wire is contiguous from the first location to a location at a completion of the winding of the wire at the N−1th location. In an exemplary embodiment, at the end of method action 4110, if the wire was severed at the completion of this method action, a single channel of an electrode array would be present. However, in this exemplary embodiment, the wire is not severed. Still, in some embodiments, the wire can be severed.

Method 4100 also includes method action 4120, which includes extending the wire from the N−1th location to an Nth location (a $4^{th}$ location, where N=4), proximate the N−1th location and between the N−1th location and the N−2th location. Here, this can correspond to the location 2304 in FIG. 23, or 1704 in FIG. 17. Method 4100 also includes method action 4130, which includes winding the wire at the Nth location such that the wire is bunched at the Nth location. This can result in the bunchings at location 2304 in FIG. 23, with the bunching that would be present at location 1704 in FIG. 17 (not shown).

Method 4100 also includes method action 4140, which includes extending the wire from the Nth location towards the N−2th location to an N+1th location ($5^{th}$ location, where N=4) proximate and spaced away from the N−2th location. In an exemplary embodiment, this can correspond to location 1705 in FIG. 17, or location 2305 in FIG. 23.

Method 4100 also includes method action 4150, which includes winding the wire at an N+1th location such that the wire is bunched at the N+1th location this can correspond to the winding seen in FIG. 23 at location 2305, or the winding that would be present in FIG. 17 at location 1705. This can correspond to a single layer winding, as is the case with respect to the winding at location 1502, or a double layer winding, as is the case with respect to the winding of 1602. (Note that this is also the case at the N−2th location as well.) Method 4100 also includes method action 4160, which includes extending the wire from the N+1th location to an N+2th location proximate the Nth location. In some embodiments, the N+2th location is proximate the Nth location ($4^{th}$ location) and between the N−2th location and the N+1th location (the $5^{nd}$ location). In some embodiments, the N+2th location is over top/co-located with the Nth location. In an exemplary embodiment, the wire is contiguous from the first location to a location at a completion of the winding of the wire at the N+2th location.

Method 4100 also includes method action 4170, which includes winding the wire at the N+2th location such that the wire is bunched at the N+2th location. Again, this can be over top the windings at N+2 or adjacent the windings at N+2 (e.g., continuous therewith). In an exemplary embodiment the wire is contiguous from the first location to a location at a completion of the winding of the wire at the N+2th location. In an exemplary embodiment, at the end of method action 4170, if the wire was severed at the completion of this method action, a second single channel of an electrode array would now be present. However, in this exemplary embodiment, the wire is not severed. Still, in some embodiments, the wire can be severed.

Method 4100 also includes method action 4180, which includes adding 3 to N, and repeating method actions 4130 to 4180 until N=B, where B can be any integer between 4 and 500, or even higher of such is enabled, such as 15, 63, etc. To be clear, the action of adding something to N is a counter step present for the purposes of sequencing the locations. Method 4100 as well as the other methods herein would not require an affirmative addition action.

Briefly, it is noted that FIG. 39 depicts an exemplary embodiment of executing method 4100 for N=9 times, where the wire is severed at the X locations to establish N/3 channels. In an exemplary embodiment, method 4100 is executed until N equals the requisite value, and then the severings are executed. Alternatively, and/or in addition to this, severing actions can be executed at various locations in between the method actions, such as after the complete wires for a given channel are laid down.

In an exemplary embodiment, with respect to method 3400, the action of extending the wire from the second location back towards the first location to a location at least proximate the first location results in the wire contacting the bunched wire at the first location (either to the side or above the bunched wire). In an exemplary embodiment, the method of 3400 further includes at least one of (i) winding the wire at the first location over top of the wire bunched at the first location such that the wire is bunched a second time at the first location; or (ii) winding the wire at a location immediately adjacent to the first location such that the wire is bunched at the location immediately adjacent to the first location; or (iii) winding the wire at a location adjacent but not immediately adjacent (e.g., a space can be between, and thus there is no continuous feature) to the first location such that the wire is bunched at the location immediately adjacent to the first location.

In an exemplary embodiment, the method includes extending the wire to a third location, and winding the wire at a third location such that the wire is bunched at the third location, wherein the third location is proximate and spaced away from the first location and, if present, the location adjacent (immediate or otherwise) the first location, and between the first location and the second location. Also, the method includes extending the wire from the third location to a fourth location in between the third location and the second location, wherein the fourth location is proximate the second location, and winding the wire at the fourth location such that the wire is bunched at the fourth location. The method can also include extending the wire from the fourth location back towards the third location to a location such that the wire contacts the bunched wire at the third location or is adjacent thereto.

The method also includes at least one of (i) winding the wire at the third location over top of the wire bunched at the third location such that the wire is bunched a second time at the third location; or (ii) winding the wire at a location immediately adjacent to the third location such that the wire is bunched at the location immediately adjacent to the third location; or (iii) winding the wire at a location adjacent but not immediately adjacent to the third location such that the wire is bunched at the location immediately adjacent to the third location. Also, in this exemplary embodiment, the wire can be contiguous from the first location to the location where the wire is bunched over top of the third location and/or bunched at the location adjacent to the third location.

In view of the above, it can be seen that in some embodiments, there is an apparatus, such as an electrode assembly 118, comprising a plurality of first wire windings (e.g., R wire windings, where R=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or more), a plurality of second wire windings (again, equal to R, for example). This can be achieved via any of the pertinent methods herein, after severing the wires as disclosed herein or variations thereof. In this embodiment, the plurality of first wire windings establish an input end of the implantable electrode assembly (i.e., the end that is attached to the receiver-stimulator of a cochlear implant, the part that has contacts that are, for example, welded to contacts or joined by another method, of the implantable electronic component). In this embodiment, the plurality of second wire windings establish a stimulation end of the implantable electrode assembly (e.g., the electrodes). The respective windings of the first wire windings are made up of the same respective single wires that make up respective windings of the second wire windings. This is, for example, seen in the embodiment of FIG. 31 and FIG. 39, after the wires are severed, for example (e.g., the leftmost winding is made of the same wire that makes up the rightmost winding, etc.). In this exemplary embodiment, at least one of (i) the plurality of second wire windings and the vicinity thereabout are free of wire ends; or (ii) respective two wire paths extend from the respective windings of the first wire windings to the respective windings of the second wire windings. With respect to the former, this can be achieved in the embodiment of FIG. 39, because all cuttings are located on the right side. With respect to the latter, this is also the embodiment of FIG. 39. In an exemplary embodiment, the respective first wire windings have at least two layers of windings, one over the other. This also corresponds to the embodiment of FIG. 39.

It is noted that the above-described embodiments vis-à-vis the plurality of first wire windings in the plurality of second wire windings are with respect to, in some embodiments, a cochlear implant electrode assembly, which includes a carrier which supports the respective windings with respect to the second wire windings, a lead assembly 184 which supports the wires that extend from the second wire windings to the first wire windings, as well as a carrier or even an extension of the lead assembly that supports the windings of the first wire windings.

In an exemplary embodiment, respective first wire windings are comprised of a first sub-winding and a second sub-winding in contact with each other or at least closer to each other than the space between the respective first wire windings (although in some embodiments, there is no first sub-winding and a second sub-winding, at least not one that can be specifically identified/distinguished with respect to the overall arrangement). This corresponds to the embodiment where the windings are over one another and the embodiment where the windings are adjacent to each other. FIG. 17 depicts the latter, except there is no space between the sub winding of location 1701 and the sub winding of location 1703, while in other embodiments, a space can be present, and if that space is less than the space between the respective first wire windings, such can correspond to this feature. That said, in some alternate embodiments, the space is equal to and/or greater than the space between the respective first wire windings. In an exemplary embodiment, consistent with the teachings detailed above, the respective second wire windings have at least two layers of windings, one over the other. In an exemplary embodiment, the respective first wire windings do not have at least two layer of windings, one over the other. Instead, in an exemplary embodiment, there is only a single layer of windings. In an alternate embodiment, the situations are reversed with respect to the first and second wire windings.

In an exemplary embodiment, the respective first wire windings are comprised of a first sub-winding and a second sub-winding in contact with each other or at least closer to each other than the space between the respective first wire windings (and in some embodiments, equal to or further away), and the first sub-winding has at least two layers of windings, one over the other, and the second sub-winding has at least two layers of windings, one over the other. This can also be the case for the respective second wire windings.

In an exemplary embodiment, there can be an apparatus, which has at least R first wire windings and a least R second wire windings (e.g., R=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more). In this example, R will be five for purposes of explanation. In this embodiment, the apparatus is an implantable electrode assembly, the five first wire windings establish an input end of the implantable electrode assembly, the five second wire windings establish a stimulation end of the implantable electrode assembly. Again, these wire windings can be established according to any of the methods detailed herein, at least after severing. Here, respective windings of the five first wire windings are made up of the same respective single wires that makes up respective windings of the five second wire windings (e.g., there are five wires). Respective sub-portions of respective wires that connect the respective windings (e.g., sub-portions 605 and 606 of FIG. 17, etc.) all at least one of extend through the windings on insides thereof or do not pass from one side of any winding to another side of any winding (e.g., with respect to FIG. 17, sub-portion 605 ends before the winding at 1702, and sub-portion 606 extends through the winding at location 1703; with respect to FIG. 32, all the connecting sub-portions extend through a winding, etc.).

In an exemplary embodiment, the respective sub-portions of respective wires that connect the respective windings never extend along outside of any winding. In an exemplary embodiment, all of the sub-portions extend only through insides of windings or do not extend/pass from one side of any winding.

In an exemplary embodiment of this embodiment, the second wire windings and the vicinity thereabout are free of wire ends. This is concomitant with the embodiment of FIG. 39. Conversely, in an exemplary embodiment, the second wire windings and/or the vicinity thereabout include wire ends. This is concomitant with the embodiment of FIG. 32. Also, as can be seen with respect to the embodiment of FIG. 39, respective two wire paths extend from the respective windings of the first wire windings to the respective windings of the second wire windings. That said, in some embodiments, only one wire path extends from the respective windings.

Consistent with the teachings detailed above, in an exemplary embodiment, the first and/or the second wire windings have at least two layers of windings, one over the other. Conversely, in an exemplary embodiment, the first and/or the second wire windings have only one layer of winding. Note that in the embodiment where the wire sub component that connects the windings extends underneath a winding, such is not a layer of a winding, even if such as pitch associated therewith. In this regard, by winding, it is meant a wire that has an angle that is less than or equal to 65° relative to a plane normal to the axis about which the wire is wound, whereas something more than that would be classified as a helix. In some embodiments, the angle is less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 degrees.

It is noted that method 4100 only specifies a minimum number of channels. By way of example only and not by way of limitation, in the aforementioned example where the number of channels equal five, the method still covers making more channels than five. That is, as long as five channels are made, such is sufficient even if a sixth or seventh or more channels are made.

Figure 42:
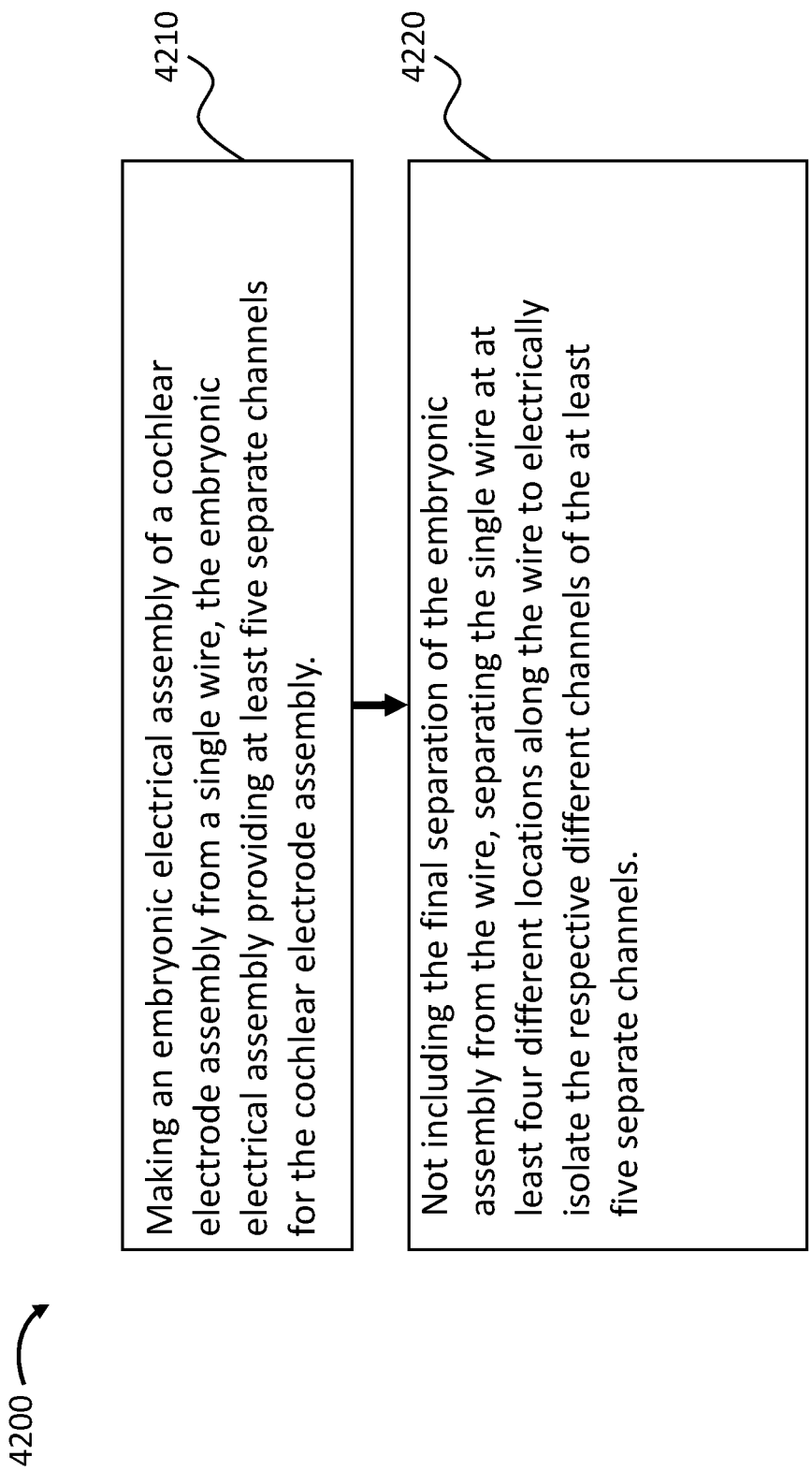

FIG. 42 presents an exemplary flowchart for an exemplary method, method 4200. Method 4200 includes method action 4210, which includes the action of making an embryonic electrical assembly of a cochlear electrode assembly from a single wire, the embryonic electrical assembly providing at least five separate channels for the cochlear electrode assembly. In an exemplary embodiment, this can correspond to executing any of the methods detailed herein such that there are two groups of five bunchings each. In this exemplary method, at the end of method action 4210, the wire extends unbroken from the beginning of the first winding to the end of the last winding (first and last being the temporal identifier). Method 4200 further includes method action 4220, which includes, not including the final separation of the embryonic assembly from the wire, separating the single wire of the embryonic electrical assembly at at least four different locations along the wire to electrically isolate the respective different channels of the at least five separate channels. In an exemplary embodiment, this can be executed utilizing a laser cutter, or a mechanical device such as a wire cutters, etc.

In an exemplary embodiment, the action of separating the single wire at at least four different locations along the wire to electrically isolate the respective different channels of the at least five separate channels comprises separating the single wire at only four different locations along the wire to electrically isolate the respective different channels. Conversely, in some exemplary embodiments, this action includes separating the single wire at more than four different locations. By way of example only and not by way of limitation, in an exemplary embodiment, the action of separating the single wire includes separating the single wire at at least eight different locations along the wire to electrically isolate the respective different channels.

By way of example only and not by way of limitation, in an exemplary embodiment of method 4200, the number of locations where the wire was separated equals the number of channels minus 1. In an exemplary embodiment, the number of locations where the wire was separated equals the number of channels minus 2. In an exemplary embodiment of method 4200, the number of locations where the wire was separated equals the number of channels minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, where the number of channels can equal to any number of channels detailed herein and/or more. In an exemplary embodiment of method 4200, the number of locations where the wire was separated equals at least the number of channels times two minus 2. In an exemplary embodiment, the number of locations where the wire was separated equals the number of channels.

By locations where the wire was separated, it is meant the gap between the wire as it otherwise would exist if the action of separating was not executed. In this regard, if, for example, in an exemplary embodiment, two or three cutting actions were executed between the winding at location 2602 and location 2603, that would still correspond to only one location where the wire is separated.

In an exemplary embodiment, the action of making an embryonic electrical assembly of a cochlear electrode assembly from the single wire provides at least R (e.g., 22, in the case of a 22 channel array) separate channels for the cochlear electrode assembly, and the action of separating the single wire at at least four different locations along the wire to electrically isolate the respective different channels of the five separate channels comprises separating the single wire at only 4 different locations along the wire to electrically isolate the respective different channels. In this embodiment, R is a value detailed above, except greater than 4. In an exemplary embodiment, the method further comprises separating the single wire at at least R-5 different locations along the wire to electrically isolate the respective different channels of the at least R-5 separate channels other than the at least five separate channels. By way of example only and not by way of limitation, in an exemplary embodiment where the number of channels equal 22, the number of locations of separation can correspond to 21, not including the final severing (of course, all of these assume that one starts with a wire that is already cut).

Figure 43:
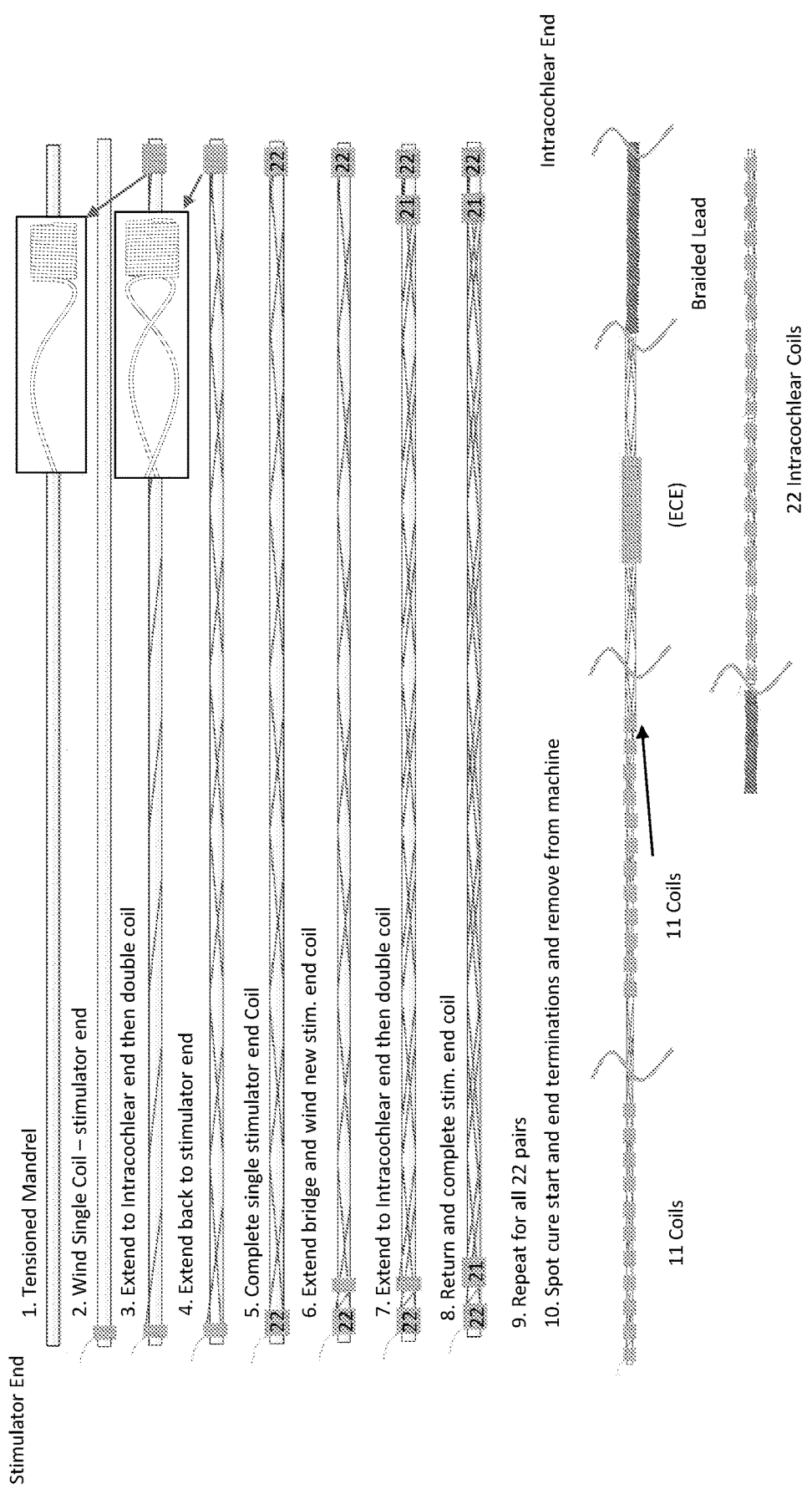
FIG. 43 presents an exemplary schematic pictorially depicting manufacture of an exemplary embryonic electrical system.

FIG. 43 presents a schematic that pictorially represents an exemplary method according to an exemplary embodiment of making an embryonic electrical system of an electrode array. As can be seen, step 1 includes obtaining mandrel and tensioning the mandrel. In an exemplary embodiment, a small amount of wet silicon can be utilized. At step 2, a single coil is wound at the stimulator end. At step 2, the winding is wound to the intracochlear end and then a double coil is established (once to the right and then once back to the left), although in an alternate embodiment, a single coil can be established by extending the helix or straight line wire sub component to the right and then winding the wire in a direction towards the left. At step 3, the wire is extended back to the stimulator end, and then at step 4 the wire is wound at a location proximate and immediately adjacent to the first winding, and then at step 5, another winding action is executed to complete a single stimulator end coil. At step 6, a wind bridge is established from the embryonic contact 22 to the embryonic portion of the future contact 21, and then a portion of that embryonic future contact 21 is wound about the mandrel. At step 7, the wire is extended to the intracochlear and then another double coil is established. At step 8, the wire is returned to left side/the stimulator end side and then the contact pad 21 is finished by establishing additional windings, which windings are immediately adjacent to the windings established at step 6. At step 9, such is repeated for all 22 pairs plus an optional extra cochlear electrode, or more. At step 10, a spot curing action is executed at start and end terminations and the embryonic electrical system is removed from the machine. In an exemplary embodiment, while not shown in FIG. 43, the embryonic electrical system is then placed in a mold and silicone is injected therein so as to establish the carrier of the electrode array. Again, as noted above, in an exemplary embodiment, the severings can be executed before the silicone is added, after a portion of the silicone is added, etc.

Figure 44:
FIGS. 44-46 present exemplary embryonic systems according to some exemplary embodiments.

FIG. 44 presents an exemplary embodiment of the intracochlear end of the embryonic electrical system of a cochlear implant electrode array, with embryonic electrodes 4444, where the most proximal and most distal electrodes are enumerated. Also seen in FIG. 44 are the electrical wires 4445 that extend from the electrodes to the stimulator end (not shown).

Figure 45:
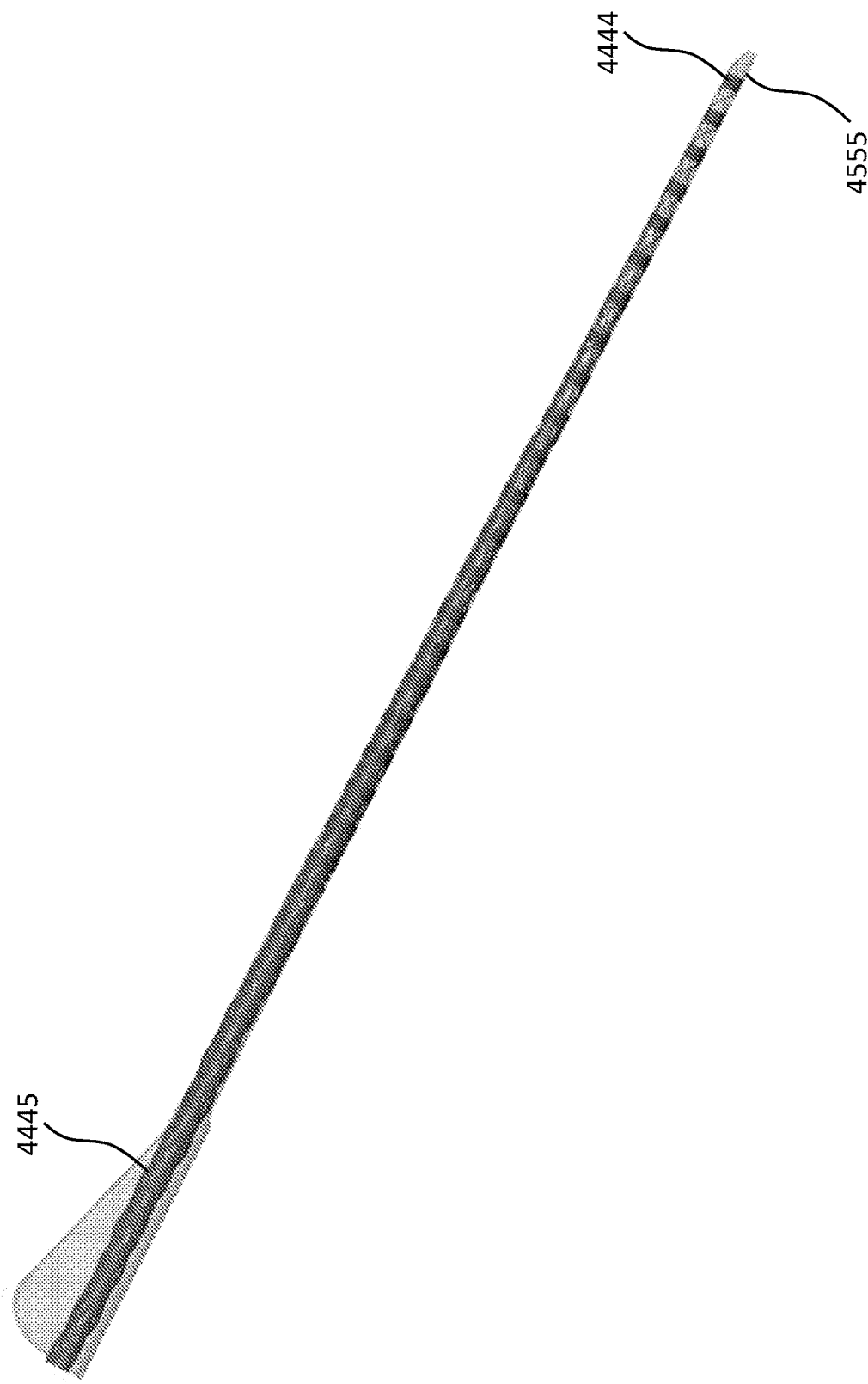

FIG. 45 presents an exemplary partial electrode array carrier assembly 4500. Here, in an exemplary embodiment, silicone is molded or otherwise applied to the embryonic electrical system of FIG. 44 to establish a support structure for the embryonic electrical system in general, and for the embryonic electrode arrays in particular. Here, the silicon carrier portion 4555 is seen along with the embryonic electrical system. Ultimately, what is seen in FIG. 45 constitutes the intracochlear portion of the electrode array, along with at least a portion of the transition region.

Figure 46:
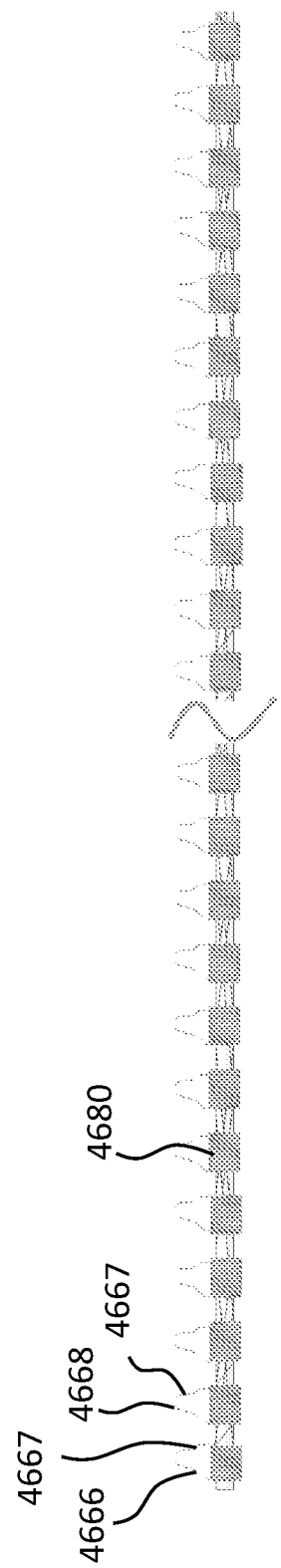

FIG. 46 presents an exemplary schematic of how the stimulator end contact bridge can be cut and also how sub-lead portions can be established which can be later welded or crimped, for example, to a contact of the stimulator assembly to establish electrical conductivity. Alternatively, or in addition to this, the sub-lead portions can be welded or crimped to electrical contacts of the lead assembly which are then in turn placed into contact with context of the stimulator receiver. In an exemplary embodiment, as will be described in further detail below, the windings/bunchings are subjected to an ablation process to expose the conductive material that is otherwise shielded by the electrically insulated material thereabout. In an exemplary embodiment, the receiver stimulator is configured to contact the conductive material of the wires at the ablated portions to establish electrical conductivity (e.g., a snap couple device, such as a spring loaded C contact, can be present in the receiver stimulator, and the bunchings 4680 can be forced into the center of the C, where the spring forces of the C will hold the bunchings in place and also maintain electrical contact between the electrical conductive material of the C contact and the exposed conductive material of the bunchings, alternatively and/or in addition to this, the ablated locations can be joined the contacts of the receiver stimulator.) The sub leads can provide redundancy with respect to establishing electrical circuits of the receiver stimulator. For example, in the embodiment depicted in FIG. 46, with the ablated contact surfaces, there can be three conductive paths from the receiver stimulator to the bunchings. In some embodiments, only the sub-lead portions are utilized. In some embodiments, only one of the sub-lead portions are utilized, as opposed to using both (an ablated section may or may not be utilized as well).

FIG. 46 depicts sub-lead portions 4666, 4667, and 4668. Sub-lead portion 4666 constitutes the beginning of the wire (601 above) that was utilized to make the entire embryonic electrical subsystem. Sub-leads 4667 and 4668 are established by severing the bridge between the winding of channel 22 (the far left winding) and the winding immediately inboard thereof.

As noted above, in an exemplary embodiment, the embryonic electrical system can be subjected to a molding operation to establish a carrier therefore. In an exemplary embodiment, it can be an initial molding, which is followed by further operation on the electrical system, such as by severing the channels/electrically isolating the channels from one another. After that, in an exemplary embodiment, the electrical system and the carrier can be subjected to a second molding process, such as an overmolding process, to finalize the overall structure of the electrode assembly. After that, in an exemplary embodiment, ablation can be utilized to remove the insulated material (as well as the silicone overmold—or in another embodiment, a separate operation can be utilized to remove the overmolding to reach the wires (or, more accurately, to reach the insulation of the wires)) so as to expose the underlying conductive material. In an exemplary embodiment, with respect to the intracochlear portion, this establishes the electrodes as it now exposes the conductive material of the wires to the ambient atmosphere. With respect to the stimulator end of the electrode assembly, this establishes the contacts (in embodiments where the bunchings are going to be utilized as contacts—as noted above, for embodiments where the lead ends can be utilized to establish electrical conductivity). In an exemplary embodiment, laser ablation is utilized, although in other embodiments, any other system of removing the insulating material and/or silicon of the carrier can be utilized.

Figure 47:
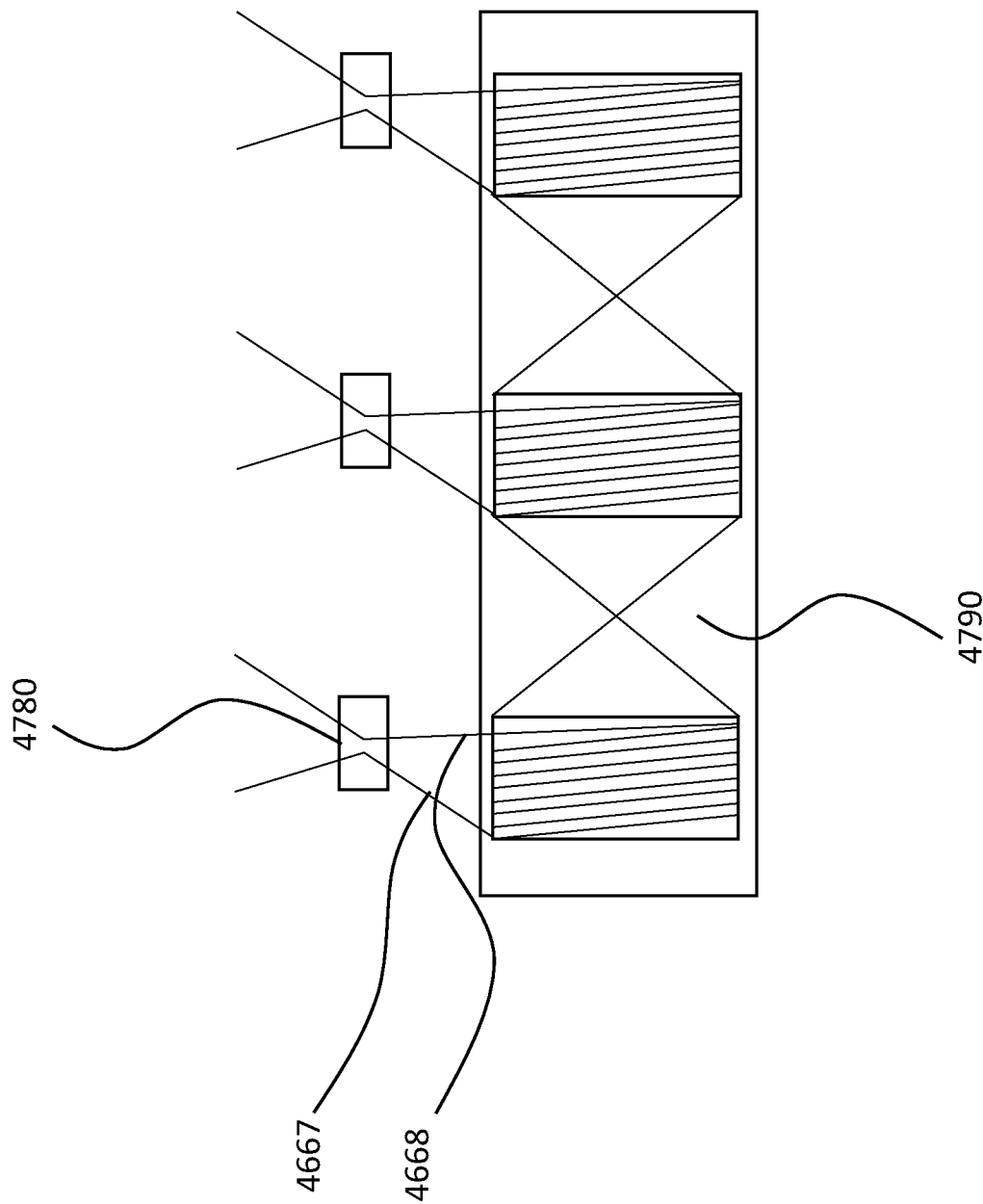
FIG. 47 presents a close-up view of a stimulator end of an electrode assembly.

FIG. 47 depicts an exemplary embodiment where the sub leads 4668 and 4667 are both attached to the same contact 4780, which, in an exemplary embodiment, can be a platinum cylinder, slotted pin or paddle (methods of joining can include resistance welding, ultrasonic bonding, laser welding, etc.) that is crimped about the wires (or, more accurately, the exposed conductors). In an exemplary embodiment, the platinum cylinder 4780 can in turn be joined to the receiver stimulator. In this exemplary embodiment, silicone body 4790 has been molded over the windings but in such a manner that the sub leads extend therethrough. In this exemplary embodiment, the windings are all covered by silicone. Only the sub leads extend therethrough and are exposed. In an alternate embodiment, the silicone 4790 can be removed at certain locations so that ablating can be executed and contacts can be exposed so as to provide another conductive path in addition to the conductive path established by the sub leads.

Figure 48:
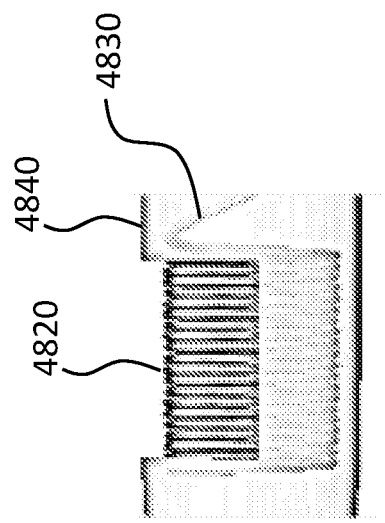
FIG. 48 presents a close-up view of a section of an electrode end of an electrode assembly.

FIG. 48 depicts an exemplary ablated section of the electrode array. As seen, the electrically conductive material 4820 (e.g., platinum strand/wire) of the wire 4830 has been exposed to the ambient environment by ablation (full band ablation or partial ablation) of the insulator material thereover and the silicone material 4840 of the carrier, thus creating an electrode. In an exemplary embodiment, this is repeated 22 times for each of the channels.

In an exemplary embodiment, the electrode assembly 118 is placed into electrical contact with circuitry of the receiver stimulator at a first location for channels 12-22, and at a second location for electrodes 1-11. These locations can be on opposite sides of the receiver stimulator, or otherwise not proximate one another. Thus, in this exemplary embodiment, there are two subsections of the overall stimulator end of the electrode assembly—one subsection that includes 11 contact locations that are welded or otherwise connected to the stimulator on one side thereof, and then another subsection of 11 contacts locations, between which extends additional lead components for those 11 contacts.

Embodiments such as the embodiment of FIG. 39 can have utilitarian value with respect to providing two separate conductive paths from the stimulator and of the electrode assembly to a given electrode. In this regard, if one of the lead portions fails, over the life of the implant, the other lead portion remains to maintain the electrical conductivity of the given electrode of the given channel with the receiver stimulator 180. To be clear, in an exemplary embodiment, in a perfectly functioning electrode assembly, both leads are utilized to conduct a current relative to the given electrode. In at least some exemplary embodiments, the current flows both ways to/from the electrode. It is that when one of the leads fails, the conductive paths are reduced by one. In any event, the double wire connection can have utilitarian value with respect to enabling redundancy as to wires connect each pad along the helix. Such can provide an increased yield if during production has multiple broken wires on different pads will not create an open circuit. By way of example only and not by way of limitation, in an exemplary embodiment the manufacturing process can result in wires that are accidentally broken (and note that this does not correspond to the actions of severing or cutting detailed herein—this is accidental, unwanted). Accordingly, in an exemplary embodiment, there is a method of manufacturing a completed lead assembly and providing the lead assembly for implantation and a method of implanting a lead assembly which has broken wires (as opposed to intentionally cut wires) but all electrode channels of the electrode assembly are available. Of course, as detailed above, such can provide utilitarian value with respect to reducing the likelihood of an open circuit when the electrode assembly is utilized.

Such features can also remove any need to perform bridge cutting at the intracochlear ends. In this regard, in an exemplary embodiment, there are only bridge cuttings at the stimulator end of the electrode array. Such can have utilitarian value with respect to reducing the likelihood of a scenario of protruding wires at the intracochlear end and/or a scenario where the intracochlear coils (e.g., bunchings) could unwind during insertion or after insertion.

It is noted that the phrase "bunchings" as used herein encompasses wires that are at least wound so as to abut one another or otherwise are provided with such a pitch that there is at least effectively no room between the windings to place another wire that would be level with the windings (i.e., any wire that would be attempted to be placed in between the windings would be proud of the windings already present). In an exemplary embodiment, the winding pitch matches the diameter of the wire, and in other embodiments, it is at least more than 0.1, 0.2, 0.3, 0.5, 0.75, 1, 2, 3, 4, 5, 6, 7, 8, 9, 10, 15, 20, 25, 30, 40, 50, 60, 70, 80, 90, 100, 125, 150, 175, 200 or more percent greater than the diameter of the wire.

In view of the above, it can be understood that in at least some exemplary embodiments, there is an exemplary method that includes the action of winding a wire at a first location at a stimulator end of an embryonic conductive system is executed by winding the wire about a first mandrel and/or the action of winding a wire at a second location at an intracochlear end is executed by winding the wire about the first mandrel or a second mandrel. That is, in an exemplary embodiment, two or more mandrels can be utilized. In an exemplary embodiment, the formed electrode assembly includes the first mandrel and/or the second mandrel and/or a portion of the first mandrel and/or a portion of the second mandrel. In this regard, in an exemplary embodiment, the mandrel can be a structural component of the finalized electrode array. That is, in an exemplary embodiment, there is a method that includes removing a portion of the mandrel from the rest of the mandrel, or utilizing the entire mandrel (e.g., where there are a plurality of mandrels utilized), such as the mandrel that is utilized to establish the bunchings of the intracochlear portion, in an electrical assembly that is ultimately used in the cochlear implant and implanted in a recipient. In an exemplary embodiment, the mandrel can be a Nitinol product, and thus can be used to provide structural support for a finalized shape of the electrode array. In an exemplary embodiment, the mandrel can have a shape memory such that during winding, the mandrel can be held straight, such as by tensioning the ends thereof, and then, after the tension is released, the mandrel can curve back to its natural state, thus providing a support structure for a so-called curved electrode array. Accordingly, in an exemplary embodiment, the mandrel can be utilized to implement a curly electrode array. The opposite can be the case as well. Also, consistent with the teachings detailed above, in an exemplary embodiment, the mandrel can be a curved mandrel while the windings are placed there about.

In an exemplary embodiment, the mandrel can be a single mandrel, but can have weakened areas along a length thereof (e.g., slits, areas of removed material, etc.) that enable improved ease of breakage, severing relative to that which would be the case in the absence of the weakened areas. By way of example only and not by way of limitation, in an exemplary embodiment, the mandrel could be weakened between the location where the mandrel supports the windings of the electrode array and the mandrel supports the helix region. The mandrel could be subjected to Euler buckling or the like, so as to "snap" the mandrel at a location away from the electrode array, and then the portion of the mandrel that supports the helix can be removed while keeping the remaining portion of the mandrel in the electrode array.

In an exemplary embodiment, the teachings detailed herein are executed such that all pads are wound starting from the direction of travel.

Accordingly, in an exemplary embodiment, the action of making the embryonic electrical assembly is executed by winding a single electrical wire about a mandrel, and optionally extending the single electrical wire along the wire, without reversing a direction of the winding. In an exemplary embodiment, with respect to winding the wire about a straight mandrel, the local angle of extension of the wire relative to the longitudinal axis of the mandrel does not experience a turn that is greater than 90 degrees. In an exemplary embodiment, there are no sharp bends of the wire. In an exemplary embodiment, with respect to a rotating mandrel and/or with respect to a rotating wire nozzle, the direction of rotation does not change during the manufacturing process, although in some embodiments, the rotation may stop, such as for example, where the wires are extended from the connector region to the electrode region.

Figure 49:
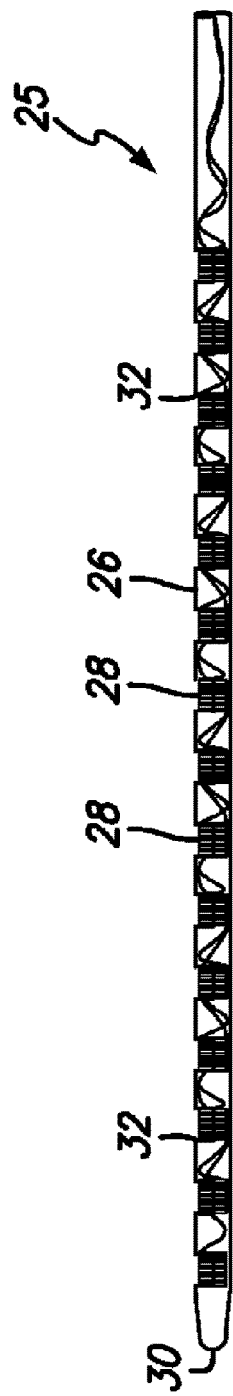

FIG. 49 illustrates an example electrode array construction 25 comprising an outer cover, carrier or insulating sheath 26 formed from an electrically non-conductive material. In an example, the carrier is formed from a biocompatible material such as silicone or the like. The electrode construction comprises a plurality or an array of electrode contacts or stimulation sites 28 positioned along a length of the construction extending from distal tip 30 therealong. As described in greater detail below, portions of the carrier are removed along the electrode construction to form openings 32 therethrough to permit direct contact between the stimulation sites 28 and an adjacent object when placed thereagainst. In some instances, the contact 28 are established or otherwise provided or otherwise correspond to the contacts established via the winding actions detailed above.

Figure 50:
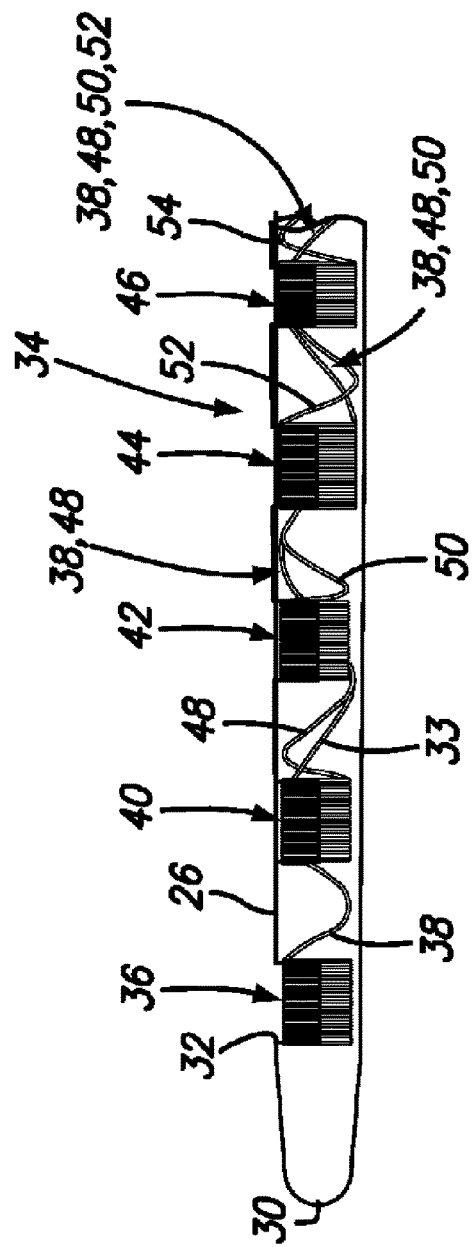
Figure 51A:
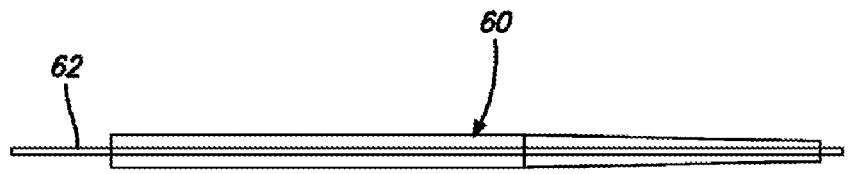
Figure 51B:
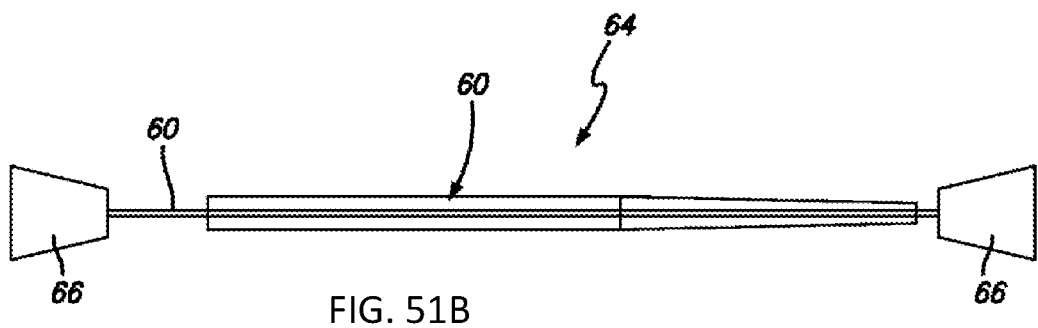
Figure 51C:
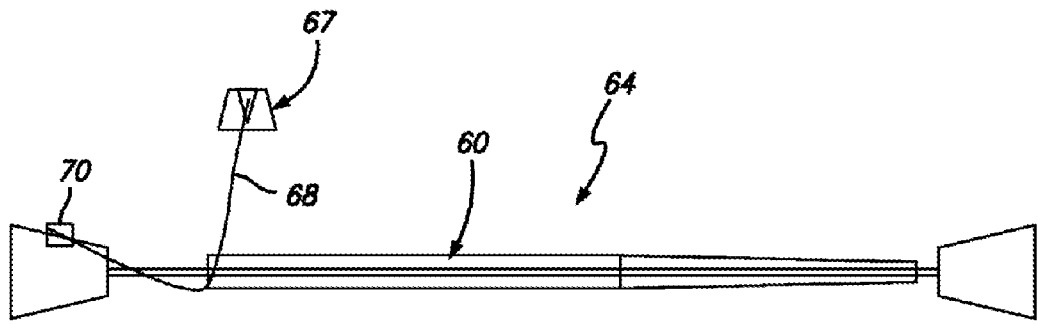
Figure 51D:
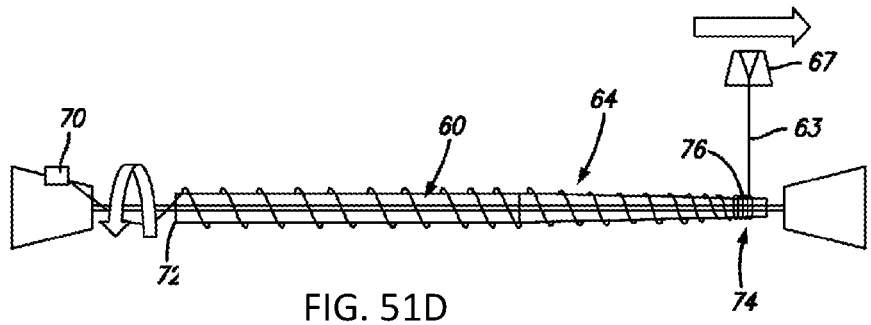
Figure 51E:
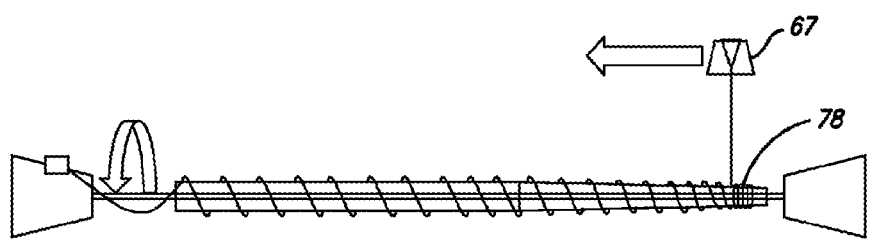
Figure 51F:
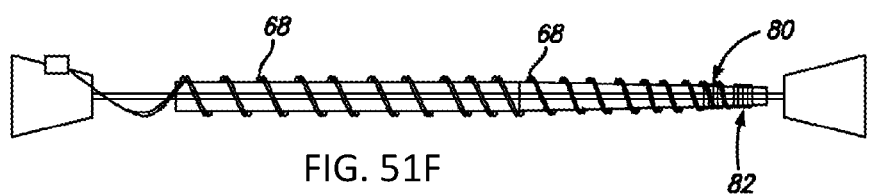
Figure 51G:
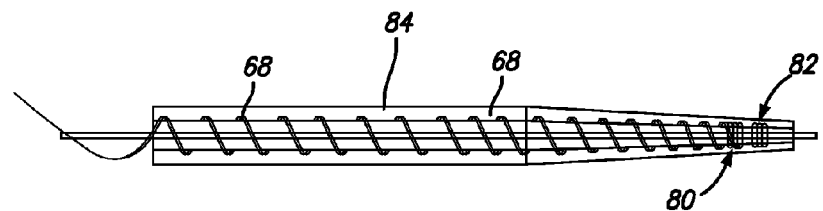
Figure 51H:
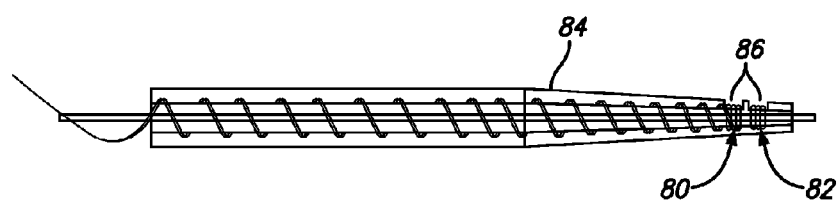
Figure 51I:
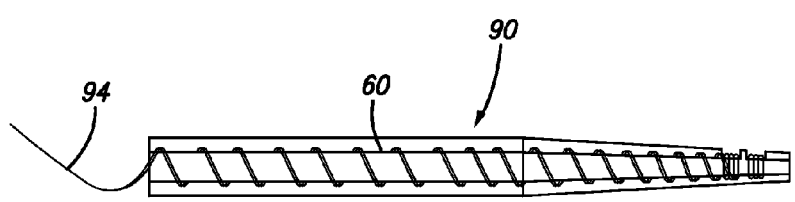

FIG. 50 illustrates an enlarged view of a stimulating region 34 of the example electrode construction (illustrated in FIG. 49) comprising an array of the stimulation sites extending from the tip 30. The stimulation sites are each formed from a winding of wire, wherein each wire that is wound to form a stimulation site extends therefrom along a length of the electrode construction away from the tip to a connection point. Thus, electrode constructions as disclosed herein comprise a plurality of such stimulation sites that are each formed from a winding of wire, and wherein each wire used to form a respective stimulation site extends therefrom along a length of the electrode construction to a connection point for connection with another device.

Moving from left to right, a first stimulation site 36 is positioned adjacent the tip 30 and is formed from a first winding of wire 38. In an example the wire is formed from an electrically conductive metallic material, and an example the material is platinum. The wire used to form electrode constructions as disclosed herein can be insulated or non-insulated. In an example, the wire is insulated. However, it is possible to use non-insulated wire in the pre-manufacturing form, in which case alternative insulating means and methods for forming the same are used during the process of making the electrode construction. The wire 38 used to form the first stimulation site 36 extends therefrom within the electrode construction in a spiral fashion past second, third, fourth and fifth stimulation sites, 40, 42, 44, 46, respectively. Each of the second, third, fourth and fifth stimulation sites are formed in a similar manner from a winding of a separate wire, 48, 50, 52 and 54, respectively for each, which wires each extend in a spiral or helically-wound fashion therefrom within the electrode construction.

In an example, the electrode construction can comprise any number of stimulation sites formed in the manner described. The stimulation sites can be positioned and/or sized, e.g., to provide a desired contact surface area, and/or the openings within the carrier can be oriented and sized, as called for by the particular application to perform the desired function of providing a stimulating signal to an adjacent contacting surface. In an example, the wire used to form the electrode construction stimulation sites is insulated, and such insulation is removed in the location of the site during or subsequent to formation of the opening 32 through the carrier 26. Constructed in this fashion, the insulation on the wire operates to prevent any undesired shorts from occurring as the wire used to form the sites passes within the construction along other sites.

In an example, the stimulation sites can be formed from one or more windings of the wire, such as by way of example only and not by way of limitation, as established according to the teachings detailed herein. In an example, there can be utilitarian value with respect to stimulation sites be formed from at least two layers of the wire winding. In such example, the insulating material of the second or top most winding of the wire is removed and the insulating material of the first or inner most winding of the wire is preserved, thereby ensuring a desired degree of insulation within the construction. Thus, there can be utilitarian value with respect to using multiple layers or windings of wires is that when the top layer is ablated away or otherwise removed to expose the stimulation site, the underlying bottom layer provides an insulative barrier that protects the wires running thereunder from electrical short. Also, the use of multiple layers or windings of wire operates to provide mechanical support to the exposed stimulation site should the method used to remove the insulation from the top wire layer also inadvertently remove some of the top layer wire itself.

Another feature of multiple layers or windings of the wire for forming the stimulation sites is that it can provide additional surface area resulting from small gaps that exist between adjacent wire windings forming a stimulation site. The additional surface area resulting from such gaps between adjacent wires within a winding is additive to the additional surface area that results from forming the stimulation site from wire having a round construction as contrasted with conventional stimulation sites formed from a flat piece of metal. The exposed semicircular shape of each exposed wire, when contrasted to a flat piece of metal, provides such an increased surface area, which can operate to make the stimulation site more effective. In an example, the insulation on the outermost portion of the top layer of wire winding as well as the insulation on a top portion of the underlying layer of wire winding is removed during the process of exposing the stimulation site. The exact number of layers of wire windings used to form the stimulation sites can vary depending such factors as the desired height of the site, e.g., useful to provide a stimulating signal to an adjacent contacting surface, the diameter and size of the wire that is used, and the particular end-use application.

FIGS. 51 *a* to 5 *k* illustrate electrode constructions at different stages of being manufactured according to an example method of making. It is noted that these figures do not correspond to the method actions/embodiments established above with respect to FIGS. 6-56, but that in some instances, these figures are modified so as to achieve the aforementioned embodiments. In this regard, by way of example only and not by way of limitation, the winding directions and the start locations, for example, would be started differently to correspond to the teachings detailed above. Some areas of differences are interjected below, while others are not for purposes of linguistic economy. Referring to FIG. 51 *a*, in a first step, a sleeve 60 is disposed onto a cylindrical mandrel 62 and is used to form an inner wall structure for forming the windings of wire thereon. The sleeve can be provided in the form of a preformed, e.g., a preformed, part, or can be formed on the mandrel from dispensing a suitable material thereon that cures or otherwise hardens to form the sleeve. In a preferred, the sleeve is provided in the form of a preformed part and then smoothly the construction can be removed from the mandrel. The preformed part can be configured having a constant or a variable cross-sectional thickness depending on the particular external surface desired for a particular end-use application. The mandrel 62 can be made of metal, plastic or thread. In an example, the mandrel 62 is made from metal and the sleeve 60 is made from a biocompatible polymeric material such as Nusil MED 4860/4213 or the like.

In the illustrated example, the sleeve 60 has a first section defined by a constant cross-sectional thickness, and a second section having a variable cross-sectional thickness that is tapered moving longitudinally therealong. This is but one example sleeve configuration, and it is to be understood that sleeves useful for forming electrode constructions as disclosed here can have a variety of different cross-sectional configurations at different locations depending on the particular end-use application. In another exemplary electrode construction, thus sleeve 60 is configured having a generally tapered cross section moving away from a tip to about half way along the length of the construction, and then having a variable cross section expending within the remaining half of the construction. The different sleeve cross sections can be provided to introduce different levels of flexibly and/or stiffness to the construction to meet needs of the end-use application.

While a sleeve having a circular cross section is illustrated, it is to be understood that sleeves having non-circular cross sections can be used depending on the particular electrode construction end-use application. If desired, the surface of the mandrel can be coated or otherwise treated with a nonstick coating to facilitate removal of the mandrel from the sleeve during a later stage of manufacturing. In an example, the sleeve is sized having a diameter smaller than that of the external diameter of the electrode array.

Referring to FIG. 51 *b*, the assembly 64 of the mandrel 62 and the sleeve 60 is tensioned on a winding machine 66. In FIG. 51 *c*, a wire guide 67 is positioned adjacent the assembly 64, wherein the wire guide is configured to dispense wire 68, e.g., disposed on a spool or the like, used to form the stimulation sites onto the sleeve 60. Wire 68 useful for forming electrode constructions as disclosed herein include those formed from conventional metallic materials. In applications where the electrode construction is to be implanted within a recipient, the wire can be coated platinum wire, or wire made from gold or biocompatible metals or metal alloys, such as platinum-iridium or the like. The coating can be formed from polymers such as parylene, sulphone-based polymers, or similar polymers giving desired properties of electrical insulation and physical separation.

The particular diameter size of the wire used can be different and such difference can be used to introduce different features and/or properties to the electrode construction. For example, the diameter of wire selected to make the different stimulation sites can increase moving away from the stimulation sites positioned adjacent the tip, thereby providing both a greater degree of flexibility at and adjacent the tip (e.g., so as to minimize any damage during and after fitment when the end-use application is an implanted medical device), and to provide an increased degree of rigidity away from the tip to provide an improved degree of control during such fitment. Additionally, the use of thicker wire makes for an overall more robust construction. In an example, platinum-iridium wire is used, wherein iridium is used to provide an improved degree of stiffness to the wire.

Referring still to FIG. 51 *c*, an end of the wire 68 from the wire guide is 67 is attached to a wire attachment feature or mechanism 70 that rotates with the assembly 64 as the wire guide 67 remains in a non-rotating state, and that is configured to hold the wire in place. The wire guide 67 is configured to move back and forth along the length of the assembly 64. Referring to FIG. 51 *d*, the wire guide 67 moves along the length of the assembly 64 as the assembly is rotated and feeds wire 68 onto the surface of the sleeve 60 so that the wire is disposed thereon in a spiral or helical fashion. If desired, the wire dispensed onto the sleeve can be fed onto through a silicone applicator or the like for the purpose of applying a very thin coating of glue to hold the wires in place over the sleeve. The glue also acts to provide adhesion between individual strands of wire. It is noted that in at least some examples, consistent with the teachings detailed above, a winding bunching is established at the left side of the figure, prior to extending the wire to the bunching at the right side. An example, silicone that can be used for this purpose is MED 4213 from Nusil. Alternate adhesives may be used. Instead of feeding the wire through a silicone applicator, the adhesive material can be applied by brush/spray directly onto the sleeve to thereby provide a desired wire adhesion. Additionally, if the wire used is insulated, the wire can be fed through a device useful for providing an insulating layer thereon prior to being dispensed onto the sleeve.

As shown in FIG. 51.d, the wire guide 67 is moved along the length of the sleeve as the sleeve is being rotated to a position on the sleeve. The wire 68 is wound in helical fashion onto the sleeve lengthwise from end 72 adjacent the wire attachment feature 70 to a location on the sleeve adjacent an opposite end that corresponds to the electrode construction first stimulation site. In an example, the sleeve is rotated relative to the wire guide 67 using a lathe-type set up, and the wire 68 is disposed onto the sleeve by the lateral movement of wire guide 67.

Referring still to FIG. 51 d, when the first stimulation site location 74 is reached, a desired number of wire windings are wound in serial fashion adjacent one another to provide a desired stimulation site or pad width. The stimulation site width and height or thickness can vary depending on the particular end-use application, thus the following example is provided for reference as it relates to one end-use example where a stimulation site width of approximately 300 microns is desired. In an example, a desired wire 68 useful for making electrode constructions has a thickness of approximately 25 microns, and the desired stimulation site width is achieved by providing a first layer of windings 76 comprising approximately 12 turns of wire wound side-by-side.

Referring to FIG. 51 e, in an example, a desired stimulation site height is approximately 50 microns, and the mandrel and wire guide 67 is operated to provide a second layer of windings 78 comprising another 12 turns of wire so that it overlaps the first set of wire windings to thereby provide the desired first stimulation site height. In an example, once the first stimulation site is formed, the wire used to form the same is then secured into place and is cut before the wire guide 67 is returned to its initial or starting position for forming a subsequent stimulation site.

FIG. 51 f illustrates the electrode construction after a second stimulation site 80 has been formed in the same manner as the first stimulation site 82. The second stimulation site 80 is formed at a location adjacent the first stimulation site 82. The sequence of forming stimulation sites according the method described above can be repeated as needed for as many stimulation sites called for by the particular end-use application, wherein the wire 68 used to form each stimulation site extends helically from the wire attachment mechanism to its respective stimulation site.

It is noted that while the embodiments of these figures depict the wire having a change of direction, as noted above, in an alternate embodiment, the wire does not change direction, and thus in some embodiments, the depicted helix regions would be crisscross, as opposed to the aligned version depicted in the figures. Again, the embodiments of these figures present an exemplary embodiment that is different than the embodiments detailed above, where these method actions would be adjusted accordingly to implement the teachings detailed above vis-à-vis FIGS. 6-56.

While an example method of making the stimulation sites has been disclosed and illustrated, it is to be understood that other methods of forming the wire-wound stimulation sites are within the scope of the electrode construction as disclosed herein. For example, instead of forming each stimulation site by running wire from an opposite end of the sleeve, the stimulation sites can be formed by starting at the stimulation site location and afterwards running the wire used to form the same helically to the opposite end of the sleeve. Additionally, it is to be understood that the simulation sites as formed herein can be positioned having a uniformly-spaced or non-uniformly spaced arrangement depending on the particular end use application. In a particular example, where the electrode construction is used in conjunction with a cochlear hearing implant system, such construction comprises approximately 22 stimulation sites that are located to make contact against the human cochlea. Also, the windings detailed above with respect to FIGS. 6 to 56 can be established by extending the wire as detailed and associated therewith.

Referring to FIG. 51 g, a thin silicone layer 84 is disposed by various means, e.g., by molding, dispensing, dipping, spraying, or the like, over the wires 68 to provide protection and mechanical strength. In an example, the silicone layer is additionally disposed over the stimulation sites 80 and 82. It is also desired that the ends of the wires extending from the sleeve remain exposed to facilitate providing a connection point to further device, e.g., an implant component or the like. Molding or jetting may be used as a method for applying this layer of silicone. The thin silicone structure applied during this step forms the electrode construction external carrier or sheath.

Referring to FIG. 51 h, portions of the outer silicone layer 84 are ablated or otherwise removed to provide openings 86 therethrough at positions above each of the stimulation sites 80 and 82 to thereby expose a desired portion of the underlying stimulation sites. During such step, the insulation on the top layer of the wire winding forming each stimulation site is also removed so that the stimulation sites exposed through the openings 84 comprise bare metal wire. The step of ablating can be done by UV or laser treatment, or by mechanical and/or chemical means. The accurate location of the stimulation sites will allow the ablation step to be conducted without use of vision-based machine guiding devices. This is in contrast to conventional stimulation sites made from metal pads that move during the manufacturing process and, thus need a feedback mechanism to determine an exact location to ablate.

Referring to FIG. 51 i, the so-formed electrode construction 90 is removed/slide off of the mandrel, and the loose wire ends 94 extending from the end of the construction are configured to provide the desired mechanical and electrical connection with another device. At the point of its removal from the mandrel, the electrode construction 90 comprises a hollow center cavity as defined by a wall structure of the sleeve 60. The hollow cavity can be filled with a material or left hollow depending on the particular end-use application. For example, the hollow cavity can be filled with a suitable material such as silicone (MED 4880 or similar) to create a straight electrode array. Alternatively the center cavity could be filled with a preformed stiffener, which can be made of metal or a polymer. This may also be formed with a nitinol or similar shape memory alloy on its own or as a combination with silicone. The function of the stiffener is to provide desired rigidity to the electrode construction, and to create a desired final shape. The stiffener may have varying cross section along the length to provide precise control of the above outcomes.

If desired, the electrode construction as formed according to the above disclosed method can be molded into a particular shape for its determined end-use application. In an example where the electrode construction is to be used as a cochlear implant, the electrode construction is removed from the mandrel and is placed into a die, e.g., a curved die, replicating the shape of a human cochlea. While an example method of making electrode constructions has been described above with reference to particular figures and method steps, it is to be understood that electrode constructions as disclosed herein can be made by alternative methods wherein one or more of the above-described steps are combined, or one or more of the above-disclosed steps are broken up or separated into two or more steps, and such alternative methods are intended to be within the scope of this disclosure.

As noted above, some and/or all of the teachings detailed herein can be used with a hearing prosthesis, such as a cochlear implant. That said, while the embodiments detailed herein have been directed towards cochlear implants, other embodiments can be directed towards application in other types of hearing prostheses, such as by way of example, other types of electrode arrays used in medical devices (e.g., pacemakers, nerve stimulators, etc.). Indeed, embodiments can be utilized with any type of medical device that utilizes an implanted electrode array, or even a non-implanted array, at least if there is utilitarian value with respect to conducting a test for an open circuit while the electrode array is located within packaging.

It is noted that any disclosure with respect to one or more embodiments detailed herein can be practiced in combination with any other disclosure with respect to one or more other embodiments detailed herein.

It is noted that some embodiments include a method of utilizing a system having one or more or all of the teachings detailed herein and/or variations thereof. In this regard, it is noted that any disclosure of a device and/or system herein also corresponds to a disclosure of utilizing the device and/or system detailed herein, at least in a manner to exploit the functionality thereof. Further, it is noted that any disclosure of a method of manufacturing corresponds to a disclosure of a device and/or system resulting from that method of manufacturing. It is also noted that any disclosure of a device and/or system herein corresponds to a disclosure of manufacturing that device and/or system. Moreover, any disclosure of a method action herein also corresponds to a system and/or a device for executing that method action. In this regard, in an exemplary embodiment, there is an apparatus and/or system that is configured so as to enable any one or more of the method actions detailed herein. In this regard, in an exemplary embodiment, there is a device that is configured to enable one or more or all of the method actions detailed herein to be executed, manually and/or automatically.

Any disclosure herein of any given teaching can be combined with any other disclosed teaching herein unless otherwise indicated or unless the art does not enable such. Any disclosure herein of a given teaching can be excluded from utilization with any other teaching detailed herein unless otherwise indicated or unless the art does not enable such.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An apparatus, comprising:
a plurality of first wire windings;
a plurality of second wire windings, wherein
the apparatus is an implantable electrode assembly,
the plurality of first wire windings establish an input end of the implantable electrode assembly,
the plurality of second wire windings establish a stimulation end of the implantable electrode assembly, and
respective windings of the first wire windings are made up of the same respective single wires that make up respective windings of the second wire windings.

2. The apparatus of claim 1, wherein at least one of:
the plurality of second wire windings and the vicinity thereabout are free of wire ends; or
respective two wire paths extend from the respective windings of the first wire windings to the respective windings of the second wire windings.

3. The apparatus of claim 2, wherein:
the plurality of second wire windings and the vicinity thereabout are free of wire ends.

4. The apparatus of claim 2, wherein:
respective two wire paths extend from the respective windings of the first wire windings to the respective windings of the second wire windings.

5. The apparatus of claim 2, wherein:
the respective first wire windings have at least two layers of windings, one over the other.

6. The apparatus of claim 1, wherein:
the plurality of first wire windings comprise at least five first wire windings;
the plurality of second wire windings comprise at least five second wire windings, wherein
the five first wire windings establish the input end of the implantable electrode assembly,
the five second wire windings establish the stimulation end of the implantable electrode assembly,
respective windings of the five first wire windings are made up of the same respective single wires that makes up respective windings of the five second wire windings, and
respective sub-portions of respective wires that connect the respective windings all at least one of extend through the windings on insides thereof or do not pass from one side of any winding to another side of any winding.

7. The apparatus of claim 6, wherein:
the respective sub-portions of respective wires that connect the respective windings all extend through the windings on insides thereof.

8. The apparatus of claim 6, wherein:
the respective sub-portions of respective wires that connect the respective windings never extend on an outside of a winding.

9. The apparatus of claim 6, wherein:
the respective sub-portions of respective wires that connect the respective windings all do not pass from one side of any winding to another side of any winding.

10. An assembly, comprising:
a receiver-stimulator of a cochlear implant; and
the apparatus of claim 1, wherein
the input end of the apparatus is attached to the receiver-stimulator, and the stimulation end is remote from the receiver-stimulator.

11. The assembly of claim 10, wherein:
all wire antenna coils of the assembly are located on a side of the assembly opposite the implantable electrode assembly.

12. The apparatus of claim 1, wherein:
respective windings of the plurality of second wire windings respectively establish respective tissue stimulating electrodes of the implantable electrode assembly.

13. The apparatus of claim 1, wherein:
the apparatus is an electrode contactless implantable electrode array.

14. The apparatus of claim 1, wherein:
the stimulation end of the implantable electrode assembly is an elongate arrangement wherein respective windings of the plurality of second wire windings are arrayed serially along a longitudinal direction of the elongate arrangement.

15. The apparatus of claim 1, wherein:
the respective first wire windings are comprised of a first sub-winding and a second sub-winding in contact with each other or at least closer to each other than the space between the respective first wire windings; and
the first sub-winding has at least two layers of windings, one over the other; and
the second sub-winding has at least two layers of windings, one over the other.

16. The apparatus of claim 1, wherein:
a direction of extension of the wires are nowhere reversed.

17. The apparatus of claim 6, wherein:
the second wire windings and/or the vicinity thereabout include wire ends.

18. The apparatus of claim 1, wherein:
respective windings of the plurality of first wire windings establish respective input contacts of the apparatus.

19. The apparatus of claim 1, wherein:
the implantable electrode array includes an electrode array; and
the stimulation end is the electrode array.

20. The apparatus of claim 1, wherein:
respective windings of the plurality of first wire windings are respectively in direct physical electrical conducive contact with conductors of a component to which the implantable electrode assembly is attached.

21. The apparatus of claim 1, wherein:
the implantable electrode assembly includes an elongate lead sub-assembly, the input end being located at one end of the elongate lead sub-assembly and the stimulation end is located at a side of the lead sub-assembly opposite the one end.

22. The apparatus of claim 2, wherein:
the respective first wire windings are comprised of a first sub-winding and a second sub-winding in contact with each other or at least closer to each other than the space between the respective first wire windings.

23. The apparatus of claim 2, wherein:
the respective first wire windings are comprised of a first sub-winding and a second sub-winding in contact with each other or at least closer to each other than the space between the respective first wire windings; and
the first sub-winding has at least two layers of windings, one over the other; and
the second sub-winding has at least two layers of windings, one over the other.

24. The apparatus of claim 6, wherein:
the second wire windings and the vicinity thereabout are free of wire ends.

25. The apparatus of claim 6, wherein:
respective two wire paths extend from the respective windings of the first wire windings to the respective windings of the second wire windings.

26. The apparatus of claim 6, wherein:
the first and second wire windings have at least two layers of windings, one over the other.

* * * * *